(12) United States Patent
Katz et al.

(10) Patent No.: US 9,834,793 B2
(45) Date of Patent: *Dec. 5, 2017

(54) METABOLICALLY ENGINEERED CELLS FOR THE PRODUCTION OF RESVERATROL OR AN OLIGOMERIC OR GLYCOSIDICALLY-BOUND DERIVATIVE THEREOF

(71) Applicant: Evolva SA, Reinach (CH)

(72) Inventors: Michael Katz, Malmo (SE); Hans Peter Smits, Holte (DK); Jochen Forster, Copenhagen (DK); Jens Bredal Nielsen, Charlottenlund (DK)

(73) Assignee: EVOLVA SA, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/690,542

(22) Filed: Apr. 20, 2015

(65) Prior Publication Data

US 2015/0361455 A1   Dec. 17, 2015

Related U.S. Application Data

(63) Continuation of application No. 12/081,571, filed on Apr. 17, 2008, now Pat. No. 9,040,269, which is a continuation-in-part of application No. 11/816,847, filed as application No. PCT/EP2006/060154 on Feb. 21, 2006, now Pat. No. 8,895,287.

(30) Foreign Application Priority Data

Feb. 22, 2005 (GB) .................................. 0503657.9

(51) Int. Cl.
| | |
|---|---|
| *C12P 7/22* | (2006.01) |
| *C12N 1/00* | (2006.01) |
| *C07H 21/04* | (2006.01) |
| *C12P 23/00* | (2006.01) |
| *C12N 9/10* | (2006.01) |
| *C12N 9/02* | (2006.01) |
| *C12N 9/88* | (2006.01) |
| *C12N 9/00* | (2006.01) |
| *C12N 15/52* | (2006.01) |
| *C12P 7/42* | (2006.01) |
| *A23C 3/08* | (2006.01) |
| *A61K 31/05* | (2006.01) |

(52) U.S. Cl.
CPC .................. *C12P 7/22* (2013.01); *A23C 3/08* (2013.01); *A61K 31/05* (2013.01); *C12N 9/0042* (2013.01); *C12N 9/0073* (2013.01); *C12N 9/1029* (2013.01); *C12N 9/1037* (2013.01); *C12N 9/88* (2013.01); *C12N 9/93* (2013.01); *C12N 15/52* (2013.01); *C12P 7/42* (2013.01); *C12P 23/00* (2013.01); *C12Y 203/01074* (2013.01); *C12Y 106/02004* (2013.01); *C12Y 114/13011* (2013.01); *C12Y 403/01005* (2013.01); *C12Y 602/01012* (2013.01); *C12Y 604/01002* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,865,973 | A | 9/1989 | Kollerup et al. |
| 5,391,724 | A | 2/1995 | Kindl et al. |
| 5,500,367 | A | 3/1996 | Hain et al. |
| 5,973,230 | A | 10/1999 | Kindl et al. |
| 6,020,129 | A | 2/2000 | Schroder et al. |
| 6,284,523 | B1 | 9/2001 | Daugulis et al. |
| 6,521,748 | B2 | 2/2003 | Tang |
| 7,604,968 | B2 | 10/2009 | Schmidt-Dannert et al. |
| 8,343,739 | B2 | 1/2013 | Katz et al. |
| 8,518,677 | B2 | 8/2013 | Schmidt et al. |
| 8,569,024 | B2 | 10/2013 | Stenhuus et al. |

(Continued)

FOREIGN PATENT DOCUMENTS

| | | |
|---|---|---|
| CN | 1277954 | 12/2000 |
| EP | 0 309 862 | 4/1989 |

(Continued)

OTHER PUBLICATIONS

Pacher et al., "Antifungal stilbenoids from Stemona collinsae." J Nat Prod. 65 (6):820-827 (2002).

Pan et al., Identification of molecular pathways affected by pterostilbene, a natural dimethylether analog of resveratrol. BMC Med. Genomics. 2008:20:1-7.

Passorn et al., Heterologous expression of Mucor rouxii delta(12)-desaturase gene in *Saccharomyces cerevisiae*. Biochem. Biophys. Res. Commun. 263 (1):47-51 (1999).

(Continued)

*Primary Examiner* — Iqbal H Chowdhury
(74) *Attorney, Agent, or Firm* — McDonnell Boehnen Hulbert & Berghoff LLP

(57) ABSTRACT

A recombinant micro-organism producing resveratrol by a pathway in which phenylalanine ammonia lyase (PAL) produces trans-cinnamic acid from phenylalanine, cinnamate 4-hydroxylase (C4H) produces 4-coumaric acid from said trans-cinnamic acid, 4-coumarate-CoA ligase (4CL) produces 4-coumaroyl CoA from said 4-coumaric acid, and resveratrol synthase (VST) produces said resveratrol from said 4-coumaroyl CoA, or in which L-phenylalanine- or tyrosine-ammonia lyase (PAL/TAL) produces 4-coumaric acid, 4-coumarate-CoA ligase (4CL) produces 4-coumaroyl CoA from said 4-coumaric acid, and resveratrol synthase (VST) produces said resveratrol from said 4-coumaroyl CoA. The micro-organism may be a yeast, fungus or bacterium including *Saccharomyces cerevisiae, E. coli, Lactococcus lactis, Aspergillus niger*, or *Aspergillus oryzae*.

14 Claims, 10 Drawing Sheets

(56) References Cited

U.S. PATENT DOCUMENTS

| | | | |
|---|---|---|---|
| 8,895,287 | B2 | 11/2014 | Katz et al. |
| 9,040,269 | B2 * | 5/2015 | Katz .................... C12N 9/0042 |
| | | | 435/156 |
| 2001/0053847 | A1 | 12/2001 | Tang |
| 2004/0023357 | A1 | 2/2004 | Breinig |
| 2004/0059103 | A1 | 3/2004 | Huang |
| 2004/0078846 | A1 | 4/2004 | Desouza et al. |
| 2004/0229326 | A1 | 11/2004 | Ben-Bassat et al. |
| 2004/0234671 | A1 | 11/2004 | Ector et al. |
| 2005/0003474 | A1 | 1/2005 | Desouza et al. |
| 2005/0208643 | A1 | 9/2005 | Schmidt-Dannert et al. |
| 2006/0263864 | A1 | 11/2006 | Busby et al. |
| 2008/0286844 | A1 | 11/2008 | Katz et al. |
| 2009/0035839 | A1 | 2/2009 | Katz et al. |
| 2009/0082286 | A1 | 3/2009 | Huang et al. |
| 2011/0086399 | A1 | 4/2011 | Smits et al. |
| 2011/0124067 | A1 | 5/2011 | Stenhuus et al. |
| 2014/0024862 | A1 | 1/2014 | Katz et al. |

FOREIGN PATENT DOCUMENTS

| | | |
|---|---|---|
| EP | 0 464 461 | 1/1992 |
| EP | 0 533 010 | 3/1993 |
| EP | 1 510 586 | 3/2005 |
| EP | 1 715 032 | 10/2006 |
| JP | 2005-53862 | 3/2005 |
| JP | 2001-008695 | 1/2011 |
| KR | 2004-0105110 | 12/2004 |
| WO | WO 00/73485 | 12/2000 |
| WO | WO 02/10407 | 2/2002 |
| WO | WO 2004/049832 | 6/2004 |
| WO | WO 2004/092344 | 10/2004 |
| WO | WO 2005/012507 | 2/2005 |
| WO | WO 2005/118814 | 12/2005 |
| WO | WO 2006/055322 | 5/2006 |
| WO | WO 2006/089898 | 8/2006 |
| WO | WO 2006/111163 | 10/2006 |
| WO | WO 2006/124999 | 11/2006 |
| WO | WO 2006/125000 | 11/2006 |
| WO | WO 2007/034190 | 3/2007 |
| WO | WO 2008/009728 | 1/2008 |
| WO | WO 2009/016108 | 2/2009 |
| WO | WO 2009/124879 | 10/2009 |
| WO | WO 2009/124966 | 10/2009 |
| WO | WO 2009/124967 | 10/2009 |
| WO | WO 2011/140344 | 11/2011 |
| WO | WO 2011/147818 | 12/2011 |
| ZA | 20048194 | 10/2004 |

OTHER PUBLICATIONS

Pignede et al., "Autocloning and amplification of LIP2 in Yarrowia lipolytica." Appl. Environ Microbiol. 2000:66:3283-9.

Porter & Kasper, "NADPH-Cytochrome P-450 Oxidoreductase: Flavin Mononucleotide and Flavin Adenine Dinucleotide Domains Evolved from Different Flavoproteins", Biochemistry, 25:1682-1687 (1986).

Prather et al., "De novo biosynthetic pathways: rational design of microbial chemical factories. Current Opinion in Biotechnology." 19:468-474 (2008).

Preisig-Muller et al., "Characterization of a pine multigene family containing elicitor-responsive stilbene synthase genes". Plant Molecular Biology. 39(2):221-229. (1999).

Pretorius et al., "Meeting the consumer challenge through genetically customized wine-yeas strains," Trends Biotech 20:426-32 (2002).

Punt et al., "Filamentous fungi as cell factories for heterologous protein production," TRENDS in Biotechnology 20(5):200-206 (2002).

Raiber et al., "Molecular and enzymatic characterization of two stilbene synthases from Eastern white pine (Pinus strobus). A single Arg/His difference determines the activity and the pH dependence of the enzymes". FEBS Lett. 361 (2-3):299-302 (1995).

Richter & Wild, "Phenolic compounds in needles of Norway spruce trees in relation to novel forest decline: I. Studies on trees from site of the Northern Black Forest.", Biochem. Biophys. Pflanz 188, 305-320 (1992).

Ritter et al., "Structural Basis for the Entrance into the Phenylpropanoid Metabolism Catalyzed by Phenylalanine Ammonia-Lyase", The Plant Cell, 16(12):3426-3436 (Dec. 2004).

Ro et al. "Functional Characterization and Subcellular Localization of Poplar (Populus trichocarpa x Populus deltoides) Cinnamate 4-Hydroxylase." Plant Physiol. 126, 200t pp. 317-329 (2001).

Ro & Douglas, "Reconstitution of the Entry Point of Plant Phenylpropanoid Metabolism in Yeast (Saccharomyces cerevisiae)," J. Biol. Chem. 279(4):2600-07 (2004).

Rogers et al., The pleitropic drug ABC transporters from Saccharomyces cerevisiae. J Mol Microbiol Biotechnol. 2001:3:207-14.

Rosemann et al., "Biochemical Plant Responses to Ozone. II. Induction of Stilbene Biosynthesis in Scots Pine (Pinus sylvestris L) Seedlings. Jr." Plant Physiol. 97, 1280-1286 (1991).

Rosler et al. "Maize phenylalanine ammonia-lyase has tyrosine ammonia-lyase activity." Plant Physiol. 113, 1997. pp. 175-179 (1997).

Rother et al ., "An active site homology model of phenylalanine ammonia-lyase from Petroselinum crispum," Eur. J. Biochem. 269(12):3065-75 (2002).

Roupe et al., "Pharmacometrics of Stilbenes: Seguing Towards the Clinic." Curr. Clin. Pharmac. 1, 81-101 (2006).

Rupasinghe et al., "Common active site architecture and binding strategy of four phenylpropanoid P450s from Arabidopsis thaliana as revealsed by molecular modeling", Protein Engineering, 16(10):721-31 (2003).

Samappito et al. "Aromatic and pyrone polyketides synthesized by a stilbene synthase from Rheum tataricum" Phytochemistry, 62(3): Feb. 2003, pp. 313-323.

Schanz et al., "Stilbene synthase from Scot's pine (Pinus sylvestris)" FEBS Lett. 313(1):71-74 (1992).

Schoonbeek et al., "The ABC Transporter BcatrB Affects the Sensitivity of Botrytis cinerea to the Phytoalexin Resveratrol and the Fungicide Fenpiclonil," Molecular Plant-Microbe Interactions 14:562-71 (2001).

Schoppner & Kindl, "Purification and properties of a stilbene synthase from induced cell suspension cultures of peanut". J. Biol. Chem. 259, 6806-6811 (1984).

Schneider et al., "The substrate specificity-determining amino acid cod of 4-coumarate:CoA ligase", PNAS, vol. 100, No. 14, pp. 8601-8606, Jul. 2003.

Schroder et al., "Molecular analysis of resveratrol synthase. cDNA clones and relationship with chalcone synthase". Eur J Biochem 172(1): 161-69 (1988).

Schuster & Retey, "Serine-202 is the putative precursor of the active site dehydroalanine of phenylalanine ammonia lyase", FEBS Letters 349(2):252-54 (1994).

Schwede et al., "Crystal Structure of Histidine Ammonia-Lyase Revealing a Novel Polypeptide Modification as the Catalytic Electrophile", Biochemistry, 38(17):5355-61 (1999).

Sengottuvelan & Nalini, "Dietary supplementation of resveratrol suppresses colonic tumour incidence in 1,2-dimethylhydrazine-treated rats by modulating biotransforming enzymes and aberrant crypt foci development." British Journal of Nutrition 96(1):145-53 (2006).

Serazetdinova et al., "Expression of transgenic stilbene synthases in wheat causes the accumulation of unknown stilbene derivatives with antifungal activity." Journal of Plant Physiology 162(9):985-1002 (2005).

Servos et al., Gene SNQ2 of Saccharomyces cerevisiae, which confers resistance to 4-nitroquinoline-N-oxide and other chemicals, encodes a 169 kDa protein homologous to ATP-dependent permeases. Mol Gen Genet. Jan. 1993; 236(2-3):214-8.

Servos et al., A system of shuttle vectors and yeast host strains designed for efficient manipulation of DNA in Saccharomyces cerevisiae. Genetics. 1989:122:19-27.

(56) References Cited

OTHER PUBLICATIONS

Seshime et al., "Genomic evidences for the existence of a phenylpropanoid metabolic pathway in Aspergillus oryzue." Biochem. Biophys. Res Commun. 337(3):747-51 (2005).

Skinnider & Stoessl, "The effect of the phytoalexins, lubimin, (-)-maackiain, pinosylvin, and the related compounds dehydroloroglossol and hordatine M on human lymphoblastoid cell lines". Experientia 42(5):568-570 (1986).

Song et al., Engineering tolerance and accumulation of lead and cadmium in transgenic plants. Nat. Biotechnol. 2003:21:914-9.

Stark et al., "Novel Type of In Situ Extraction: Use of Solvent Containing Microcapsules for the Bioconversion of 2-Phenylethanol From .sub.L-Phenylalanine by *Saccharomyces cerevisiae*", Biotechnology and Bioengineering, vol. 83 (4), pp. 376-385, 2003.

Stojanovic et al., "Efficiency and mechanism of the anti-oxidant action of trans-resveratrol and its analogues in the radical liposome oxidation". Arch. Biochem. Biophys. 391(1):79-89 (2001).

STN Search CAS directory pinosylvin chemical properties data, pp. 1-2, 2012.

Stuible et al., "Identification of the Substrate Specificity-conferring Amino Acid Residues of 4-Coumarate:Coenzyme A Ligase Allows the Rational Design of Mutant Enzymes with New Catalytic Properties", The Journal of Biological Chemistry, vol. 276, No. 29, pp. 26893-26897, 2001.

Suga et al., "Endogenous pine wood nematicidal substances in pines, *Pinus massoniana, P. strobus* and *P. palustris*." Phytochemistry 33(6):1395-1401 (1993).

Suh et al., "Identification of amino acid residues important in the cyclization reactions of chalcone and stilbene synthases", Biochem. J. 350(Pt.1):229-35 (2000).

Tavares & Gunnarsson. GenBank GU593327.1 Mortierella alpina strain CBS 608.70 delta-6 elongase mRNA, complete cds. Mar. 29, 2010, one page.

Tilburn et al., "Transformation by integration in Aspergillus nidulans", Gene, vol. 26, pp. 205-221, 1983.

Trantas et al. "Metabolic engineering of the complete pathway leading to heterologous biosynthesis of various flavonoids and stilbenoids in *Saccharomyces cerevisiae*", Metab Eng. 11(6):355-66 (2009).

Tropf et al., "Reaction mechanisms of homodimeric plant polyketide synthase (stilbenes and chalcone synthase). A single active site for the condensing reaction is sufficient for synthesis of stilbenes, chalcones, and 6'-deoxychalcones". J. Biol. Chem. 270, 7922-7928 (1995).

Trott et al., Activation of heat shock and antioxidant responses by the natural product celastrol: transcriptional signatures of a thiol-targeted molecule. Mol Bioi Cell. 2008:19:1104-12.

Uhlmann & Ebel, "Molecular Cloning and Expression of 4-Coumarate:Coenzyme A Ligase, an Enzyme Involved in the Resistance Response of Soybean (*Glycine max* L.) against Pathogen Attack", Plant Physiol. 102(4):1147-56 (1993).

Uniprot, Accession No. P32178, ARO7 2010, www.uniprot.org. last accessed Jun. 8, 2015, pp. 1-7.

Uniprot, Accession No. P32449, ARO4, 2010, www.uniprot.org. last accessed Jun. 8, 2015, pp. 1-8.

Abe et al., "Enzymatic formation of long-chain polyketide pyrones by plant type III polyketide synthases", Phytochemistry, vol. 6, pp. 2447-2453 (2004).

Aggarwal et al., "Role of resveratrol in prevention and therapy of cancer: preclinical and clinical studies". Anticancer Res. 24(5A):2783-840 (2004).

Allina et al., "4-coumarate: Coenzyme A ligase in hybrid poplar. Properties of enzymes, cDNA cloning, and analysis of recombinant clones". Plant Physiol. 116, 743-754 (1998).

Andrade et al.. The ABC transporter AtrB from Aspergillus nidulans mediates resistance to all major classes of fungicides and some natural toxic compounds. Microbiology. 2000:146:1987-97.

Aoyama et al. "NADPH-cytochrome P-450 reductase of yeast microsomes." Arch. Biochem. Biophys. 185, 1978. pp. 362-369 (1978).

Appert et al., "Structural and catalytic properties of the four phenylalanine ammonia-lyase isoenzymes from parsley (*Petroselinum crispum* Nym.)" FEBS 225:491-99 (1994).

Aury et al., Global trends of whole-genome duplications revealed by the ciliate Paramecium tetraurelia. Nature. Nov. 9, 2006; 444(7116):171-8.

Austin et al., "An Aldol Switch Discovered in Stilbene Synthases Mediated Cyclization Specificity of Type III Polyketide Synthases", Chemistry & Biology, vol. 11, pp. 1179-1194, Sep. 2004.

Baedeker et al., "Autocatalytic Peptide Cyclization during Chain Folding of Histidine Ammonia-Lyase", Structure, vol. 10, pp. 61-67, Jan. 2002.

Baedeker et al., "Structures of two histidine ammonia-lyase modifications and implications for the catalytic mechanism", Eur. J. Biochem., vol. 269, pp. 1790-1797, 2002.

Banerjee et al., Responses of pathogenic and nonpathogenic yeast species to steroids reveal the functioning and evolution of multidrug resistance transcriptional networks. Eukaryot Cell. 2008:7:68-77.

Blanquet et al."Recombinant *Saccharomyces cerevisiae* Expressing P450 in Artificial Digestive Systems: a Model for Biodetoxication in the Human Digestive Environment." Applied and Environmental Microbiology, 69(5):2884-2892 (2003).

Boer et al., The genome-wide transcriptional responses of *Saccharomyces cerevisiae* grown on glucose in aerobic chemostat cultures limited for carbon, nitrogen, phosphorus, or sulfur. J Bioi. Chem. 2003:278:3265-74.

Caruso et al., "Structural basis for antioxidant activity of trans-resveratrol: ab initio calculations and crystal and molecular structure", J Agric Food Chem., vol. 52, pp. 7279-7285, 2004.

Celotti et al."Resveratrol content of some wines obtained from dried Valpolicella grapes: Recioto and Amarone." Journal of Chromatography A. 730(1-2):47-52 (1996).

Chen et al., "One-step transformation of the dimorphic yeast *Yarrowia lipolytica*." Appl Microbiol Biotechnol. 48(2):232-5 (1997).

Chloupkova et al., Expression of 25 human ABC transporters in the yeast *Pichia pastoris* and characterization of the purified ABCC3 ATPase activity. Biochemistry. 2007:46:7992-8003.

Cochrane, et al. "The *Arabidopsis phenylalanine* ammonia lyase gene family: kinetic characterization of the four PAL isoforms." Phytochemistry 65, 2004. pp. 1557-1564.

Connolly et al., Heterologous expression of a pleiotropic drug resistance transporter from Phytophthora sojae in yeast transporter mutants. Curr Genet. 2005:48:356-65.

Cordero-Otero et al., "Efficient selection of hygromycin-B-resistant Yarrowia lipolytica transformants". Appl Microbiol Biotechnol. 46(2):143-48 (1996).

Costa et al., "Characterization in vitro and in vivo of the putative multigene 4-coumarate:CoA ligase network in *Arabidopsis*: syringyl lignin and sinapate/sinapyl alcohol derivative formation", Phytochemistry, 66(17):2072-91 (2005).

Couzin, "Scientific community. Aging Research's Family Feud." Science 303(5662):1276-79 (2004).

Del Sorbo et al., Multidrug resistance in *Aspergillus nidulans* involves novel ATP-binding cassette transporters. Mol Gen Genet. 1997:254:417-26.

Del Sorbo et al., Cloning and functional characterization of BcatrA, a gene encoding an ABC transporter of the plant pathogenic fungus *Botryotinia fuckeliana (Botrytis cinerea).* Mycol Res. 2008:112:737-46.

Domergue et al., In vivo characterization of the first acyl-GoA Delta6-desaturase from a member of the plant kingdom, the microalga Ostreococcus tauri. Biochem J. Jul. 15, 2005; 389 (Pt 2):483-90.

Erdeniz et al., Cloning-Free PCR-Based Allele Replacement Methods. Genome Res. 1997 7: 1174-1183.

Etschmann et al., Biotechnological production of 2-phenylethanol. Appl Microbial Biotechnol 2002:59:1-8.

(56) References Cited

OTHER PUBLICATIONS

Fickers et al., "New disruption cassettes for rapid gene disruption and marker rescue in the yeast *Yarrowia lipolytica*." J Microbiol Methods. 55(3):727-37 (2003).
Filpula et al. "Nucleotide sequence of gene for phenylalanine ammonia-lyase from Rhodotorula rubra." Nucleic Acids Res. 16(23):11381 (1988).
Gehlert et al., "Stilbene synthase from seedlings of *Pinus sylvestris*—purification and induction in response to fungal infection". Mol. Plant-Microbe Interaction 3(6):444-49 (1990).
Gehm et al. "Resveratrol, a polyphenolic compound found in grapes and wine, is an agonist for the estrogen receptor." Proc. Natl. Acad. Sci. USA 94, 1997. pp. 14138-14143 (1997).
Gems et al., "An autonomously replicating plasmid transforms *Aspergillus nidulans* at high frequency". Gene 98 (1):61-67 (1991).
Giaever et al., Functional profiling of the *Saccharomyces cerevisiae* genome. Nature. 2002:418:387-91.
Gilon et al., Degradation signals for ubiquitin system proteolysis in *Saccharomyces cerevisiae*. The EMBO Journal. 1998:17:2759-2766.
Guengerich et al., Expression of human cytochrome P450 enzymes in yeast and bacteria and relevance to studies on catalytic specificity. Toxicology. 1993:82:21-37.
Urban et al., "Characterization of recombinant plant cinnarnate 4-hydroxylase produced in yeast. Kinetic and spectral properties of the major plant P450 of the phenylpropanoid pathway". Eur J Biochem. 222(3):843-50 (1994).
Urban et al. "Cloning, Yeast Expression, and Characterization of the Coupling of Two Distantly Related *Arabidopsis thaliana* NADPH-Cytochrome 450 Reductases with P450 CYP73A5." J. Biol. Chem. 272: 19176-186 (1997).
Vuralhan et al., "Physiological characterization of the ARO10-dependent broad-substrate-specificity 2-oxo acid decarboxylase activity of *Saccharomyces cerevisiae*," App. Env. Microbiol. 71:3276-84 (2005).
Wang et al., "Three-dimensional structure of NADPH-cytochrome P450 reductase: Prototype for FMN- and FAD-containing enzymes", Proc. Natl. Acad. Sci. USA, vol. 94, pp. 8411-8416, Aug. 1997.
Watts et al., "Discovery of a substrate selectivity switch in tyrosine ammonia-lyase, a member of the aromatic amino acid lyase family". Chem Biol. 13:1317-26 (2006).
Watts et al. "Exploring recombinant flavonoid biosynthesis in metabolically engineered *Escherichia coli*" Chembiochem: A European Journal of Chemical Biology 5(4): Apr. 2004, pp. 500-507.
Watts et al., "Biosynthesis of plant-specific stilbene polyketides in metabolically engineered *Escherichia coli*," BMC Biotechnology 6(22):1-12 (2006).
Werck-Reichhart & Feyereisen. Cytochromes P450: a success story. Genome Biology 2000:1:3003.1-3003.9.
Wiebe "Stable production of recombinant proteins in filamentous fungi-problems and improvements." Mycologist. 17:140-144 (2003).
Wiese et al., "Structural organization and differential expression of three stilbene synthase genes located on a 13 kb grapevine DNA fragment." Plant Mol Biol 26(2):667-77 (1994).
Yabusaki et al., "Primary Structure of *Saccharomyces cerevisiae* NADPH-Cytochrome P450 Reductase Deduced from Nucleotide Sequence of Its Cloned Gene", J. Biochem., 103(6):1004-10 (1988).
Yoon et al., CrelloxP-mediated in vivo excision of large segments from yeast genome and their amplification based on the 2 mm plasmid-derived system. Gene 1998:223:67-76.
Zwiers et al., ABC transporters and azole susceptibility in laboratory strains of the wheat pathogen *Mycosphaerella graminicola*. Antimicrob Agents Chemother. Dec. 2002; 46(12):3900-6.
The International Search Report issued in International Application No. PCT/EP2006/060154 (published as WO 2006/089898); dated Jun. 20, 2006, pp. 1-4.

The International Search Report issued in International Application No. PCT/EP2007/057484 (published as WO 2008/009728); dated Oct. 17, 2007, pp. 1-5.
The International Search Report issued in International Application No. PCT/EP2008/059768 (published as WO 2009/016108); dated Apr. 9, 2009, pp. 1-6.
The International Search Report issued in International Application No. PCT/EP2009/053974 (published as WO 2009/124879); dated Oct. 5, 2009, pp. 1-6.
The International Search Report issued in International Application No. PCT/EP2009/054219 (published as WO 2009/124967); dated Oct. 2, 2009, pp. 1-5.
The International Search Report issued in International Application No. PCT/EP2011/058447 (published as WO 2011/147818); dated Aug. 22, 2011, pp. 1-7.
Becker et al., "Metabolic engineering of *Saccharomyces cerevisiae* for the synthesis of the wine-related antioxidant resveratrol." FEMS Yeast Research 4:79-85 (2003).
Beekwilder et al., "Production of Resveratrol in Recombinant Microorganisms," Applied and Environmental Microbiology 72(8):5670-72 (2006).
Berner et al., "Genes and enzymes involved in caffeic acid biosynthesis in the actinomycete Saccharothrix espanaensis", J Bacteriol, 2006:188:2666-73.
Callemien et al., "Hop as an interesting source of resveratrol for brewers: Optimization of the extraction and quantitative study by liquid chromatography/atmospheric pressure chemical ionization tandem mass spectrometry" J Agric Food Chem. 53(2):424-29 (2005).
Ehlting et al., Three 4-coumarate:coenzyme A ligases in *Arabidopsis thaliana* represent two evolutionarily divergent classes in angiosperms. Plant J. 1999:19:9-20.
Gietz & Schiestl. Applications of high efficiency lithium acetate transformation of intact yeast cells using single-stranded nucleic acids as carrier. Yeast. 1991:7:253-63.
Gonzalez-Candelas et al. "The use of transgenic yeasts expressing a gene encoding a glycosyl-hydrolase as a tool to increase resveratrol content in wine." Int J Food Microbiol. 59(3):179-83 (2000).
Hain et al., "Disease resistance results from foreign phytoalexin expression in a novel plant", Nature, vol. 361, pp. 153-156, 1993.
Hamberger & Hahlbrock. The 4-coumarate:CoA ligase gene family in *Arabidopsis thaliana* comprises one rare, sinapate-activating and three commonly occurring isoenzymes. Proc Natl Acad Sci USA. 2004:101:2209-14.vol. 101, pp. 2209-2214, 2004.
Mizutani et al., Isolation of a eDNA and a genomic clone encoding cinnamate 4-hydroxylase from *Arabidopsis* and its expression manner in planta. Plant Physiol. 1997:113:755-63.
Mizutani & Ohta. Two isoforms of NADPH:cytochrome P450 reductase in *Arabidopsis thaliana*. Gene structure. heterologous expression in insect cells. and differential regulation. Plant Physiol. 1998:116:357-67.
Mumberg et al., Yeast vectors for the controlled expression of heterologous proteins in different genetic backgrounds. Gene. 156(1):119-22 (Apr. 1995).
Sikorski & Hieter, "A system of shuttle vectors and yeast host strains designed for efficient manipulation of DNA in *Saccharomyces cerevisiae*", Genetics, vol. 122(1):19-27 (May 1989).
Verduyn et al., "Effect of benzoic acid on metabolic fluxes in yeasts: a continuous-culture study on the regulation of respiration and alcoholic fermentation". Yeast. 8, 501-517 (1992).
Whisstock et al., "Prediction of protein function from protein sequence and structure", Quarterly Reviews of Biophysics 36(3): 307-340 (2003).
Guerra et al., "A novel system of genetic transformation allows multiple integrations of a desired gene in *Saccharomyces cerevisiae* chromosomes", J Microbiol Methods, vol. 67, pp. 437-445, 2006.
Hall, "Longevity research. In Vino Vitalis? Compounds Activate Life-Extending Genes." Science 301(5637):1165 (2003).
Hart, "Role of phytostilbenes in decay and disease resistance". Annu. Rev. Phytopathology 19, 437-458 (1981).
Hart & Shrimpton, "Role of stilbenes in resistance of wood to decay". Phytopathology 69, 1138-1143 (1979).

(56) References Cited

OTHER PUBLICATIONS

Hasemann et al., "Structure and function of cytochromes P450:a comparative analysis of three crystal structures", Structure, 3(1):41-62 (Jan. 1995). PMID: 7743131.
Hemingway et al., "Polyphenols in Ceratocystis minor infected Pinus taeda: Fungal Metabolites, phloem and xylem phenols". J. Agric. Food Chem., 25, 717-722 (1977).
Herrero et al., Engineering the *Saccharomyces cerevisiae* isoprenoid pathway for de novo production of aromatic monoterpenes in wine, Metabolic Eng., 10(2):78-86 (2008).
Horinouchi et al., "Combinatorial Biosynthesis of Non-bacterial and Unnatural Flavonoids, Stilbenoids and Curcuminoids by Microorganisms," Journal of Antibiotics 61(12):709-28 (2008).
Huang, "Diet for cancer prevention." Food Sci.(Shipin Kexue; Taipei) 24(6):713-727 (1997).
Hubbard et al., "NADPH-Cytochrome P450 Oxidoreductase: Structural Basis for Hydride and Electron Transfer." J. Biol. Chem. 276:29163-70 (2001).
Hwang et al., "Production of Plant-Specific Flavanones by *Escherichia coli* Containing an Artificial Gene Cluster." Appl. Environ. Microbial. 69(5):2699-2706 (2003).
Jang et al. "Cancer Chemopreventive Activity of Resveratrol, a Natural Product Derived from Grapes." Science 275 (5297):218-20 (1997).
Jeandet et al. "Effect of Enological Practices on the Resveratrol Isomer Content of Wine." J. Agric. Food Chem. 43, 1995. pp. 316-319 (1995).
Jeandet et al. "Occurence of a resveratrol.cndot.- D-glucoside in wine: Preliminary studies." Vitis 33, pp. 183-184 (1994).
Jeandet et al., "Phytoalexins from the Vitaeae: Biosynthesis, Phytoalexin Gene Expression in Transgenic Plants, Antifungal Activity, and Metabolism", J. Agric. Food Chem., 50(10):2731-41 (2002).
Jiang et al. "Metabolic Engineering of the Phenylpropanoid Pathway in *Saccharomyces cerevisiae*." Applied and Environmental Microbiology 71(6):2962-69 (2005).
Johansson & Hahn-Hagerdal. Overproduction of pentose phosphate pathway enzymes using a new CRE-IoxP expression vector for repeated genomic integration in *Saccharomyces cerevisiae*. Yeast 2002:19:225-231.
Jungwirth & Kuchler. Yeast ABC transporters—a tale of sex, stress, drugs and aging. FEBS Lett. 2006:580:1131-8.
Juretzek et al., "Vectors for gene expression and amplification in the yeast *Yarrowia lipolytica*", Yeast. 18(2):97-113 (2001).
Juvvadi et al., "Genomics reveals traces of fungal phenylpropanoid-flavonoid metabolic pathway in the filamentous fungus *Aspergillus oryzae*." J Microbiol. 43(6):475-486 (2005).
Kaneko, et al., "Cinnamate:Coenzyme A ligase from the Filamentous Bacteria *Streptomyces coelicolor*A3(2)," J. Bact. 185(1): 20-27 (2003).
Kindl, Biosynthesis of stilbenes. In Higuchi T, ed, Biosynthesis and Biodegradation of Wood Components. Academic Press, London, pp. 349-377. (1985).
Kizer et al., "Application of Functional Genomics to Pathway Optimization for Increased Isoprenoid Production." Applied and Environmental Microbiology. 74(10):3229-3241 (2008).
Koopmann et al. "Regulation and Functional Expression of Cinnamate 4-Hydroxylase from Parsley." Plant Physiol. 119(1):49-56 (1999).
Kopp, "Resveratrol, a phytooestrogen found in red wine. A possible explanation for the conundrum of the "French Paradox"?" Eur. J. Endocrinol. 138, 1998. pp. 619-620.
Kodan et al., "A stilbene synthase from Japanese red pine (*Pinus densiflora*): Implications for phytoalexin accumulationand downregulation of flavonoid biosynthesis". Proc. Natl. Acad. Sci. 99, 3335-3339 (2002).
Kunji et al., Lactococcus lactis as host for overproduction of functional membrane proteins. Biochim Biophys Acta. 2003:1610:97-108.

Kyndt et al. "Characterization of a bacterial tyrosine ammonia lyase, a biosynthetic enzyme for the photoactive yellow protein." FEBS Lett. 512(1-3):240-44 (2002).
La Grange et al. "Cloning of the Bacillus pumilus beta-xylosidase gene (xynB) and its expression in *Saccharomyces cerevisiae*. Appl. Microbiol." Biotechnol. 47(3):262-266 (1997).
Le Dall et al., "Multiple-copy integration in the yeast *Yarrowia lipolytica*". Curr Genet. 26(1):38-44 (1994).
Lee et al. "Antibacterial and antifungal activity of pinosylvin, a constituent of pine" Fitoterapia, 76(2):258-60 (2005).
Lieutier et al., "Changes in phenolic metabolites of Scots pine phloem induced by Ophiostoma brunneo-ciliatum, a bark beetle-associated fungus". Eur. J.For Pathol. 26(3):145-158 (1996).
Lin et al. "Sequence and analysis of chromosome 2 of the plant *Arabidopsis thaliana*." Nature 402(6763):761-768 (1999).
Lindberg et al., "Antibacterial effects of knotwood extractives on paper mill bacteria". J Ind Microbiol Biotechnol. 31 (3):137-147 (2004).
Lobo, "Benefits and risks of estrogen replacement therapy." Am. J. Obstet. Gynecol. 173(3 Pt 2):982-89 (1995).
Luttik et al., "Alleviation of feedback inhibition in *Saccharomyces cerevisiae* aromatic amino acid biosynthesis: Quantification of metabolic impact," Metabolic Eng. 10:141-53 (2008).
Madzak et al., "Heterologous protein expression and secretion in the non-conventional yeast *Yarrowia lipolytica*: a review". J Biotechnol. 109(1-2):63-81 (2004).
Martin et al., "Engineering a mevalonate pathway in *Escherichia coli* for production of terpenoids". Nature biotechnology 21(7):796-802 (2003).
Melchior & Kindl, "Coordinate and elicitor dependent expression of stilbene synthase and phenylalanine ammonialyase genes in Vitis cv. Optima." Arch. Biochem. Biophys 288(2):552-57 (1991).
Melchior & Kindl, "Grapevine stilbene synthase cDNA only slightly differing from chalcone synthase cDNA is expressed in *Escherichia coli* into a catalytically active enzyme", FEBS Lett. 268(1):17-20 (Jul. 1990).
Mellanen et al., "Wood-derived estrogens: studies in vitro with breast cancer cell lines and in vivo in trout". Toxicol. App. Pharm. 136(2):381-88 (1996).
Merkulov et al., "Cloning and characterization of the Yarrowia lipolytica squalene synthase (SQSI) gene and functional complementation of the *Saccharomyces cerevisiae* erg9 mutation," Yeast 16(3):197-206 (2000).
Morita et al., "Novel polyketides synthesized with a higher plant stilbene synthase". Eur. J. Biochem. 268, 3759-3766 (2001).
Moriya et al.. In vivo robustness analysis of cell division cycle genes in *Saccharomyces cerevisiae*. PLoS Genet. Jul. 2006; 2(7):e111. Epub Jun. 5, 2006 Erratum in: PLoS Genet. Dec. 2006; 2(12):e218.
Muhitch et al.. Transgenic expression of the TRI101 or PDR5 gene increases resistance of tobacco to the phytotoxic effects of the trichothecene 4, 15-diacetoxyscirpenol. Plant Sci. 2000:157:201-207.
Muller et al., "Comparison of expression systems in the yeasts *Saccharomyces cerevisiae*, Hansenula polymorpha, Klyveromyces lactis, Schizosaccharomyces pombe and Yarrowia lipolytica". Cloning of two novel promoters from Yarrowia lipolytica". Yeast 14(14):1267-83 (1998).
Mumberg et al., Yeast vectors for the controlled expression of heterologous proteins in different genetic backgrounds. Gene. 1995:156:119-22.
Nicaud et al., Protein expression and secretion in the yeast *Yarrowia lipolytica*. FEMS Yeast Res. 2(3):371-9 (2002).
Niimi et al., Functional analysis of fungal drug efflux transporters by heterologous expression inS. cerevisiae. Jpn. J. Infect Disease 2005:58:1-7.
Nisimoto, "Localization Cytochrome c-binding Domain on NADPH-Cytochrome P-450 Reductase", The Journal of Biological Chemistry, vol. 261, No. 30, pp. 14232-14239, 1986.
Zahir et al., "Isolation and characterization of novel organic solvent-tolerant bacteria" Extremophiles 10(2):129-38 2006; Epub Oct. 20, 2005).

(56) References Cited

OTHER PUBLICATIONS

Bateman et al., "Pfam 3.1: 1313 multiple alignments and profile HMMs match the majority of proteins." Nucl. Acids Res., 27(1):260-62 (Jan. 1999).
Bu et al., "High-throughput Caco-2 cell permeability screening by cassette dosing and sample pooling approaches using direct injection/on-line guard cartridge extraction/tandem mass spectrometry," Rapid Communications in Mass Spectrometry 14(6):523-28 (Mar. 2000).
Chenna et al., "Multiple sequence alignment with the Clustal series of programs." Nucl. Acids Res., 31(13):3497-500 (Jul. 2003).
Decendit et al., "Galloylated catechins and stilbene diglucosides in Vitis vinifera cell suspension cultures" Phytochemistry 60(8):795-98 (Aug. 2002).
Escribano-Bailon et al., "Coupling Reactions between Flavylium Ions and Catechin" Phytochemistry 41 (6):1583-92 (1996).
Gao & Ming, "Bioavailability challenges associated with development of anti-cancer phenolics." Mini Rev Med Chem 10(6):550-67 (Jun. 2010).
Gustafsson et al., "Codon bias and heterologous protein expression," Trends Biotechnol. 22:346-53 (2004).
Hano et al., "Sequential glucosylation determined by NMR in the biosynthesis of mulberroside D, a cis-oxyresveratrol diglucoside, in *Morus alba* L cell cultures," Cell. Mol. Life Sci. 53(3):237-41 (Mar. 1997).
Hansen et al., "Substrate specificities of family 1 UGTs gained by domain swapping." Phytochemistry 70(4):473-82 (Mar. 2009; Epub Mar. 2, 2009).
Horinouchi et al., "Combinatorial biosynthesis of plant medicinal polyketides by microorganisms" Current Opinion in Chemical Biology 13(2):197-2014 (Apr. 2009).
Kapetanovic et al., "Pharmacokinetics, oral bioavailability, and metabolic profile of resveratrol and its dimethylether analog, pterostilbene, in rats." Cancer Chemother Pharmacol 68(3):593-601 (Sep. 2011; Epub Nov. 30, 2010).
Kirino et al., "Analysis and functionality of major polyphenolic components of Polygonum cuspidatum (itadori)." J Nutr Sci Vitaminol 58(4):278-86 (2012).
Koopman et al., "De novo production of the flavonoid naringenin in engineered *Saccharomyces cerevisiae*." Microb Cell Fact. 11:155 pp. 1-15 (Dec. 2012).
Larronde et al., "New stilbenoid glucosides isolated from Vitis vinifera cell suspension cultures (cv. Cabernet Sauvignon)" Planta Med. 71(9):888-90 (Sep. 2005).
Li et al., "De novo production of resveratrol from glucose or ethanol by engineered *Saccharomyces cerevisiae*." 32:1-11 (Nov. 2015; Epub Sep. 4, 2015).
Mora-Pale et al., "Metabolic engineering and in vitro biosynthesis of phytochemicals and non-natural analogues". Plant Science 210:10-24 (May 2013).
Orsini et al., "Isolation, synthesis, and antiplatelet aggregation activity of resveratrol 3-O-beta-D-glucopyranoside and related compounds." J. Nat. Prod. 60(11):1082-87 (Nov. 1997).
Osmani et al., "Catalytic key amino acids and UDP-sugar donor specificity of a plant glucuronosyltransferase, UGT94B1: molecular modeling substantiated by site-specific mutagenesis and biochemical analyses." Plant Physiol. 148(3):1295-1308 (Nov. 2008; Epub Oct. 1, 2008).
Ozaki et al., "Regioselective glucosidation of-resveratrol inexpressing glucosyltransferase from Phytolacca americana" Biotechnology Letters 34(3):475-81 (Nov. 2011).
Park et al., "Bioconversion of Piceid to Piceid Glucoside Using Amylosucrase from Alteromonas macleodii Deep Ecotype," J. Microbiol. Biotechnol. 22(12):1698-1704 (Dec. 2012).
Park et al., "Enzymatic synthesis of piceid glucosides using maltosyltransferase from Caldicellulosiruptor bescii DSM 6725" J. Agric. Food Chem. 60(33):8183-89 (Aug. 2012; Epub Aug. 8, 2012).
Regev-Shoshani et al., "Glycosylation of resveratrol protects it from enzymic oxidation." Biochem J. 374(Pt 1):157-63 (Aug. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis." J Biol Chem. 280(2):899-906 (Jan. 2005; Epub Oct. 7, 2004).
Schmidheini et al., "A single point mutation results in a constitutively activated and feedback-resistant chorismate mutase of *Saccharomyces cerevisiae*." 171(3):1245-53 (Mar. 1989).
Schmidlin et al., "A stress-inducible resveratrol O-methyltransferase involved in the biosynthesis of pterostilbene in grapevine." Plant Physiol 148(3):1630-39 (Nov. 2008; Epub Sep. 17, 2008).
Shao et al., "Phenolic and Triterpenoid glycosides from Aster batangensis" Phytochemistry 41(6):1593-98 (1996).
Shi et al., "Improving production of malonyl coenzyme A-derived metabolites by abolishing Snf1-dependent regulation of Acc1." 6(3):e01130-14 (May 2014).
Sonnhammer et al., "Pfam: multiple sequence alignments and HMM-profiles of protein domains." Nucl. Acids Res. 26(1):320-22 (Jan. 1998).
Sonnhammer et al., "Pfam: a comprehensive database of protein domain families based on seed alignments" Proteins, 28(3):405-20 (Jul. 1997).
Sun et al., "In vitro testing of drug absorption for drug 'developability' assessment: forming an interface between in 'in vitro preclinical data and clinical outcome." Curr. Opin. Drug Discov. Devel. 7(1):75-85 (Jan. 2004).
Waffo-Teguo et al., "Isolation, identification, and antioxidant activity of three stilbene glucosides newly extracted from vitis vinifera cell cultures" J. Nat. Prod. 61(5):655-57 (May 1998).
Wang et al., "Pterostilbene production by microorganisms expressing resveratrol O-methyltransferase." Ann Microbiol. pp. 1-10 (published online: Jun. 26, 2014).
Wang et al., "Structure, mechanism and engineering of plant natural product glycosyltransferases" FEBS Letters 583(20):3303-09 (Oct. 2009).
Weis et al., "Regioselective glucosylation of aromatic compounds: screening of a recombinant glycosyltransferase library to identify biocatalysts." Angew. Chem. Int. Ed. 45(21): 3534-38 (May 2006).
Yeo et al., "Quantification of pinosylvin in rat plasma by liquid chromatography-tandem mass spectrometry: application to a preclinical pharmacokinetic study" J Chromatogr B Analyt Technol Biomed Life Sci. 931:68-74 (Jul. 2013; Epub May 28, 2013).
Yeo et al., "Pharmacokinetics of pterostilbene in Sprague-Dawley rats: the impacts of aqueous solubility, fasting, dose escalation, and dosing route on bioavailability." Mol Nutr Food Res 57(6):1015-25 (Jun. 2013; Epub Feb. 13, 2013). PMID: 23417986.
Katsuyama et al., "Precursor-directed biosynthesis of stilbene methyl ethers in *Escherichia coli*" Biotechnology Journal 2(10):1286-93 (Oct. 2007).
Zhou et al., "Inhibition of xanthine and monoamine oxidases by stilbenoids from Veratrum taliense." Planta Med. 67(2)158-61 (Mar. 2001).
Zhou et al., "Assessing the regioselectivity of OleD-catalyzed glycosylation with a diverse set of acceptors." J. Nat. Prod. 76(2):279-86 (Feb. 2013; Epub Jan. 29, 2013).
The International Search Report issued in International Application No. PCT/EP2014/067520 (published as WO 2015/028324); dated Mar. 2, 2015, pp. 1-9.
Rodriguez et al., "Establishment of a yeast platform strain for production of p-coumaric acid through metabolic engineering of aromatic amino acid biosynthesis." Metab. Eng. 31:181-88 (Sep. 2015; Epub Aug. 18, 2015).

* cited by examiner

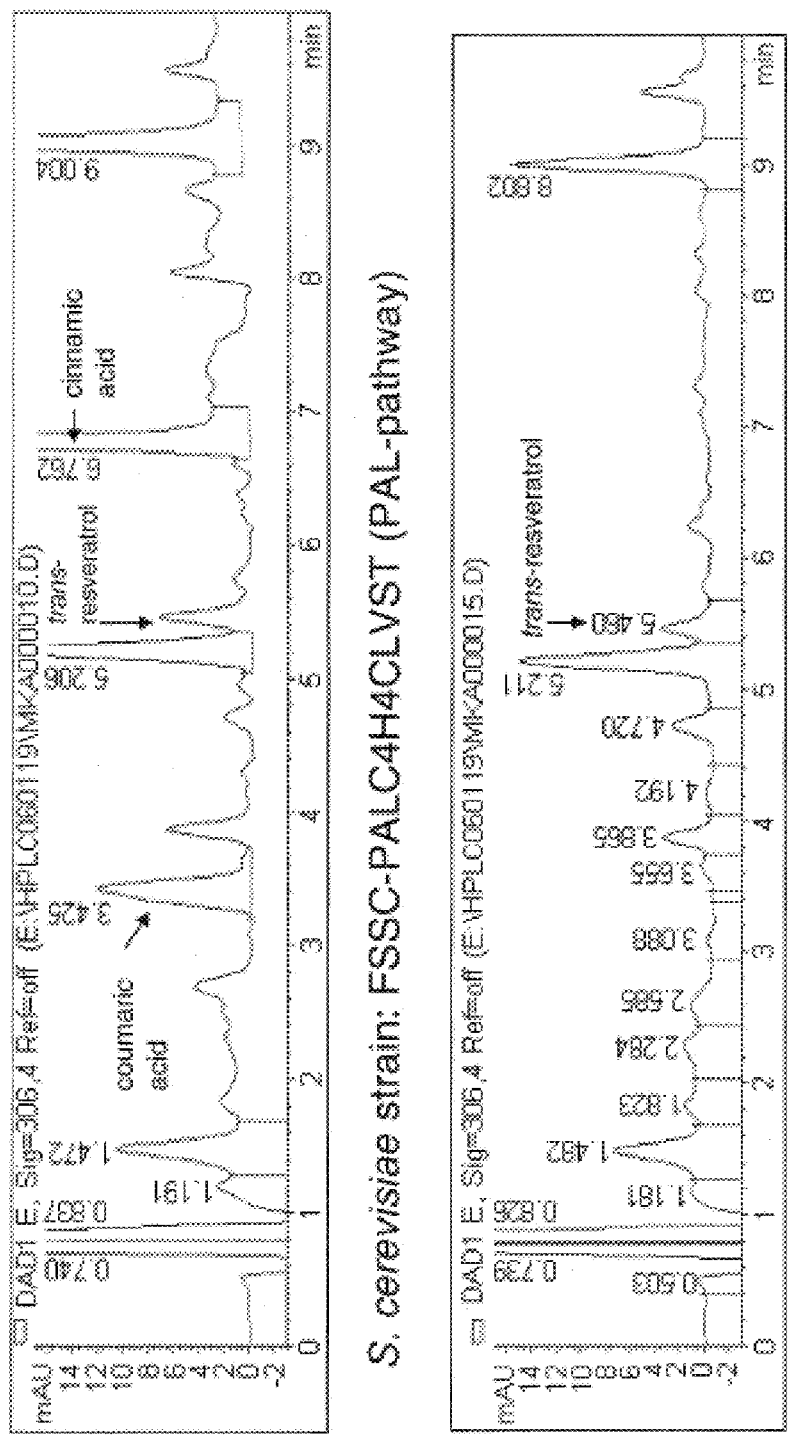
Figure 4 Contd

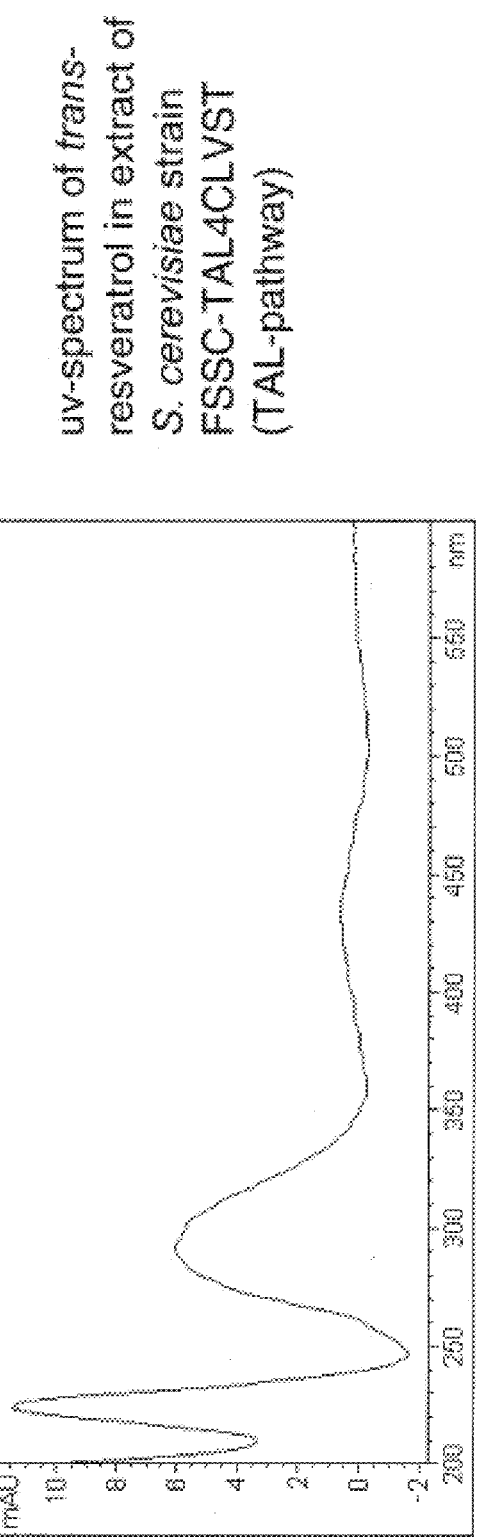
Figure 5 contd

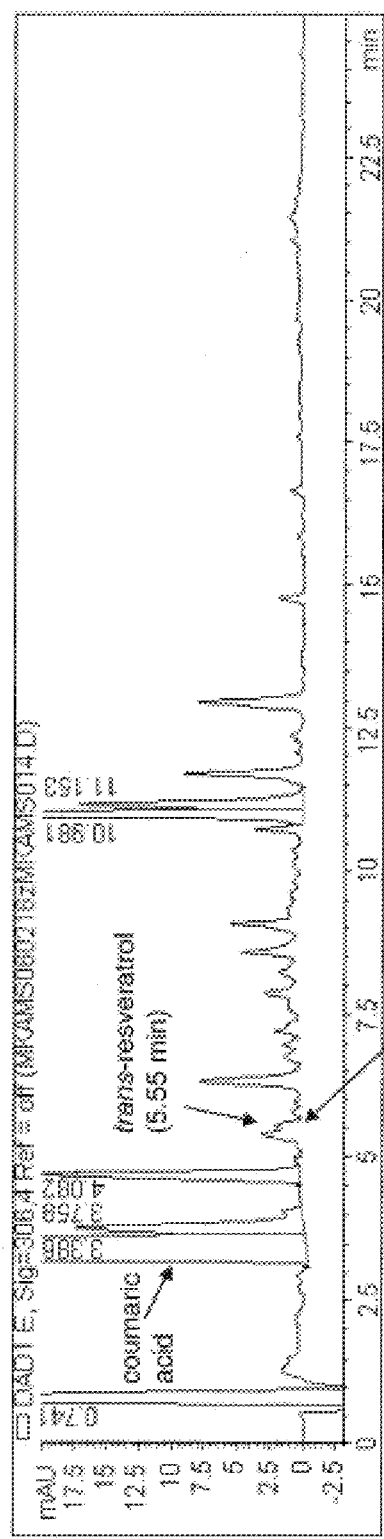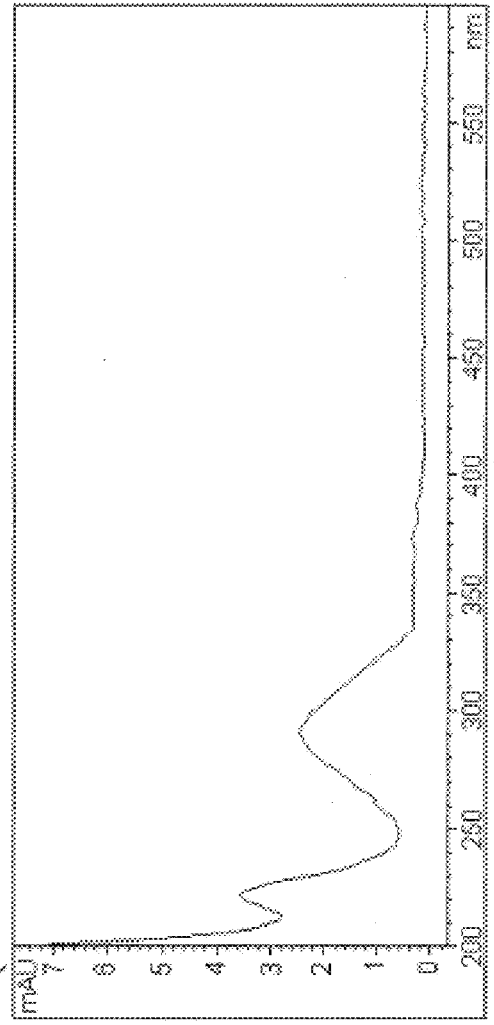
Figure 7 contd

SEQUENCE LISTING

```
<160> NUMBER OF SEQ ID NOS: 64

<210> SEQ ID NO 1
<211> LENGTH: 2154
<212> TYPE: DNA
<213> ORGANISM: Arabidopsis thaliana

<400> SEQUENCE: 1
atggatcaaa tcgaagcaat gttgtgcggc ggaggagaga agacaaaagt ggcggttact      60
acgaagactt tggcagatcc attgaattgg ggtttagcag cggatcaaat gaaaggaagt     120
catttagatg aagtgaagaa gatggtcgaa gagtatcgta gaccagtcgt gaatcttggc     180
ggagaaacac tgacgatcgg acaagttgct gccatctcca ccgtaggagg cagcgttaag     240
gttgagttag cggagacttc aagagccggt gtgaaagcta gcagtgattg ggttatggag     300
agcatgaaca aaggtactga cagttacgga gtcaccaccg gctttggtgc tacttctcac     360
cggagaacca aaaacggcac cgcattacaa acagaactca ttagattttt gaacgccgga     420
atattcggaa acacgaagga gacatgtcac acactgccgc aatccgccac aagagccgcc     480
atgctcgtca gagtcaacac tcttctccaa ggatactccg gatccgatt cgagatcctc     540 gaagcgatta caagtctcct caaccacaac atctctccgt cactacctct ccgtggaacc     600
attaccgcct ccggcgatct cgttcctctc tcttacatcg ccggacttct caccggccgt     660
cctaattcca aagccaccgg tcccgacggt gaatcgctaa ccgcgaaaga gcttttgag     720 aaagccgaa tcagtactgg attcttcgat ttacaaccta aggaaggttt agctctcgtt     780
aatggcacgg cggttggatc tggaatggcg tcgatggttc tattcgaagc gaatgtccaa     840
gcggtgttag cggaggtttt atcagcgatc ttcgcggagg ttatgagcgg gaaacctgag     900
tttaccgatc atctgactca tcgtttaaaa catcatcccg gacaaatcga agcggcggcg     960
ataatggagc acatactcga cggaagctca tacatgaaat tagctcaaaa ggttcacgag    1020
atggatccat gcagaaacc aaaacaagat cgttacgctc ttcgtacatc tcctcaatgg    1080
ctaggtcctc aaattgaagt aatccgtcaa gctacgaaat cgatagagcg tgaaatcaac    1140
```

-continued

```
tccgttaacg ataatccgtt gatcgatgtt tcgaggaaca aggcgattca cggtggtaac    1200
ttccaaggaa caccaatcgg agtttctatg gataacacga gattggcgat tgctgcgatt    1260
gggaagctaa tgtttgctca attctctgag cttgttaatg atttctacaa caatggactt    1320
ccttcgaatc taactgcttc gagtaatcca agtttggatt atggattcaa aggagcagag    1380
attgctatgg cttcttattg ttctgagctt caatacttgg ctaatccagt cacaagccat    1440
gttcaatcag ctgagcaaca taatcaagat gtgaactctc ttggtttgat ctcgtctcgt    1500
aaaacatctg aagctgtgga tattcttaag ctaatgtcaa caacgttcct tgtggggata    1560
tgtcaagctg ttgatttgag acatttggag gagaatctga caaaactgt gaagaacaca    1620 gtttctcaag ttgctaagaa agtgttaacc actggaatca acggtgagtt acatccgtca    1680
aggttttgcg agaaggactt gcttaaggtt gttgatcgtg agcaagtgtt cacgtatgtg    1740
gatgatcctt gtagcgctac gtaccgttg atgcagagac taagacaagt tattgttgat    1800
cacgctttgt ccaacggtga gactgagaag aatgcagtga cttcgatctt tcaaaagatt    1860
ggagcttttg aagaggagct taaggctgtg cttccaaagg aagttgaagc ggctagagcg    1920
gcttatggga atggaactgc gccgattcct aaccggatta aggaatgtag gtcgtatccg    1980
ttgtataggt tcgtgaggga agagcttgga acgaagttgt tgactggaga aaaggttgtg    2040
tctccgggag aggagtttga taaggtcttc actgctatgt gtgaaggtaa acttattgat    2100
ccgttgatgg attgtctcaa ggaatggaac ggagctccga ttccgatttg ctaa          2154
```

<210> SEQ ID NO 2
<211> LENGTH: 717
<212> TYPE: PRT
<213> ORGANISM: Arabidopsis thaliana

<400> SEQUENCE: 2

```
Met Asp Gln Ile Glu Ala Met Leu Cys Gly Gly Gly Glu Lys Thr Lys
1               5                   10                  15

Val Ala Val Thr Thr Lys Thr Leu Ala Asp Pro Leu Asn Trp Gly Leu
            20                  25                  30

Ala Ala Asp Gln Met Lys Gly Ser His Leu Asp Glu Val Lys Lys Met
        35                  40                  45

Val Glu Glu Tyr Arg Arg Pro Val Val Asn Leu Gly Gly Glu Thr Leu
    50                  55                  60

Thr Ile Gly Gln Val Ala Ala Ile Ser Thr Val Gly Gly Ser Val Lys
65                  70                  75                  80

Val Glu Leu Ala Glu Thr Ser Arg Ala Gly Val Lys Ala Ser Ser Asp
                85                  90                  95

Trp Val Met Glu Ser Met Asn Lys Gly Thr Asp Ser Tyr Gly Val Thr
            100                 105                 110

Thr Gly Phe Gly Ala Thr Ser His Arg Arg Thr Lys Asn Gly Thr Ala
        115                 120                 125

Leu Gln Thr Glu Leu Ile Arg Phe Leu Asn Ala Gly Ile Phe Gly Asn
    130                 135                 140

Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
                165                 170                 175

Phe Glu Ile Leu Glu Ala Ile Thr Ser Leu Leu Asn His Asn Ile Ser
            180                 185                 190

Pro Ser Leu Pro Leu Arg Gly Thr Ile Thr Ala Ser Gly Asp Leu Val
```

```
            195                 200                 205
Pro Leu Ser Tyr Ile Ala Gly Leu Leu Thr Gly Arg Pro Asn Ser Lys
    210                 215                 220

Ala Thr Gly Pro Asp Gly Glu Ser Leu Thr Ala Lys Glu Ala Phe Glu
225                 230                 235                 240

Lys Ala Gly Ile Ser Thr Gly Phe Phe Asp Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
        275                 280                 285

Ala Ile Phe Ala Glu Val Met Ser Gly Lys Pro Glu Phe Thr Asp His
    290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
                325                 330                 335

Lys Val His Glu Met Asp Pro Leu Gln Lys Pro Lys Gln Asp Arg Tyr
            340                 345                 350

Ala Leu Arg Thr Ser Pro Gln Trp Leu Gly Pro Gln Ile Glu Val Ile
        355                 360                 365

Arg Gln Ala Thr Lys Ser Ile Glu Arg Glu Ile Asn Ser Val Asn Asp
    370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
                405                 410                 415

Ile Ala Ala Ile Gly Lys Leu Met Phe Ala Gln Phe Ser Glu Leu Val
            420                 425                 430

Asn Asp Phe Tyr Asn Asn Gly Leu Pro Ser Asn Leu Thr Ala Ser Ser
        435                 440                 445

Asn Pro Ser Leu Asp Tyr Gly Phe Lys Gly Ala Glu Ile Ala Met Ala
    450                 455                 460

Ser Tyr Cys Ser Glu Leu Gln Tyr Leu Ala Asn Pro Val Thr Ser His
465                 470                 475                 480

Val Gln Ser Ala Glu Gln His Asn Gln Asp Val Asn Ser Leu Gly Leu
                485                 490                 495

Ile Ser Ser Arg Lys Thr Ser Glu Ala Val Asp Ile Leu Lys Leu Met
            500                 505                 510

Ser Thr Thr Phe Leu Val Gly Ile Cys Gln Ala Val Asp Leu Arg His
        515                 520                 525

Leu Glu Glu Asn Leu Arg Gln Thr Val Lys Asn Thr Val Ser Gln Val
    530                 535                 540

Ala Lys Lys Val Leu Thr Thr Gly Ile Asn Gly Glu Leu His Pro Ser
545                 550                 555                 560

Arg Phe Cys Glu Lys Asp Leu Leu Lys Val Val Asp Arg Glu Gln Val
                565                 570                 575

Phe Thr Tyr Val Asp Asp Pro Cys Ser Ala Thr Tyr Pro Leu Met Gln
            580                 585                 590

Arg Leu Arg Gln Val Ile Val Asp His Ala Leu Ser Asn Gly Glu Thr
        595                 600                 605

Glu Lys Asn Ala Val Thr Ser Ile Phe Gln Lys Ile Gly Ala Phe Glu
    610                 615                 620
```

```
Glu Leu Lys Ala Val Leu Pro Lys Glu Val Ala Ala Arg Ala
625                 630                 635                 640

Ala Tyr Gly Asn Gly Thr Ala Pro Ile Pro Asn Arg Ile Lys Glu Cys
                645                 650                 655

Arg Ser Tyr Pro Leu Tyr Arg Phe Val Arg Glu Glu Leu Gly Thr Lys
                660                 665                 670

Leu Leu Thr Gly Glu Lys Val Val Ser Pro Gly Glu Glu Phe Asp Lys
                675                 680                 685

Val Phe Thr Ala Met Cys Glu Gly Lys Leu Ile Asp Pro Leu Met Asp
    690                 695                 700

Cys Leu Lys Glu Trp Asn Gly Ala Pro Ile Pro Ile Cys
705                 710                 715
```

<210> SEQ ID NO 3
<211> LENGTH: 1518
<212> TYPE: DNA
<213> ORGANISM: Arabidopsis thaliana

<400> SEQUENCE: 3

```
atggacctcc tcttgctgga gaagtcttta atcgccgtct tcgtggcggt gattctcgcc      60
acggtgattt caaagctccg cggcaagaaa ttgaagctac ctccaggtcc tataccaatt     120
ccgatcttcg gaaactggct tcaagtcgga gatgatctca ccaccgtaa tctcgtcgat     180
tacgctaaga attcggcga tctcttcctc ctccgtatgg gtcagcgaaa cctagtcgtc     240
gtctcctcac cggatctaac aaaggaagtg ctcctcactc aaggcgttga gtttggatcc     300
agaacgagaa acgtcgtgtt cgacattttc accgggaaag gtcaagatat ggtgttcact     360
gtttacggcg agcattggag gaagatgaga agaatcatga cggttccttt cttcaccaac     420
aaagttgttc aacagaatcg tgaaggttgg gagtttgaag cagctagtgt tgttgaagat     480
gttaagaaga atccagattc tgctacgaaa ggaatcgtgt tgaggaaacg tttgcaattg     540
atgatgtata acaatatgtt ccgtatcatg ttcgatagaa gatttgagag tgaggatgat     600
cctcttttcc ttaggcttaa ggctttgaat ggtgagagaa gtcgattagc tcagagcttt     660
gagtataact atggagattt cattcctatc cttagaccat tcctcagagg ctatttgaag     720
atttgtcaag atgtgaaaga tcgaagaatc gctcttttca agaagtactt tgttgatgag     780
aggaagcaaa ttgcgagttc taagcctaca ggtagtgaag gattgaaatg tgccattgat     840
cacatccttg aagctgagca aagggagaa atcaacgagg acaatgttct ttacatcgtc     900
gagaacatca atgtcgccgc gattgagaca acattgtggt ctatcgagtg ggaattgca     960
gagctagtga accatcctga aatccagagt aagctaagga cgaactcga cacagttctt    1020
ggaccgggtg tgcaagtcac cgagcctgat cttcacaaac ttccataccct tcaagctgtg    1080
gttaaggaga ctcttcgtct gagaatggcg attcctctcc tcgtgcctca catgaacctc    1140
catgatgcga agctcgctgg ctacgatatc cagcagaaa gcaaatcct tgttaatgct    1200
tggtggctag caaacaaccc caacagctgg aagaagcctg aagagtttag accagagagg    1260
ttcttgaag aagaatcgca cgtggaagct aacggtaatg acttcaggta tgtgccatt    1320
ggtgttggac gtcgaagctg tcccgggatt atattggcat tgcctatttt ggggatcacc    1380
attggtagga tggtccagaa cttcgagctt cttcctcctc caggacagtc taaagtggat    1440
actagtgaga aggtggaca attcagcttg cacatcctta accactccat aatcgttatg    1500
aaaccaagga actgttaa                                                  1518
```

<210> SEQ ID NO 4
<211> LENGTH: 505
<212> TYPE: PRT
<213> ORGANISM: Arabidopsis thaliana

<400> SEQUENCE: 4

```
Met Asp Leu Leu Leu Glu Lys Ser Leu Ile Ala Val Phe Val Ala
1               5                   10                  15

Val Ile Leu Ala Thr Val Ile Ser Lys Leu Arg Gly Lys Lys Leu Lys
            20                  25                  30

Leu Pro Pro Gly Pro Ile Pro Ile Pro Ile Phe Gly Asn Trp Leu Gln
            35                  40                  45

Val Gly Asp Asp Leu Asn His Arg Asn Leu Val Asp Tyr Ala Lys Lys
50                      55                  60

Phe Gly Asp Leu Phe Leu Leu Arg Met Gly Gln Arg Asn Leu Val Val
65                  70                  75                  80

Val Ser Ser Pro Asp Leu Thr Lys Glu Val Leu Leu Thr Gln Gly Val
                    85                  90                  95

Glu Phe Gly Ser Arg Thr Arg Asn Val Val Phe Asp Ile Phe Thr Gly
                100                 105                 110

Lys Gly Gln Asp Met Val Phe Thr Val Tyr Gly Glu His Trp Arg Lys
            115                 120                 125

Met Arg Arg Ile Met Thr Val Pro Phe Phe Thr Asn Lys Val Val Gln
130                 135                 140

Gln Asn Arg Glu Gly Trp Glu Phe Glu Ala Ala Ser Val Val Glu Asp
145                 150                 155                 160

Val Lys Lys Asn Pro Asp Ser Ala Thr Lys Gly Ile Val Leu Arg Lys
                165                 170                 175

Arg Leu Gln Leu Met Met Tyr Asn Asn Met Phe Arg Ile Met Phe Asp
                180                 185                 190

Arg Arg Phe Glu Ser Glu Asp Asp Pro Leu Phe Leu Arg Leu Lys Ala
            195                 200                 205

Leu Asn Gly Glu Arg Ser Arg Leu Ala Gln Ser Phe Glu Tyr Asn Tyr
210                 215                 220

Gly Asp Phe Ile Pro Ile Leu Arg Pro Phe Leu Arg Gly Tyr Leu Lys
225                 230                 235                 240

Ile Cys Gln Asp Val Lys Asp Arg Arg Ile Ala Leu Phe Lys Lys Tyr
                245                 250                 255

Phe Val Asp Glu Arg Lys Gln Ile Ala Ser Ser Lys Pro Thr Gly Ser
                260                 265                 270

Glu Gly Leu Lys Cys Ala Ile Asp His Ile Leu Glu Ala Glu Gln Lys
            275                 280                 285

Gly Glu Ile Asn Glu Asp Asn Val Leu Tyr Ile Val Glu Asn Ile Asn
290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Arg Asn Glu Leu
                325                 330                 335

Asp Thr Val Leu Gly Pro Gly Val Gln Val Thr Glu Pro Asp Leu His
                340                 345                 350

Lys Leu Pro Tyr Leu Gln Ala Val Val Lys Glu Thr Leu Arg Leu Arg
            355                 360                 365

Met Ala Ile Pro Leu Leu Val Pro His Met Asn Leu His Asp Ala Lys
370                 375                 380
```

```
Leu Ala Gly Tyr Asp Ile Pro Ala Glu Ser Lys Ile Leu Val Asn Ala
385                 390                 395                 400

Trp Trp Leu Ala Asn Pro Asn Ser Trp Lys Lys Pro Glu Glu Phe
            405                 410                 415

Arg Pro Glu Arg Phe Glu Glu Ser His Val Glu Ala Asn Gly
        420                 425                 430

Asn Asp Phe Arg Tyr Val Pro Phe Gly Val Gly Arg Arg Ser Cys Pro
            435                 440                 445

Gly Ile Ile Leu Ala Leu Pro Ile Leu Gly Ile Thr Ile Gly Arg Met
        450                 455                 460

Val Gln Asn Phe Glu Leu Leu Pro Pro Gly Gln Ser Lys Val Asp
465                 470                 475                 480

Thr Ser Glu Lys Gly Gly Gln Phe Ser Leu His Ile Leu Asn His Ser
            485                 490                 495

Ile Ile Val Met Lys Pro Arg Asn Cys
        500                 505

<210> SEQ ID NO 5
<211> LENGTH: 1686
<212> TYPE: DNA
<213> ORGANISM: Arabidopsis thaliana

<400> SEQUENCE: 5
atggcgccac aagaacaagc agtttctcag gtgatggaga acagagcaa caacaacaac      60 agtgacgtca ttttccgatc aaagttaccg gatatttaca tcccgaacca cctatctctc    120
cacgactaca tcttccaaaa catctccgaa ttcgccacta gccttgcct aatcaacgga     180 ccaaccggcc acgtgtacac ttactccgac gtccacgtca tctcccgcca atcgccgcc    240 aattttcaca aactcggcgt taaccaaaac gacgtcgtca tgctcctcct cccaaactgt    300
cccgaattcg tcctctcttt cctcgccgcc tccttccgcg cgcaaccgc caccgccgca    360 aacccttttct tcactccggc ggagatagct aaacaagcca agcctccaa caccaaactc    420 ataatcaccg aagctcgtta cgtcgacaaa atcaaaccac ttcaaaacga cgacggagta    480
gtcatcgtct gcatcgacga caacgaatcc gtgccaatcc ctgaaggctg cctccgcttc    540
accgagttga ctcagtcgac aaccgaggca tcagaagtca tcgactcggt ggagatttca    600
ccggacgacg tggtggcact accttactcc tctggcacga cgggattacc aaaaggagtg    660
atgctgactc acaagggact agtcacgagc gttgctcagc aagtcgacgg cgagaacccg    720
aatctttatt tccacagcga tgacgtcata tctctgtgttt tgcccatgtt tcatatctac    780
gctttgaact cgatcatgtt gtgtggtctt agagttggtg cggcgattct gataatgccg    840
aagtttgaga tcaatctgct attggagctg atccagaggt gtaaagtgac ggtggctccg    900
atggttccgc cgattgtgtt ggccattgcg aagtcttcgg agacggagaa gtatgatttg    960
agctcgataa gagtggtgaa atctggtgct gctcctcttg gtaaagaact tgaagatgcc   1020
gttaatgcca agtttcctaa tgccaaactc ggtcagggat acggaatgac ggaagcaggt   1080
ccagtgctag caatgtcgtt aggttttgca aaggaaccctt ttccggttaa gtcaggagct   1140
tgtggtactg ttgtaagaaa tgctgagatg aaaatagttg atccagacac cggagattct   1200
ctttcgagga atcaacccgg tgagatttgt attcgtggtc accagatcat gaaaggttac   1260
ctcaacaatc cggcagctac agcagagacc attgataaag acggttggct tcatactgga   1320
gatattggat tgatcgatga cgatgacgag ctttccatcg ttgatcgatt gaagaacttt   1380
```

```
atcaagtata aaggttttca ggtagctccg gctgagctag aggctttgct catcggtcat    1440
cctgacatta ctgatgttgc tgttgtcgca atgaaagaag aagcagctgg tgaagttcct    1500
gttgcatttg tggtgaaatc gaaggattcg gagttatcag aagatgatgt gaagcaattc    1560
gtgtcgaaac aggttgtgtt ttacaagaga atcaacaaag tgttcttcac tgaatccatt    1620
cctaaagctc catcagggaa gatattgagg aaagatctga gggcaaaact agcaaatgga    1680
ttgtga                                                                1686

<210> SEQ ID NO 6
<211> LENGTH: 561
<212> TYPE: PRT
<213> ORGANISM: Arabidopsis thaliana

<400> SEQUENCE: 6

Met Ala Pro Gln Glu Gln Ala Val Ser Gln Val Met Glu Lys Gln Ser
1               5                   10                  15

Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
            100                 105                 110

Arg Gly Ala Thr Ala Thr Ala Ala Asn Pro Phe Phe Thr Pro Ala Glu
        115                 120                 125

Ile Ala Lys Gln Ala Lys Ala Ser Asn Thr Lys Leu Ile Ile Thr Glu
    130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Asp Val Val Ala Leu Pro
        195                 200                 205

Tyr Ser Ser Gly Thr Thr Gly Leu Pro Lys Gly Val Met Leu Thr His
    210                 215                 220

Lys Gly Leu Val Thr Ser Val Ala Gln Gln Val Asp Gly Glu Asn Pro
225                 230                 235                 240

Asn Leu Tyr Phe His Ser Asp Asp Val Ile Leu Cys Val Leu Pro Met
                245                 250                 255

Phe His Ile Tyr Ala Leu Asn Ser Ile Met Leu Cys Gly Leu Arg Val
            260                 265                 270

Gly Ala Ala Ile Leu Ile Met Pro Lys Phe Glu Ile Asn Leu Leu Leu
        275                 280                 285

Glu Leu Ile Gln Arg Cys Lys Val Thr Val Ala Pro Met Val Pro Pro
    290                 295                 300

Ile Val Leu Ala Ile Ala Lys Ser Ser Glu Thr Glu Lys Tyr Asp Leu
305                 310                 315                 320
```

Ser Ser Ile Arg Val Val Lys Ser Gly Ala Ala Pro Leu Gly Lys Glu
            325                 330                 335

Leu Glu Asp Ala Val Asn Ala Lys Phe Pro Asn Ala Lys Leu Gly Gln
            340                 345                 350

Gly Tyr Gly Met Thr Glu Ala Gly Pro Val Leu Ala Met Ser Leu Gly
            355                 360                 365

Phe Ala Lys Glu Pro Phe Pro Val Lys Ser Gly Ala Cys Gly Thr Val
            370                 375                 380

Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
            405                 410                 415

Met Lys Gly Tyr Leu Asn Asn Pro Ala Ala Thr Ala Glu Thr Ile Asp
            420                 425                 430

Lys Asp Gly Trp Leu His Thr Gly Asp Ile Gly Leu Ile Asp Asp Asp
            435                 440                 445

Asp Glu Leu Phe Ile Val Asp Arg Leu Lys Glu Leu Ile Lys Tyr Lys
            450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
            485                 490                 495

Gly Glu Val Pro Val Ala Phe Val Val Lys Ser Lys Asp Ser Glu Leu
            500                 505                 510

Ser Glu Asp Asp Val Lys Gln Phe Val Ser Lys Gln Val Val Phe Tyr
            515                 520                 525

Lys Arg Ile Asn Lys Val Phe Phe Thr Glu Ser Ile Pro Lys Ala Pro
            530                 535                 540

Ser Gly Lys Ile Leu Arg Lys Asp Leu Arg Ala Lys Leu Ala Asn Gly
545                 550                 555                 560

Leu

<210> SEQ ID NO 7
<211> LENGTH: 1176
<212> TYPE: DNA
<213> ORGANISM: Rheum tataricum

<400> SEQUENCE: 7
atggcaccgg aggagtccag gcatgctgaa actgcagtta acagagccgc caccgtcctg      60
gccatcggca ctgccaaccc gccaaactgc tactatcaag cggactttcc tgacttctac     120
ttccgtgcca ccaacagcga ccacctcacg cacctcaagc aaaaatttaa gcgcatttgt     180
gagaaatcga tgattgaaaa acgttatctc catttgacgg aagaaattct caaggagaat     240
ccaaatattg cttccttcga ggcgccatca ttggatgtaa acataacat tcaagtgaaa     300 gaagtggtgc tgctcggaaa agaggcagct ttgaaggcca tcaatgagtg ggccaaccc     360 aagtcaaaga tcacgcgcct cattgtgtgt tgtattgccg gcgttgacat gcccggcgca     420
gactatcaac tcactaaact ccttggctta caactttctg ttaagcgatt tatgttttac     480
caccctagga tgctatgccg gtggcaccgtc cttcgccttg cgaaggacat agcagaaaac     540
aacaaggaag ctcgtgttct catcgttcgc tctgagatga cgccaatctg tttccgtggg     600
ccatccgaaa cccacataga ctccatggta gggcaagcaa tatttggtga cggtgctgcg     660
gctgttatag ttggtgcaaa tcccgaccta tccatcgaaa ggccgatttt cgagttgatt     720

```
tctacatccc aaactatcat acctgaatcc gatggtgcga ttgagggaca tttgcttgaa      780
gttggactca gtttccaact ctaccagact gttccctcat taatctctaa ttgtatcgaa      840
acttgtcttt caaaggcttt cacacctctt aacattagtg attggaactc actattctgg      900
attgcacacc ctggtggccg tgctatcctt gacgatatcg aggctactgt tggtctcaag      960
aaggagaaac ttaaggcaac aagacaagtt ttgaacgact atgggaacat gtcaagtgct     1020
tgcgtatttt tcatcatgga tgagatgagg aagaagtcgc tcgcaaacgg tcaagtaacc     1080
actggagaag gactcaagtg gggtgttctt tttgggttcg ggccaggtgt tactgtggaa     1140
actgtggttc taagcagtgt gccgctaatt acctga                               1176
```

<210> SEQ ID NO 8
<211> LENGTH: 391
<212> TYPE: PRT
<213> ORGANISM: Rheum tataricum

<400> SEQUENCE: 8

```
Met Ala Pro Glu Glu Ser Arg His Ala Glu Thr Ala Val Asn Arg Ala
1               5                   10                  15

Ala Thr Val Leu Ala Ile Gly Thr Ala Asn Pro Pro Asn Cys Tyr Tyr
            20                  25                  30

Gln Ala Asp Phe Pro Asp Phe Tyr Phe Arg Ala Thr Asn Ser Asp His
        35                  40                  45

Leu Thr His Leu Lys Gln Lys Phe Lys Arg Ile Cys Glu Lys Ser Met
    50                  55                  60

Ile Glu Lys Arg Tyr Leu His Leu Thr Glu Glu Ile Leu Lys Glu Asn
65                  70                  75                  80

Pro Asn Ile Ala Ser Phe Glu Ala Pro Ser Leu Asp Val Arg His Asn
                85                  90                  95

Ile Gln Val Lys Glu Val Val Leu Leu Gly Lys Glu Ala Ala Leu Lys
            100                 105                 110

Ala Ile Asn Glu Trp Gly Gln Pro Lys Ser Lys Ile Thr Arg Leu Ile
        115                 120                 125

Val Cys Cys Ile Ala Gly Val Asp Met Pro Gly Ala Asp Tyr Gln Leu
    130                 135                 140

Thr Lys Leu Leu Gly Leu Gln Leu Ser Val Lys Arg Phe Met Phe Tyr
145                 150                 155                 160

His Leu Gly Cys Tyr Ala Gly Gly Thr Val Leu Arg Leu Ala Lys Asp
                165                 170                 175

Ile Ala Glu Asn Asn Lys Glu Ala Arg Val Leu Ile Val Arg Ser Glu
            180                 185                 190

Met Thr Pro Ile Cys Phe Arg Gly Pro Ser Glu Thr His Ile Asp Ser
        195                 200                 205

Met Val Gly Gln Ala Ile Phe Gly Asp Gly Ala Ala Ala Val Ile Val
    210                 215                 220

Gly Ala Asn Pro Asp Leu Ser Ile Glu Arg Pro Ile Phe Glu Leu Ile
225                 230                 235                 240

Ser Thr Ser Gln Thr Ile Ile Pro Glu Ser Asp Gly Ala Ile Glu Gly
                245                 250                 255

His Leu Leu Glu Val Gly Leu Ser Phe Gln Leu Tyr Gln Thr Val Pro
            260                 265                 270

Ser Leu Ile Ser Asn Cys Ile Glu Thr Cys Leu Ser Lys Ala Phe Thr
        275                 280                 285
```

Pro Leu Asn Ile Ser Asp Trp Asn Ser Leu Phe Trp Ile Ala His Pro
    290                 295                 300

Gly Gly Arg Ala Ile Leu Asp Asp Ile Glu Ala Thr Val Gly Leu Lys
305                 310                 315                 320

Lys Glu Lys Leu Lys Ala Thr Arg Gln Val Leu Asn Asp Tyr Gly Asn
                325                 330                 335

Met Ser Ser Ala Cys Val Phe Phe Ile Met Asp Glu Met Arg Lys Lys
                340                 345                 350

Ser Leu Ala Asn Gly Gln Val Thr Thr Gly Glu Gly Leu Lys Trp Gly
            355                 360                 365

Val Leu Phe Gly Phe Gly Pro Gly Val Thr Val Glu Thr Val Val Leu
    370                 375                 380

Ser Ser Val Pro Leu Ile Thr
385                 390

<210> SEQ ID NO 9
<211> LENGTH: 1176
<212> TYPE: DNA
<213> ORGANISM: Rheum tataricum

<400> SEQUENCE: 9 atggcccag aagagagcag gcacgcagaa acggccgtta cagagctgc aactgttttg      60 gctattggta cggccaatcc acccaattgt tactatcaag ctgactttcc tgatttttat    120
ttcagagcca caaatagcga tcatttgact catcttaagc aaaaatttaa aaggatatgc    180
gagaagtcca tgattgaaaa agatacttg caccttaccg aagagatctt aaaagaaaac    240
ccaaatatag cttcttttga agctccctcc ttagatgtac gtcacaacat tcaagtcaag    300
gaggtggttt tacttggtaa ggaagccgca ttgaaagcta taacgaatg gggacagcct    360 aaaagtaaga taaccagatt gatcgtatgt tgcatagctg gcgttgacat gcctggtgca    420
gattatcaac taacaaaatt gctgggtcta caattatccg taaaaaggtt tatgttctac    480
catttaggct gttacgctgg tggcacagtt ttaagactgg ctaaggatat agcagaaaat    540
aacaaggagg ctagagtctt aatagtgcgt agtgaaatga ctcctatttg ctttagaggt    600
ccatcagaaa cacatatcga cagcatggta ggtcaggcaa ttttcggtga tggtgctgca    660
gccgtaattg tgggagctaa tcctgattta agtatcgaaa gacctatttt tgaacttatt    720
tctacttcgc aaaccattat ccccgaatca gatggtgcaa ttgaaggcca tttattggag    780 gttggttgt cctttcaatt gtatcagaca gtgccatctt aatttcaaa ctgtatagaa    840 acctgtctaa gtaaagcatt tacaccatta acatttctg actggaattc tttgttctgg    900
attgctcatc caggtggaag agccatctta gatgacatcg aagctactgt gggactgaaa    960
aaggaaaaac taaagctac tagacaagtt ttaaatgact acggtaatat gtcatctgct   1020 tgtgtattt tcattatgga tgagatgaga aaaagtcac ttgcaaatgg ccaggtcacg   1080
acaggtgagg gtctaaatg gggagtccta ttcggattcg gcccaggtgt cactgttgaa   1140
accgttgtcc tgtcttcggt tccattgatc acttaa                            1176

<210> SEQ ID NO 10
<211> LENGTH: 391
<212> TYPE: PRT
<213> ORGANISM: Rheum tataricum

<400> SEQUENCE: 10

Met Ala Pro Glu Glu Ser Arg His Ala Glu Thr Ala Val Asn Arg Ala
1               5                   10                  15

```
Ala Thr Val Leu Ala Ile Gly Thr Ala Asn Pro Pro Asn Cys Tyr Tyr
         20                  25                  30

Gln Ala Asp Phe Pro Asp Phe Tyr Phe Arg Ala Thr Asn Ser Asp His
         35                  40                  45

Leu Thr His Leu Lys Gln Lys Phe Lys Arg Ile Cys Glu Lys Ser Met
 50                  55                  60

Ile Glu Lys Arg Tyr Leu His Leu Thr Glu Glu Ile Leu Lys Glu Asn
 65                  70                  75                  80

Pro Asn Ile Ala Ser Phe Glu Ala Pro Ser Leu Asp Val Arg His Asn
                 85                  90                  95

Ile Gln Val Lys Glu Val Val Leu Leu Gly Lys Glu Ala Ala Leu Lys
                100                 105                 110

Ala Ile Asn Glu Trp Gly Gln Pro Lys Ser Lys Ile Thr Arg Leu Ile
             115                 120                 125

Val Cys Cys Ile Ala Gly Val Asp Met Pro Gly Ala Asp Tyr Gln Leu
130                 135                 140

Thr Lys Leu Leu Gly Leu Gln Leu Ser Val Lys Arg Phe Met Phe Tyr
145                 150                 155                 160

His Leu Gly Cys Tyr Ala Gly Gly Thr Val Leu Arg Leu Ala Lys Asp
                165                 170                 175

Ile Ala Glu Asn Asn Lys Glu Ala Arg Val Leu Ile Val Arg Ser Glu
            180                 185                 190

Met Thr Pro Ile Cys Phe Arg Gly Pro Ser Glu Thr His Ile Asp Ser
        195                 200                 205

Met Val Gly Gln Ala Ile Phe Gly Asp Gly Ala Ala Ala Val Ile Val
    210                 215                 220

Gly Ala Asn Pro Asp Leu Ser Ile Glu Arg Pro Ile Phe Glu Leu Ile
225                 230                 235                 240

Ser Thr Ser Gln Thr Ile Ile Pro Glu Ser Asp Gly Ala Ile Glu Gly
                245                 250                 255

His Leu Leu Glu Val Gly Leu Ser Phe Gln Leu Tyr Gln Thr Val Pro
            260                 265                 270

Ser Leu Ile Ser Asn Cys Ile Glu Thr Cys Leu Ser Lys Ala Phe Thr
        275                 280                 285

Pro Leu Asn Ile Ser Asp Trp Asn Ser Leu Phe Trp Ile Ala His Pro
    290                 295                 300

Gly Gly Arg Ala Ile Leu Asp Asp Ile Glu Ala Thr Val Gly Leu Lys
305                 310                 315                 320

Lys Glu Lys Leu Lys Ala Thr Arg Gln Val Leu Asn Asp Tyr Gly Asn
                325                 330                 335

Met Ser Ser Ala Cys Val Phe Phe Ile Met Asp Glu Met Arg Lys Lys
            340                 345                 350

Ser Leu Ala Asn Gly Gln Val Thr Thr Gly Glu Gly Leu Lys Trp Gly
        355                 360                 365

Val Leu Phe Gly Phe Gly Pro Gly Val Thr Val Glu Thr Val Val Leu
    370                 375                 380

Ser Ser Val Pro Leu Ile Thr
385                 390

<210> SEQ ID NO 11
<211> LENGTH: 1596
<212> TYPE: DNA
<213> ORGANISM: Rhodobacter capsulatus
```

<400> SEQUENCE: 11

```
atgaccctgc agtcacagac ggccaaggac tgcctcgcgc tggacggggc gctgacactt      60
gtccaatgcg aggccatcgc gacacatcgc agccggattt cggtgacccc cgcgctgcgc     120
gagcgctgcg cgcgggccca tgcccggctt gagcacgcca tcgccgagca gcgccacatt     180
tacggcatca ccaccggctt cggcccgctg gcgaaccgtc tgatcggggc cgatcagggg     240
gcggagctgc agcagaacct gatctatcat ctggccaccg gcgtcgggcc gaaactgagc     300
tgggccgagg cgcgggcgtt gatgctggcg cggctcaact cgatcctgca aggcgcgtcg     360
ggggcctcgc cggagacgat cgaccggatc gttgcggtgc tcaatgcggg gtttgccccc     420
gaggttccgg cgcagggaac ggtgggcgcc tcggcgatcg tgaccccgct gcgcatatg     480
gtgctggcgc tgcagggacg ggggcggatg atcgacccct cgggccgcgt gcaggaggcc     540
ggggcggtga tggatcggct ctgcggcggt ccgctgacgc tggcggcccg tgacgggctg     600
gcgctggtga atggcacctc ggcgatgacc gcgattgcgg ccctgaccgg ggtcgaggcg     660
gcgcgggcga tcgacgccgc gcttcggcac agcgcggtcc tgatggaggt cttgtccggt     720
catgccgaag cctggcatcc ggctttcgca gagctgcgcc cgcatccggg gcagctgcgg     780
gcgaccgagc ggctggcgca ggcgctggat ggggcggggc gggtctgtcg accctgacc     840
gcggcgcggc ggctgaccgc cgcggatctg cggcccgaag atcatccggc gcaggatgcc     900
tacagtctgc gcgtggtgcc gcaactggtc ggcgcggtct gggacacgct ggactggcac     960
gatcgtgtcg tcacctgcga gctcaattcc gtcaccgaca atccgatctt tcccgagggc    1020
tgcgcggtgc ccgccctgca cggcggcaat ttcatgggcg tgcatgtcgc ccttgcctcc    1080
gatgcgctga acgcggcgct ggtgacgctg gcgggcctgg tcgagcgtca gatcgcccgg    1140
ctgaccgacg aaaagctgaa caagggcctg cccgccttcc tgcacggggg gcaggcgggg    1200
ctgcaatcgg gcttcatggg ggcgcaggtc acggcgacgg cgcttctggc ggaaatgcgg    1260
gcgaatgcca cgccggtttc ggtgcagtcg ctgtcgacca atggcgccaa tcaggatgtg    1320
gtctcgatgg gaacgattgc cgcgcggagg gcgcgggcgc agctgctgcc cctgtcgcag    1380
atccaggcga tcctggcgct tgcccttgcc caggcgatgg atctgcttga cgaccccgag    1440
gggcaggccg gatggtcgct tacggcgcgg gatctgcggg accggatccg gcggtctcg     1500
cccgggcttc gcgccgacag accgcttgcc gggcatatcg aagcggtggc acagggtctg    1560
cgtcatccct ccgccgccgc cgatccccccg gcatga                             1596
```

<210> SEQ ID NO 12
<211> LENGTH: 531
<212> TYPE: PRT
<213> ORGANISM: Rhodobacter capsulatus

<400> SEQUENCE: 12

```
Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

Ile Ser Val Thr Pro Ala Leu Arg Glu Arg Cys Ala Arg Ala His Ala
        35                  40                  45

Arg Leu Glu His Ala Ile Ala Glu Gln Arg His Ile Tyr Gly Ile Thr
    50                  55                  60

Thr Gly Phe Gly Pro Leu Ala Asn Arg Leu Ile Gly Ala Asp Gln Gly
65                  70                  75                  80
```

-continued

```
Ala Glu Leu Gln Gln Asn Leu Ile Tyr His Leu Ala Thr Gly Val Gly
                 85                  90                  95

Pro Lys Leu Ser Trp Ala Glu Ala Arg Ala Leu Met Leu Ala Arg Leu
            100                 105                 110

Asn Ser Ile Leu Gln Gly Ala Ser Gly Ala Ser Pro Glu Thr Ile Asp
            115                 120                 125

Arg Ile Val Ala Val Leu Asn Ala Gly Phe Ala Pro Glu Val Pro Ala
130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190

Thr Leu Ala Ala Arg Asp Gly Leu Ala Leu Val Asn Gly Thr Ser Ala
            195                 200                 205

Met Thr Ala Ile Ala Ala Leu Thr Gly Val Glu Ala Ala Arg Ala Ile
    210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
            260                 265                 270

Gly Arg Val Cys Arg Thr Leu Thr Ala Ala Arg Arg Leu Thr Ala Ala
        275                 280                 285

Asp Leu Arg Pro Glu Asp His Pro Ala Gln Asp Ala Tyr Ser Leu Arg
    290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335

Phe Pro Glu Gly Cys Ala Val Pro Ala Leu His Gly Gly Asn Phe Met
            340                 345                 350

Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
    370                 375                 380

Lys Leu Asn Lys Gly Leu Pro Ala Phe Leu His Gly Gly Gln Ala Gly
385                 390                 395                 400

Leu Gln Ser Gly Phe Met Gly Ala Gln Val Thr Ala Thr Ala Leu Leu
                405                 410                 415

Ala Glu Met Arg Ala Asn Ala Thr Pro Val Ser Val Gln Ser Leu Ser
            420                 425                 430

Thr Asn Gly Ala Asn Gln Asp Val Val Ser Met Gly Thr Ile Ala Ala
        435                 440                 445

Arg Arg Ala Arg Ala Gln Leu Leu Pro Leu Ser Gln Ile Gln Ala Ile
    450                 455                 460

Leu Ala Leu Ala Leu Ala Gln Ala Met Asp Leu Leu Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
```

```
               500                 505                 510
Ile Glu Ala Val Ala Gln Gly Leu Arg His Pro Ser Ala Ala Ala Asp
        515                 520                 525

Pro Pro Ala
        530

<210> SEQ ID NO 13
<211> LENGTH: 1596
<212> TYPE: DNA
<213> ORGANISM: Rhodobacter capsulatus

<400> SEQUENCE: 13
atgaccctgc aatctcaaac agctaaagat tgtttggctt tggatggtgc cttgacatta      60
gttcaatgcg aagcgatagc aacccataga agtagaatct ctgtaacacc agccctacgt     120
gagagatgtg ctagagcaca tgctaggtta aacatgcaa tagccgaaca gcgacacata      180
tatgggataa cgacaggctt cgggccactt gctaacaggc tgatcggagc agaccagggt     240
gctgaattac aacagaacct tatctaccat ttggcaaccg agttggccc caaattatca      300
tgggccgaag ccagagcttt aatgctcgct cgtttgaata gtatactaca aggtgcttct     360
ggtgctagcc ctgaaacaat tgataggatc gttgcagtct taaatgccgg atttgccccg     420
gaagtcccag cccaaggaac cgttggtgct tcgggtgact taactccgtt agcacacatg     480
gtattagcat tgcaaggcag aggtcgtatg attgatcctt cagggagagt tcaagaagcc     540
ggcgctgtca tggataggtt gtgtggaggc ccttttaacat tggctgccag agatggcctc     600
gccttagtaa atggtacatc tgccatgaca gctattgccg cattgaccgg tgtggaggct     660
gcaagagcga ttgatgcagc gcttagacat tccgcagtct tgatggaggt cctgtcaggg     720
catgctgagg cttggcaccc tgcctttgcg gaattgcgtc cgcatccagg acaattacgc     780
gccactgaga ggttagctca agcattggac ggcgcaggta gagtctgccg gactcttaca     840
gccgctaggc gtctaactgc agctgatctg agaccagaag atcatccagc tcaagatgca     900
tattcacttc gagtagttcc tcagctggtt ggtgccgtat gggatacgtt ggattggcac     960
gacagggttg tgacttgcga acttaactcc gtgaccgaca tccaatttt ccccgagggt     1020
tgtgcggttc cagcactaca cggtggaaac tttatgggcg tacatgtggc actagcttct     1080
gacgctttaa atgcagcgtt ggttacatta gctggtctag ttgaaaggca gattgcaaga     1140
cttactgatg agaagttgaa taagggtttg cctgcttttt tgcatggagg ccaagcaggt     1200
ttacaatcag gtttcatggg agctcaggtt actgctactg ctttgctagc ggaaatgaga     1260
gctaacgcga ctcccgtgtc cgttcaaagc ctcagcacca atggtgcaaa tcaagacgtg     1320
gtaagtatgg gtacgattgc cgcgagacga gcaagagctc aacttttacc tctgtctcaa     1380
atccaagcga ttttggcact ggctcttgca caagccatgg atctcctaga cgatcctgaa     1440
ggacaagccg ttggtccttt aacggcaaga gatttaagag accgtatacg gctgtcagt      1500
ccagggttgc gcgcagatag accactagcg ggtcatattg aagctgtggc tcaaggtcta     1560
agacacccct cggcagctgc cgatccacct gcttaa                               1596

<210> SEQ ID NO 14
<211> LENGTH: 531
<212> TYPE: PRT
<213> ORGANISM: Rhodobacter capsulatus

<400> SEQUENCE: 14

Met Thr Leu Gln Ser Gln Thr Ala Lys Asp Cys Leu Ala Leu Asp Gly
```

-continued

```
1               5                   10                  15
Ala Leu Thr Leu Val Gln Cys Glu Ala Ile Ala Thr His Arg Ser Arg
            20                  25                  30
Ile Ser Val Thr Pro Ala Leu Arg Glu Arg Cys Ala Arg Ala His Ala
            35                  40                  45
Arg Leu Glu His Ala Ile Ala Glu Gln Arg His Ile Tyr Gly Ile Thr
50              55                  60
Thr Gly Phe Gly Pro Leu Ala Asn Arg Leu Ile Gly Ala Asp Gln Gly
65                  70                  75                  80
Ala Glu Leu Gln Gln Asn Leu Ile Tyr His Leu Ala Thr Gly Val Gly
                85                  90                  95
Pro Lys Leu Ser Trp Ala Glu Ala Arg Ala Leu Met Leu Ala Arg Leu
                100                 105                 110
Asn Ser Ile Leu Gln Gly Ala Ser Gly Ala Ser Pro Glu Thr Ile Asp
                115                 120                 125
Arg Ile Val Ala Val Leu Asn Ala Gly Phe Ala Pro Glu Val Pro Ala
130                 135                 140
Gln Gly Thr Val Gly Ala Ser Gly Asp Leu Thr Pro Leu Ala His Met
145                 150                 155                 160
Val Leu Ala Leu Gln Gly Arg Gly Arg Met Ile Asp Pro Ser Gly Arg
                165                 170                 175
Val Gln Glu Ala Gly Ala Val Met Asp Arg Leu Cys Gly Gly Pro Leu
                180                 185                 190
Thr Leu Ala Ala Arg Asp Gly Leu Ala Leu Val Asn Gly Thr Ser Ala
                195                 200                 205
Met Thr Ala Ile Ala Ala Leu Thr Gly Val Glu Ala Ala Arg Ala Ile
            210                 215                 220
Asp Ala Ala Leu Arg His Ser Ala Val Leu Met Glu Val Leu Ser Gly
225                 230                 235                 240
His Ala Glu Ala Trp His Pro Ala Phe Ala Glu Leu Arg Pro His Pro
                245                 250                 255
Gly Gln Leu Arg Ala Thr Glu Arg Leu Ala Gln Ala Leu Asp Gly Ala
                260                 265                 270
Gly Arg Val Cys Arg Thr Leu Thr Ala Ala Arg Arg Leu Thr Ala Ala
                275                 280                 285
Asp Leu Arg Pro Glu Asp His Pro Ala Gln Asp Ala Tyr Ser Leu Arg
            290                 295                 300
Val Val Pro Gln Leu Val Gly Ala Val Trp Asp Thr Leu Asp Trp His
305                 310                 315                 320
Asp Arg Val Val Thr Cys Glu Leu Asn Ser Val Thr Asp Asn Pro Ile
                325                 330                 335
Phe Pro Glu Gly Cys Ala Val Pro Ala Leu His Gly Gly Asn Phe Met
                340                 345                 350
Gly Val His Val Ala Leu Ala Ser Asp Ala Leu Asn Ala Ala Leu Val
                355                 360                 365
Thr Leu Ala Gly Leu Val Glu Arg Gln Ile Ala Arg Leu Thr Asp Glu
            370                 375                 380
Lys Leu Asn Lys Gly Leu Pro Ala Phe Leu His Gly Gly Gln Ala Gly
385                 390                 395                 400
Leu Gln Ser Gly Phe Met Gly Ala Gln Val Thr Ala Thr Ala Leu Leu
                405                 410                 415
Ala Glu Met Arg Ala Asn Ala Thr Pro Val Ser Val Gln Ser Leu Ser
                420                 425                 430
```

```
Thr Asn Gly Ala Asn Gln Asp Val Val Ser Met Gly Thr Ile Ala Ala
        435                 440                 445
Arg Arg Ala Arg Ala Gln Leu Leu Pro Leu Ser Gln Ile Gln Ala Ile
    450                 455                 460
Leu Ala Leu Ala Leu Ala Gln Ala Met Asp Leu Leu Asp Asp Pro Glu
465                 470                 475                 480
Gly Gln Ala Gly Trp Ser Leu Thr Ala Arg Asp Leu Arg Asp Arg Ile
                485                 490                 495
Arg Ala Val Ser Pro Gly Leu Arg Ala Asp Arg Pro Leu Ala Gly His
            500                 505                 510
Ile Glu Ala Val Ala Gln Gly Leu Arg His Pro Ser Ala Ala Ala Asp
        515                 520                 525
Pro Pro Ala
    530
```

<210> SEQ ID NO 15
<211> LENGTH: 2076
<212> TYPE: DNA
<213> ORGANISM: Saccharomyces cerevisiae

<400> SEQUENCE: 15

| | |
|---|---:|
| atgccgtttg gaatagacaa caccgacttc actgtcctgg cggggctagt gcttgccgtg | 60 |
| ctactgtacg taaagagaaa ctccatcaag gaactgctga tgtccgatga cggagatatc | 120 |
| acagctgtca gctcgggcaa cagagacatt gctcaggtgg tgaccgaaaa caacaagaac | 180 |
| tacttggtgt gtatgcgtc gcagactggg actgccgagg attacgccaa aaagttttcc | 240 |
| aaggagctgg tggccaagtt caacctaaac gtgatgtgcg cagatgttga aactacgac | 300 |
| tttgagtcgc taaacgatgt gcccgtcata gtctcgattt ttatctctac atatggtgaa | 360 |
| ggagacttcc ccgacggggc ggtcaacttt gaagacttta tttgtaatgc ggaagcgggt | 420 |
| gcactatcga acctgaggta taatatgttt ggtctgggaa attctactta tgaattcttt | 480 |
| aatggtgccg ccaagaaggc cgagaagcat ctctccgccg cgggcgctat cagactaggc | 540 |
| aagctcggtg aagctgatga tggtgcagga actacagacg aagattacat ggcctggaag | 600 |
| gactccatcc tggaggtttt gaaagacgaa ctgcatttgg acgaacagga agccaagttc | 660 |
| acctctcaat ccagtacac tgtgttgaac gaaatcactg actccatgtc gcttggtgaa | 720 |
| ccctctgctc actatttgcc ctcgcatcag ttgaaccgca acgcagacgg catccaattg | 780 |
| ggtcccttcg atttgtctca accgtatatt gcacccatcg tgaaatctcg cgaactgttc | 840 |
| tcttccaatg accgtaattg catccactct gaatttgact tgtccggctc taacatcaag | 900 |
| tactccactg gtgaccatct tgctgtttgg ccttccaacc cattggaaaa ggtcgaacag | 960 |
| ttcttatcca tattcaacct ggaccctgaa accattttg acttgaagcc cctggatccc | 1020 |
| accgtcaaag tgcccttccc aacgccaact actattggcg ctgctattaa acactatttg | 1080 |
| gaaattacag gacctgtctc cagacaattg ttttcatctt tgattcagtt cgcccccaac | 1140 |
| gctgacgtca aggaaaaatt gactctgctt tcgaaagaca aggaccaatt cgccgtcgag | 1200 |
| ataacctcca atatttcaa catcgcagat gctctgaaat atttgtctga tggcgccaaa | 1260 |
| tgggacaccg tacccatgca attcttggtc gaatcagttc cccaaaatgac tcctcgttac | 1320 |
| tactctatct cttcctcttc tctgtctgaa aagcaaaccg tccatgtcac ctccattgtg | 1380 |
| gaaaactttc ctaacccaga attgcctgat gctcctccag ttgttggtgt tacgactaac | 1440 |
| ttgttaagaa acattcaatt ggctcaaaac aatgttaaca ttgccgaaac taacctacct | 1500 |

```
gttcactacg atttaaatgg cccacgtaaa cttttcgcca attacaaatt gcccgtccac   1560
gttcgtcgtt ctaacttcag attgccttcc aaccctccca ccccagttat catgatcggt   1620
ccaggtaccg tgttgcccc attccgtggg tttatcagag agcgtgtcgc gttcctcgaa    1680
tcacaaaaga agggcggtaa caacgtttcg ctaggtaagc atatactgtt ttatggatcc   1740
cgtaacactg atgatttctt gtaccaggac gaatggccag aatacgccaa aaaattggat   1800
ggttcgttcg aaatggtcgt ggcccattcc aggttgccaa acaccaaaaa agtttatgtt   1860
caagataaat taaaggatta cgaagaccaa gtatttgaaa tgattaacaa cggtgcattt   1920
atctacgtct gtggtgatgc aaagggtatg gccaagggtg tgtcaaccgc attggttggc   1980
atcttatccc gtggtaaatc cattaccact gatgaagcaa cagagctaat caagatgctc   2040
aagacttcag gtagatacca agaagatgtc tggtaa                             2076
```

<210> SEQ ID NO 16
<211> LENGTH: 691
<212> TYPE: PRT
<213> ORGANISM: Saccharomyces cerevisiae

<400> SEQUENCE: 16

```
Met Pro Phe Gly Ile Asp Asn Thr Asp Phe Thr Val Leu Ala Gly Leu
1               5                   10                  15

Val Leu Ala Val Leu Leu Tyr Val Lys Arg Asn Ser Ile Lys Glu Leu
            20                  25                  30

Leu Met Ser Asp Asp Gly Asp Ile Thr Ala Val Ser Ser Gly Asn Arg
        35                  40                  45

Asp Ile Ala Gln Val Val Thr Glu Asn Asn Lys Asn Tyr Leu Val Leu
    50                  55                  60

Tyr Ala Ser Gln Thr Gly Thr Ala Glu Asp Tyr Ala Lys Lys Phe Ser
65                  70                  75                  80

Lys Glu Leu Val Ala Lys Phe Asn Leu Asn Val Met Cys Ala Asp Val
                85                  90                  95

Glu Asn Tyr Asp Phe Glu Ser Leu Asn Asp Val Pro Val Ile Val Ser
            100                 105                 110

Ile Phe Ile Ser Thr Tyr Gly Glu Gly Asp Phe Pro Asp Gly Ala Val
        115                 120                 125

Asn Phe Glu Asp Phe Ile Cys Asn Ala Glu Ala Gly Ala Leu Ser Asn
    130                 135                 140

Leu Arg Tyr Asn Met Phe Gly Leu Gly Asn Ser Thr Tyr Glu Phe Phe
145                 150                 155                 160

Asn Gly Ala Ala Lys Lys Ala Glu Lys His Leu Ser Ala Ala Gly Ala
                165                 170                 175

Ile Arg Leu Gly Lys Leu Gly Glu Ala Asp Asp Gly Ala Gly Thr Thr
            180                 185                 190

Asp Glu Asp Tyr Met Ala Trp Lys Asp Ser Ile Leu Glu Val Leu Lys
        195                 200                 205

Asp Glu Leu His Leu Asp Glu Gln Glu Ala Lys Phe Thr Ser Gln Phe
    210                 215                 220

Gln Tyr Thr Val Leu Asn Glu Ile Thr Asp Ser Met Ser Leu Gly Glu
225                 230                 235                 240

Pro Ser Ala His Tyr Leu Pro Ser His Gln Leu Asn Arg Asn Ala Asp
                245                 250                 255

Gly Ile Gln Leu Gly Pro Phe Asp Leu Ser Gln Pro Tyr Ile Ala Pro
            260                 265                 270
```

```
Ile Val Lys Ser Arg Glu Leu Phe Ser Ser Asn Asp Arg Asn Cys Ile
            275                 280                 285

His Ser Glu Phe Asp Leu Ser Gly Ser Asn Ile Lys Tyr Ser Thr Gly
290                 295                 300

Asp His Leu Ala Val Trp Pro Ser Asn Pro Leu Glu Lys Val Glu Gln
305                 310                 315                 320

Phe Leu Ser Ile Phe Asn Leu Asp Pro Glu Thr Ile Phe Asp Leu Lys
                325                 330                 335

Pro Leu Asp Pro Thr Val Lys Val Pro Phe Pro Thr Pro Thr Thr Ile
            340                 345                 350

Gly Ala Ala Ile Lys His Tyr Leu Glu Ile Thr Gly Pro Val Ser Arg
            355                 360                 365

Gln Leu Phe Ser Ser Leu Ile Gln Phe Ala Pro Asn Ala Asp Val Lys
370                 375                 380

Glu Lys Leu Thr Leu Leu Ser Lys Asp Lys Asp Gln Phe Ala Val Glu
385                 390                 395                 400

Ile Thr Ser Lys Tyr Phe Asn Ile Ala Asp Ala Leu Lys Tyr Leu Ser
                405                 410                 415

Asp Gly Ala Lys Trp Asp Thr Val Pro Met Gln Phe Leu Val Glu Ser
            420                 425                 430

Val Pro Gln Met Thr Pro Arg Tyr Tyr Ser Ile Ser Ser Ser Ser Leu
            435                 440                 445

Ser Glu Lys Gln Thr Val His Val Thr Ser Ile Val Glu Asn Phe Pro
450                 455                 460

Asn Pro Glu Leu Pro Asp Ala Pro Pro Val Gly Val Thr Thr Asn
465                 470                 475                 480

Leu Leu Arg Asn Ile Gln Leu Ala Gln Asn Asn Val Asn Ile Ala Glu
                485                 490                 495

Thr Asn Leu Pro Val His Tyr Asp Leu Asn Gly Pro Arg Lys Leu Phe
            500                 505                 510

Ala Asn Tyr Lys Leu Pro Val His Val Arg Arg Ser Asn Phe Arg Leu
            515                 520                 525

Pro Ser Asn Pro Ser Thr Pro Val Ile Met Ile Gly Pro Gly Thr Gly
            530                 535                 540

Val Ala Pro Phe Arg Gly Phe Ile Arg Glu Arg Val Ala Phe Leu Glu
545                 550                 555                 560

Ser Gln Lys Lys Gly Gly Asn Asn Val Ser Leu Gly Lys His Ile Leu
                565                 570                 575

Phe Tyr Gly Ser Arg Asn Thr Asp Asp Phe Leu Tyr Gln Asp Glu Trp
            580                 585                 590

Pro Glu Tyr Ala Lys Lys Leu Asp Gly Ser Phe Glu Met Val Val Ala
            595                 600                 605

His Ser Arg Leu Pro Asn Thr Lys Lys Val Tyr Val Gln Asp Lys Leu
610                 615                 620

Lys Asp Tyr Glu Asp Gln Val Phe Glu Met Ile Asn Asn Gly Ala Phe
625                 630                 635                 640

Ile Tyr Val Cys Gly Asp Ala Lys Gly Met Ala Lys Gly Val Ser Thr
                645                 650                 655

Ala Leu Val Gly Ile Leu Ser Arg Gly Lys Ser Ile Thr Thr Asp Glu
            660                 665                 670

Ala Thr Glu Leu Ile Lys Met Leu Lys Thr Ser Gly Arg Tyr Gln Glu
            675                 680                 685
```

Asp Val Trp
  690

<210> SEQ ID NO 17
<211> LENGTH: 2136
<212> TYPE: DNA
<213> ORGANISM: Arabidopsis thaliana

<400> SEQUENCE: 17

| | | | | | |
|---|---|---|---|---|---|
| atgtcctctt | cttcttcttc | gtcaacctcc | atgatcgatc | tcatggcagc | aatcatcaaa | 60 |
| ggagagcctg | taattgtctc | cgacccagct | aatgcctccg | cttacgagtc | cgtagctgct | 120 |
| gaattatcct | ctatgcttat | agagaatcgt | caattcgcca | tgattgttac | cacttccatt | 180 |
| gctgttctta | ttggttgcat | cgttatgctc | gtttggagga | gatccggttc | tgggaattca | 240 |
| aaacgtgtcg | agcctcttaa | gcctttggtt | attaagcctc | gtgaggaaga | gattgatgat | 300 |
| gggcgtaaga | aagttaccat | cttttcggt | acacaaactg | gtactgctga | aggttttgca | 360 |
| aaggctttag | gagaagaagc | taaagcaaga | tatgaaaaga | ccagattcaa | aatcgttgat | 420 |
| ttggatgatt | acgcggctga | tgatgatgag | tatgaggaga | aattgaagaa | agaggatgtg | 480 |
| gctttcttct | tcttagccac | atatggagat | ggtgagccta | ccgacaatgc | agcgagattc | 540 |
| tacaaatggt | tcaccgaggg | gaatgacaga | ggagaatggc | ttaagaactt | gaagtatgga | 600 |
| gtgtttggat | taggaaacag | acaatatgag | cattttaata | aggttgccaa | agttgtagat | 660 |
| gacattcttg | tcgaacaagg | tgcacagcgt | cttgtacaag | ttggtcttgg | agatgatgac | 720 |
| cagtgtattg | aagatgactt | taccgcttgg | cgagaagcat | gtggcccga | gcttgataca | 780 |
| atactgaggg | aagaagggga | tacagctgtt | gccacaccat | acactgcagc | tgtgttagaa | 840 |
| tacagagttt | ctattcacga | ctctgaagat | gccaaattca | atgatataaa | catggcaaat | 900 |
| gggaatggtt | acactgtgtt | tgatgctcaa | catccttaca | aagcaaatgt | cgctgttaaa | 960 |
| agggagcttc | atactcccga | gtctgatcgt | tcttgtatcc | atttggaatt | tgacattgct | 1020 |
| ggaagtggac | ttacgtatga | aactggagat | catgttggtg | tactttgtga | taacttaagt | 1080 |
| gaaactgtag | atgaagctct | tagattgctg | gatatgtcac | ctgatactta | tttctcactt | 1140 |
| cacgctgaaa | aagaagacgg | cacaccaatc | agcagctcac | tgcctcctcc | cttcccacct | 1200 |
| tgcaacttga | aacagcgct | tacacgatat | gcatgtcttt | tgagttctcc | aaagaagtct | 1260 |
| gctttagttg | cgttggctgc | tcatgcatct | gatcctaccg | aagcagaacg | attaaaaacac | 1320 |
| cttgcttcac | ctgctggaaa | ggatgaatat | tcaaagtggg | tagtagagag | tcaaagaagt | 1380 |
| ctacttgagg | tgatggccga | gtttccttca | gccaagccac | cacttggtgt | cttcttcgct | 1440 |
| ggagttgctc | caaggttgca | gcctaggttc | tattcgatat | catcatcgcc | caagattgct | 1500 |
| gaaactagaa | ttcacgtcac | atgtgcactg | gtttatgaga | aaatgccaac | tgcaggatt | 1560 |
| cataagggag | tgtgttccac | ttggatgaag | aatgctgtgc | cttacgagaa | gagtgaaaac | 1620 |
| tgttcctcgg | cgccgatatt | tgttaggcaa | tccaacttca | agcttccttc | tgattctaag | 1680 |
| gtaccgatca | tcatgatcgg | tccagggact | ggattagctc | cattcagagg | attccttcag | 1740 |
| gaaagactag | cgttggtaga | atctggtgtt | gaacttgggc | catcagtttt | gttctttgga | 1800 |
| tgcagaaacc | gtaatgga | tttcatctac | gaggaagagc | tccagcgatt | tgttgagagt | 1860 |
| ggtgctctcg | cagagctaag | tgtcgccttc | tctcgtgaag | acccaccaa | agaatacgta | 1920 |
| cagcacaaga | tgatggacaa | ggcttctgat | atctggaata | tgatctctca | aggagcttat | 1980 |
| ttatatgttt | gtggtgacgc | caaaggcatg | gcaagagatg | ttcacagatc | tctccacaca | 2040 |

```
atagctcaag aacagggtc aatggattca actaaagcag agggcttcgt gaagaatctg    2100
caaacgagtg aagatatct tagagatgta tggtaa                              2136
```

<210> SEQ ID NO 18
<211> LENGTH: 711
<212> TYPE: PRT
<213> ORGANISM: Arabidopsis thaliana

<400> SEQUENCE: 18

```
Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
        115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
        195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Gly Asp Thr Ala Val Ala Thr
            260                 265                 270

Pro Tyr Thr Ala Ala Val Leu Glu Tyr Arg Val Ser Ile His Asp Ser
        275                 280                 285

Glu Asp Ala Lys Phe Asn Asp Ile Asn Met Ala Asn Gly Asn Gly Tyr
    290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Tyr Glu Thr Gly Asp His Val
            340                 345                 350

Gly Val Leu Cys Asp Asn Leu Ser Glu Thr Val Asp Glu Ala Leu Arg
```

```
                        355                 360                 365
Leu Leu Asp Met Ser Pro Asp Thr Tyr Phe Ser Leu His Ala Glu Lys
    370                 375                 380

Glu Asp Gly Thr Pro Ile Ser Ser Leu Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
                420                 425                 430

Thr Glu Ala Glu Arg Leu Lys His Leu Ala Ser Pro Ala Gly Lys Asp
            435                 440                 445

Glu Tyr Ser Lys Trp Val Val Glu Ser Gln Arg Ser Leu Leu Glu Val
        450                 455                 460

Met Ala Glu Phe Pro Ser Ala Lys Pro Pro Leu Gly Val Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Asn Cys Ser Ser Ala
530                 535                 540

Pro Ile Phe Val Arg Gln Ser Asn Phe Lys Leu Pro Ser Asp Ser Lys
545                 550                 555                 560

Val Pro Ile Ile Met Ile Gly Pro Gly Thr Gly Leu Ala Pro Phe Arg
                565                 570                 575

Gly Phe Leu Gln Glu Arg Leu Ala Leu Val Glu Ser Gly Val Glu Leu
                580                 585                 590

Gly Pro Ser Val Leu Phe Phe Gly Cys Arg Asn Arg Met Asp Phe
            595                 600                 605

Ile Tyr Glu Glu Glu Leu Gln Arg Phe Val Glu Ser Gly Ala Leu Ala
        610                 615                 620

Glu Leu Ser Val Ala Phe Ser Arg Glu Gly Pro Thr Lys Glu Tyr Val
625                 630                 635                 640

Gln His Lys Met Met Asp Lys Ala Ser Asp Ile Trp Asn Met Ile Ser
                645                 650                 655

Gln Gly Ala Tyr Leu Tyr Val Cys Gly Asp Ala Lys Gly Met Ala Arg
                660                 665                 670

Asp Val His Arg Ser Leu His Thr Ile Ala Gln Glu Gln Gly Ser Met
            675                 680                 685

Asp Ser Thr Lys Ala Glu Gly Phe Val Lys Asn Leu Gln Thr Ser Gly
        690                 695                 700

Arg Tyr Leu Arg Asp Val Trp
705                 710

<210> SEQ ID NO 19
<211> LENGTH: 33
<212> TYPE: DNA
<213> ORGANISM: Arabidopsis thaliana

<400> SEQUENCE: 19
cggaattctc atggatcaaa tcgaagcaat gtt                              33
```

```
<210> SEQ ID NO 20
<211> LENGTH: 29
<212> TYPE: DNA
<213> ORGANISM: Arabidopsis thaliana

<400> SEQUENCE: 20
cgactagttt agcaaatcgg aatcggagc                                    29

<210> SEQ ID NO 21
<211> LENGTH: 30
<212> TYPE: DNA
<213> ORGANISM: Arabidopsis thaliana

<400> SEQUENCE: 21
cgctcgagat atggacctcc tcttgctgga                                   30

<210> SEQ ID NO 22
<211> LENGTH: 32
<212> TYPE: DNA
<213> ORGANISM: Arabidopsis thaliana

<400> SEQUENCE: 22
cgggtacctt aacagttcct tggtttcata ac                                32

<210> SEQ ID NO 23
<211> LENGTH: 36
<212> TYPE: DNA
<213> ORGANISM: Arabidopsis thaliana

<400> SEQUENCE: 23
gctctagacc tatggcgcca caagaacaag cagttt                            36

<210> SEQ ID NO 24
<211> LENGTH: 36
<212> TYPE: DNA
<213> ORGANISM: Arabidopsis thaliana

<400> SEQUENCE: 24
gcggatcccc ttcacaatcc atttgctagt tttgcc                            36

<210> SEQ ID NO 25
<211> LENGTH: 31
<212> TYPE: DNA
<213> ORGANISM: Rheum tataricum

<400> SEQUENCE: 25
ccggatccaa atggccccag aagagagcag g                                 31

<210> SEQ ID NO 26
<211> LENGTH: 35
<212> TYPE: DNA
<213> ORGANISM: Rheum tataricum

<400> SEQUENCE: 26
cgctcgagtt aagtgatcaa tggaaccgaa gacag                             35

<210> SEQ ID NO 27
<211> LENGTH: 38
<212> TYPE: DNA
<213> ORGANISM: Rhodobacter capsulatus

<400> SEQUENCE: 27
ccgaattccc atgaccctgc aatctcaaac agctaaag                          38
```

<210> SEQ ID NO 28
<211> LENGTH: 30
<212> TYPE: DNA
<213> ORGANISM: Rhodobacter capsulatus

<400> SEQUENCE: 28
ccactagttt aagcaggtgg atcggcagct                                    30

<210> SEQ ID NO 29
<211> LENGTH: 37
<212> TYPE: DNA
<213> ORGANISM: Saccharomyces cerevisiae

<400> SEQUENCE: 29
ccctcgagat catgccgttt ggaatagaca acaccga                             37

<210> SEQ ID NO 30
<211> LENGTH: 36
<212> TYPE: DNA
<213> ORGANISM: Saccharomyces cerevisiae

<400> SEQUENCE: 30
ccaagcttat cgggctgatt accagacatc ttcttg                              36

<210> SEQ ID NO 31
<211> LENGTH: 36
<212> TYPE: DNA
<213> ORGANISM: Arabidopsis thaliana

<400> SEQUENCE: 31
ccggatcccc atgtcctctt cttcttcttc gtcaac                              36

<210> SEQ ID NO 32
<211> LENGTH: 34
<212> TYPE: DNA
<213> ORGANISM: Arabidopsis thaliana

<400> SEQUENCE: 32
ccctcgaggt gagtgtgtgg cttcaatagt ttcg                                34

<210> SEQ ID NO 33
<211> LENGTH: 40
<212> TYPE: DNA
<213> ORGANISM: Rhodobacter capsulatus

<400> SEQUENCE: 33
ccgctcgagc ggatgaccct gcaatctcaa acagctaaag                          40

<210> SEQ ID NO 34
<211> LENGTH: 30
<212> TYPE: DNA
<213> ORGANISM: Rhodobacter capsulatus

<400> SEQUENCE: 34
gcggatcctt aagcaggtgg atcggcagct                                    30

<210> SEQ ID NO 35
<211> LENGTH: 35
<212> TYPE: DNA
<213> ORGANISM: Arabidopsis thaliana

<400> SEQUENCE: 35
tgccatggca atggcgccac aagaacaagc agttt                               35

<210> SEQ ID NO 36
<211> LENGTH: 36
<212> TYPE: DNA
<213> ORGANISM: Arabidopsis thaliana

<400> SEQUENCE: 36
gcggatcccc ttcacaatcc atttgctagt tttgcc                    36

<210> SEQ ID NO 37
<211> LENGTH: 37
<212> TYPE: DNA
<213> ORGANISM: Arabidopsis thaliana

<400> SEQUENCE: 37
ttgcggccgc aaatctcgat cccgcgaaat taatacg                   37

<210> SEQ ID NO 38
<211> LENGTH: 36
<212> TYPE: DNA
<213> ORGANISM: Arabidopsis thaliana

<400> SEQUENCE: 38
cgctcgagcc ttcacaatcc atttgctagt tttgcc                    36

<210> SEQ ID NO 39
<211> LENGTH: 25
<212> TYPE: DNA
<213> ORGANISM: S. cerevisiae

<400> SEQUENCE: 39
gtattctata tccacgcctg caaac                                25

<210> SEQ ID NO 40
<211> LENGTH: 45
<212> TYPE: DNA
<213> ORGANISM: S. cerevisiae

<400> SEQUENCE: 40
agtacataca gggaacgtcc ctacaggaac gcaaacttaa gctac          45

<210> SEQ ID NO 41
<211> LENGTH: 50
<212> TYPE: DNA
<213> ORGANISM: S. cerevisiae

<400> SEQUENCE: 41
gcatacaatc aactatctca tatacaatgc cgtttggaat agacaacacc    50

<210> SEQ ID NO 42
<211> LENGTH: 28
<212> TYPE: DNA
<213> ORGANISM: S. cerevisiae

<400> SEQUENCE: 42
gcttccgcat tacaaataaa gtcttcaa                             28

<210> SEQ ID NO 43
<211> LENGTH: 42
<212> TYPE: DNA
<213> ORGANISM: S. cerevisiae

<400> SEQUENCE: 43

```
ggacgttccc tgtatgtact aggggatcg aagaaatgat gg                    42
```

<210> SEQ ID NO 44
<211> LENGTH: 25
<212> TYPE: DNA
<213> ORGANISM: S. cerevisiae

<400> SEQUENCE: 44

```
gagcaatgaa cccaataacg aaatc                                     25
```

<210> SEQ ID NO 45
<211> LENGTH: 25
<212> TYPE: DNA
<213> ORGANISM: S. cerevisiae

<400> SEQUENCE: 45

```
cttgacgttc gttcgactga tgagc                                     25
```

<210> SEQ ID NO 46
<211> LENGTH: 26
<212> TYPE: DNA
<213> ORGANISM: S. cerevisiae

<400> SEQUENCE: 46

```
tgtatatgag atagttgatt gtatgc                                    26
```

<210> SEQ ID NO 47
<211> LENGTH: 25
<212> TYPE: DNA
<213> ORGANISM: K. lactis

<400> SEQUENCE: 47

```
cttgacgttc gttcgactga tgagc                                     25
```

<210> SEQ ID NO 48
<211> LENGTH: 26
<212> TYPE: DNA
<213> ORGANISM: K. lactis

<400> SEQUENCE: 48

```
ctggaattcg atgatgtagt ttctgg                                    26
```

<210> SEQ ID NO 49
<211> LENGTH: 42
<212> TYPE: DNA
<213> ORGANISM: S. cerevisiae

<400> SEQUENCE: 49

```
ctacatcatc gaattccagc tacgtatggt catttcttct tc                  42
```

<210> SEQ ID NO 50
<211> LENGTH: 49
<212> TYPE: DNA
<213> ORGANISM: S. cerevisiae

<400> SEQUENCE: 50

```
tttttgatta aaattaaaaa aacttttag tttatgtatg tgttttttg            49
```

<210> SEQ ID NO 51
<211> LENGTH: 50
<212> TYPE: DNA
<213> ORGANISM: S. cerevisiae

<400> SEQUENCE: 51 agtttttttaatttaatcaaaaaatgagcgaagaaagcttattcgagtc 50

<210> SEQ ID NO 52
<211> LENGTH: 25
<212> TYPE: DNA
<213> ORGANISM: S. cerevisiae

<400> SEQUENCE: 52
cacctaaaga cctcatggcg ttacc 25

<210> SEQ ID NO 53
<211> LENGTH: 24
<212> TYPE: DNA
<213> ORGANISM: K. lactis

<400> SEQUENCE: 53
cggtctgcat tggatggtgg taac 24

<210> SEQ ID NO 54
<211> LENGTH: 25
<212> TYPE: DNA
<213> ORGANISM: K. lactis

<400> SEQUENCE: 54
gagcaatgaa cccaataacg aaatc 25

<210> SEQ ID NO 55
<211> LENGTH: 42
<212> TYPE: DNA
<213> ORGANISM: S. cerevisiae

<400> SEQUENCE: 55
ctacatcatc gaattccagc tacgtatggt catttcttct tc 42

<210> SEQ ID NO 56
<211> LENGTH: 44
<212> TYPE: DNA
<213> ORGANISM: S. cerevisiae

<400> SEQUENCE: 56
caccatccaa tgcagaccgt tttagtttat gtatgtgttt tttg 44

<210> SEQ ID NO 57
<211> LENGTH: 27
<212> TYPE: DNA
<213> ORGANISM: S. cerevisiae

<400> SEQUENCE: 57
tgttctgctc tcttcaattt tcctttc 27

<210> SEQ ID NO 58
<211> LENGTH: 43
<212> TYPE: DNA
<213> ORGANISM: S. cerevisiae

<400> SEQUENCE: 58
ctggaattcg atgatgtagt ttctaatttt ctgcgctgtt tcg 43

<210> SEQ ID NO 59
<211> LENGTH: 1083
<212> TYPE: DNA
<213> ORGANISM: S. cerevisiae

<400> SEQUENCE: 59

```
atgcttaaca gaacaattgc taagagaact ttagccactg ccgctcaggc ggaacgcacc      60
ctacccaaga agtatggcgg tcgtttcacc gtcactttga tacctggtga cggtgttggg     120
aaagaaatca ctgattcagt gagaaccatt tttgaggctg aaaatatccc gatcgactgg     180
gaaactataa acattaagca aacagatcat aaggaaggcg tctatgaagc tgttgagtct     240
ctaaagagaa ataagattgg tcttaagggg ctatggcaca ctcctgctga ccaaacaggt     300
cacggttcac taaacgttgc tttgcgtaaa caactagata tctacgccaa tgtggccctt     360
ttcaaatcct tgaagggtgt caagactaga attccagaca tagatttgat tgtcattaga     420
gaaaacacgg agggtgagtt ctcaggcctg aacatgaat ccgtccctgg tgtagtggaa      480
tctttgaaag ttatgactag acctaagaca gaaaggatcg ccagatttgc ctttgacttc     540
gccaagaaat acaacagaaa gtctgtcaca gctgtgcata aggcaaatat catgaagtta     600
ggtgacggtc tgttcagaaa tataataact gaaattggcc aaaaagaata tcctgatatt     660
gacgtatcgt ccatcattgt cgacaatgcc tccatgcagg cggtggccaa acctcatcaa     720
tttgatgtcc tagttacccc ttcaatgtac ggtaccatct taggcaacat ggcgctgct      780
ttgatcggtg gtccaggatt ggtggcaggt gccaactttg gcagggacta tgctgtcttc     840
gaaccaggtt ccagacatgt tggtttagat attaaaggcc aaaatgtggc taacccaact     900
gccatgatcc tttcctccac gttaatgttg aaccatttgg gtttgaatga atatgctact     960
agaatctcaa aggcagttca tgaaacgatc gcagaaggta agcataccac tagagatatt    1020
ggtggttcct cttctactac tgacttcacg aatgaaatca tcaacaaatt atctaccatg    1080
taa                                                                   1083
```

<210> SEQ ID NO 60
<211> LENGTH: 1671
<212> TYPE: DNA
<213> ORGANISM: A. thaliana

<400> SEQUENCE: 60

```
atgacgacac aagatgtgat agtcaatgat cagaatgatc agaaacagtg tagtaatgac     60
gtcattttcc gatcgagatt gcctgatata tacatcccta accacctccc actccacgac    120
tacatcttcg aaaatatctc agagttcgcc gctaagccat gcttgatcaa cggtcccacc    180
ggcgaagtat acacctacgc cgatgtccac gtaacatctc ggaaactcgc cgccggtctt    240
cataacctcg gcgtgaagca acacgacgtt gtaatgatcc tcctcccgaa ctctcctgaa    300
gtagtcctca ctttccttgc cgcctccttc atcggcgcaa tcaccacctc cgcgaacccg    360
ttcttcactc cggcggagat ttctaaacaa gccaaagcct ccgcggcgaa actcatcgtc    420
actcaatccc gttacgtcga taaaatcaag aacctccaaa acgacggcgt tttgatcgtc    480
accaccgact ccgacgccat ccccgaaaac tgcctccgtt tctccgagtt aactcagtcc    540
gaagaaccac gagtggactc aataccggag aagatttcgc cagaagacgt cgtggcgctt    600
cctttctcat ccggcacgac gggtctcccc aaaggagtga tgctaacaca caaaggtcta    660
gtcacgagcg tggcgcagca agtcgacggc gagaatccga tctttactt caacagagac    720
gacgtgatcc tctgtgtctt gcctatgttc catatatacg ctctcaactc catcatgctc    780
tgtagtctca gagttggtgc cacgatcttg ataatgccta agttcgaaat cactctcttg    840
ttagagcaga tacaaaggtg taaagtcacg gtggctatgg tcgtgccacc gatcgtttta    900
gctatcgcga agtcgccgga gacggagaag tatgatctga gctcggttag gatggttaag    960
```

```
tctggagcag ctcctcttgg taaggagctt gaagatgcta ttagtgctaa gtttcctaac    1020
gccaagcttg gtcagggcta tgggatgaca gaagcaggtc cggtgctagc aatgtcgtta    1080
gggtttgcta aagagccgtt tccagtgaag tcaggagcat gtggtacggt ggtgaggaac    1140
gccgagatga agatacttga tccagacaca ggagattctt tgcctaggaa caaacccggc    1200
gaaatatgca tccgtggcaa ccaaatcatg aaaggctatc tcaatgaccc cttggccacg    1260
gcatcgacga tcgataaaga tggttggctt cacactggag acgtcggatt tatcgatgat    1320
gacgacgagc ttttcattgt ggatagattg aaagaactca tcaagtacaa aggatttcaa    1380
gtggctccag ctgagctaga gtctctcctc ataggtcatc cagaaatcaa tgatgttgct    1440
gtcgtcgcca tgaaggaaga agatgctggt gaggttcctg ttgcgtttgt ggtgagatcg    1500
aaagattcaa atatatccga agatgaaatc aagcaattcg tgtcaaaaca ggttgtgttt    1560
tataagagaa tcaacaaagt gttcttcact gactctattc ctaaagctcc atcagggaag    1620
atattgagga aggatctaag agcaagacta gcaaatggat taatgaacta g             1671
```

<210> SEQ ID NO 61
<211> LENGTH: 40
<212> TYPE: DNA
<213> ORGANISM: A. thaliana

<400> SEQUENCE: 61

```
gcgaattctt atgacgacac aagatgtgat agtcaatgat                            40
```

<210> SEQ ID NO 62
<211> LENGTH: 42
<212> TYPE: DNA
<213> ORGANISM: A. thaliana

<400> SEQUENCE: 62

```
gcactagtat cctagttcat taatccattt gctagtcttg ct                         42
```

<210> SEQ ID NO 63
<211> LENGTH: 392
<212> TYPE: PRT
<213> ORGANISM: Vitis vinifera

<400> SEQUENCE: 63

```
Met Ala Ser Val Glu Glu Phe Arg Asn Ala Gln Arg Ala Lys Gly Pro
1               5                   10                  15

Ala Thr Ile Leu Ala Ile Gly Thr Ala Thr Pro Asp His Cys Val Tyr
            20                  25                  30

Gln Ser Asp Tyr Ala Asp Tyr Tyr Phe Arg Val Thr Lys Ser Glu His
        35                  40                  45

Met Thr Glu Leu Lys Lys Lys Phe Asn Arg Ile Cys Asp Lys Ser Met
    50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Arg Leu Gly Arg Asp Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
    130                 135                 140
```

-continued

```
Ala Asn Leu Leu Gly Leu Glu Thr Ser Val Arg Arg Val Met Leu Tyr
145                 150                 155                 160

His Gln Gly Cys Tyr Ala Gly Gly Thr Val Leu Arg Thr Ala Lys Asp
                165                 170                 175

Leu Ala Glu Asn Asn Ala Gly Ala Arg Val Leu Val Val Cys Ser Glu
            180                 185                 190

Ile Thr Val Val Thr Phe Arg Gly Pro Ser Glu Asp Ala Leu Asp Ser
        195                 200                 205

Leu Val Gly Gln Ala Leu Phe Gly Asp Gly Ser Ser Ala Val Ile Val
    210                 215                 220

Gly Ser Asp Pro Asp Val Ser Ile Glu Arg Pro Leu Phe Gln Leu Val
225                 230                 235                 240

Ser Ala Ala Gln Thr Phe Ile Pro Asn Ser Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Lys Cys Leu Thr Gln Ala Phe Asp
        275                 280                 285

Pro Leu Gly Ile Ser Asp Trp Asn Ser Leu Phe Trp Ile Ala His Pro
    290                 295                 300

Gly Gly Pro Ala Ile Leu Asp Ala Val Glu Ala Lys Leu Asn Leu Glu
305                 310                 315                 320

Lys Lys Lys Leu Glu Ala Thr Arg His Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Leu Lys Gly Glu Lys Ala Thr Thr Gly Glu Gly Leu Asp Trp Gly
        355                 360                 365

Val Leu Phe Gly Phe Gly Pro Gly Leu Thr Ile Glu Thr Val Val Leu
    370                 375                 380

His Ser Val Pro Thr Val Thr Asn
385                 390
```

<210> SEQ ID NO 64
<211> LENGTH: 1182
<212> TYPE: DNA
<213> ORGANISM: Vitis vinifera

<400> SEQUENCE: 64

```
atggcatccg tagaggagtt cagaaatgca cagagggcaa aaggtccagc aaccatattg      60
gctattggaa cagccacccc tgatcactgt gtttatcaat ctgattacgc tgattactat     120
ttcagagtaa ctaaaagtga acatatgaca gaacttaaga aaaagtttaa tagaatttgt     180
gataaatcta tgataaagaa aagatacata catctaactg aagaaatgtt agaggaacat     240
ccaaatatag gtgcatatat ggcaccatct ttgaatatta acaagaaat cataacagcc     300
gaggtaccta gactaggtag agacgcagcc ttgaaagctt taaggaatg gggacaacca     360
aaatctaaga ttacacattt ggttttctgt acaacttccg gtgtcgaaat gccaggtgct     420
gattataaac tagcaaacct attgggatta gagacctctg ttagaagagt tatgttgtat     480
catcaaggtt gttacgccgg aggtacagtg cttagaactg ctaaggattt ggcagaaaat     540
aacgccggtg ctagggtttt agtcgtctgc agtgaaatca ctgtcgtaac ttcagaggt      600
ccatcagaag atgctctaga cagtttggtc ggacaagcat tgtttggcga tggatcttcc     660
```

-continued

```
gccgtaattg taggcagcga tcctgatgtg tccattgaaa gaccactatt tcaattagtt        720
tctgctgctc aaacttttat tccaaattcc gccggtgcca tagcaggaaa cttgagagaa        780
gttggtttga cttttcattt gtggcctaat gtcccaacct taatttcaga aaacatcgaa        840
aaatgcttaa ctcaagcctt tgacccattg ggcataagcg actggaactc attgttttgg        900
attgctcatc caggtggtcc agcaatttta gacgcagtgg aggcaaaact aaacttagag        960
aagaaaaagt tggaagctac aagacacgtt ctatcagagt atggcaacat gagctctgcc       1020
tgcgttttat tcattctaga tgagatgagg aagaagtctt taaagggtga aaaagccaca       1080
accggagaag gtttagattg gggtgttcta tttggtttcg gtcctggctt aacaattgag       1140
acagtggtgt tacactctgt tccaactgtc actaactaat ga                          1182
```

METABOLICALLY ENGINEERED CELLS FOR THE PRODUCTION OF RESVERATROL OR AN OLIGOMERIC OR GLYCOSIDICALLY-BOUND DERIVATIVE THEREOF

This application is a continuation of U.S. application Ser. No. 12/081,571, filed Apr. 17, 2008 (now U.S. Pat. No. 9,040,269), which is a continuation in part of U.S. application Ser. No. 11/816,847, filed on Aug. 22, 2007 (now U.S. Pat. No. 8,895,287), which is the U.S. national stage of International Application No. PCT/EP2006/060154, filed on Feb. 21, 2006, which claims priority to Great Britain Patent Application No. 0503657.9 filed on Feb. 22, 2005, the disclosures of each of which are explicitly incorporated by reference in their entirety.

FIELD OF THE INVENTION

This invention relates generally to the production of the polyphenol resveratrol or an oligomeric or glycosidically bound derivative thereof such as its β-glucoside piceid using microbial cells. Furthermore, it relates to the use of naturally occurring or recombinant micro-organisms that produce resveratrol or such a derivative for production of food, feed and beverages.

BACKGROUND OF THE INVENTION

Production of chemicals from micro-organisms has been an important application of biotechnology. Typically, the steps in developing such a bio-production method may include 1) selection of a proper micro-organism host, 2) elimination of metabolic pathways leading to by-products, 3) deregulation of desired pathways at both enzyme activity level and the transcriptional level, and 4) overexpression of appropriate enzymes in the desired pathways. In preferred aspect, the present invention has employed combinations of the steps above to redirect carbon flow from phenylalanine or tyrosine through enzymes of the plant phenylpropanoid pathway which supplies the necessary precursor for the desired biosynthesis of resveratrol.

Resveratrol (or 3,4,5-trihydroxystilbene) is a phytophenol belonging to the group of stilbene phytoalexins, which are low-molecular-mass secondary metabolites that constitute the active defense mechanism in plants in response to infections or other stress-related events. Stilbene phytoalexins contain the stilbene skeleton (trans-1,2-diphenylethylene) as their common basic structure: that may be supplemented by addition of other groups as well (Hart and Shrimpton, 1979, Hart, 1981). Stilbenes have been found in certain trees (angio-sperms, gymnosperms), but also in some herbaceous plants (in species of the Myrtaceae, Vitaceae and Leguminosae families). Said compounds are toxic to pests, especially to fungi, bacteria and insects. Only few plants have the ability to synthesize stilbenes, or to produce them in an amount that provides them sufficient resistance to pests.

The synthesis of the basic stilbene skeleton is pursued by stilbene synthases. So far, two enzymes have been designated as a stilbene synthase; pinosylvine synthase and resveratrol synthase. To date, the groundnut (*Arachis hypogaea*) resveratrol synthase has been characterised in most detail, such that most of the properties are known (Schoppner and Kindl, 1984). Substrates that are used by stilbene synthases are malonyl-CoA, cinnamoyl-CoA or coumaroyl-CoA. These substances occur in every plant because they are used in the biosynthesis of other important plant constituents as well such as flavonoids, flower pigments and lipids. Resveratrol (FIG. 1 trans-form) consists of two closely connected phenol rings and belongs therefore to the polyphenols. While present in other plants, such as *eucalyptus*, spruce, and lily, and in other foods such as mulberries and peanuts, resveratrol's most abundant natural sources are *Vitis vinifera*, *-labrusca*, and *-muscadine* (*rotundifolia*) grapes, which are used to make wines. The compound occurs in the vines, roots, seeds, and stalks, but its highest concentration is in the skin (Celotti et al., 1996), which contains 50-100 µg/g. (Jang et al. 1997). During red wine vinification the grape skins are included in the must, in contrast to white wine vinification, and therefore resveratrol is found in small quantities in red wine only. Resveratrol has, besides its antifungal properties, been recognized for its cardioprotective- and cancer chemopreventive activities; it acts as a phytoestrogen, an inhibitor of platelet aggregation (Kopp et al, 1998; Gehm et al 1997; Lobo et al 1995), and an antioxidant (Jang et al., 1997; Huang 1997). These properties explain the so-called French Paradox, i.e. the wine-drinking French have a low incidence of coronary heart disease despite a low-exercise, high-fat diet. Recently it has been shown that resveratrol can also activate the SIR2 gene in yeast and the analogous human gene SIRT1, which both play a key role in extending life span. Ever since, attention is very much focused on the life-span extending properties of resveratrol (Hall, 2003, Couzin, 2004).

American health associations, such as the Life Extension Foundation, are promoting the vast beneficial effects of this drug, and thereby propelling the ideal conditions for a successful commercialisation. Present production processes rely mostly upon extraction of resveratrol, either from the skin of grape berries, or from Knot weed. This is a labour intensive process and generates low yield which, therefore, prompts an incentive for the development of novel, more efficient and high-yielding production processes.

In plants, the phenylpropanoid pathway is responsible for the synthesis of a wide variety of secondary metabolic compounds, including lignins, salicylates, coumarins, hydroxycinnamic amides, pigments, flavonoids and phytoalexins. Indeed formation of resveratrol in plants proceeds through the phenylpropanoid pathway. The amino acid L-phenylalanine is converted into trans-cinnamic acid through the non-oxidative deamination by L-phenylalanine ammonia lyase (PAL) (FIG. 2). Next, trans-cinnamic acid is hydroxylated at the para-position to 4-coumaric acid (4-hydroxycinnamic acid) by cinnamate-4-hydroxylase (C4H), a cytochrome P450 monooxygenase enzyme, in conjunction with NADPH:cytochrome P450 reductase (CPR). The 4-coumaric acid, is subsequently activated to 4-coumaroyl-CoA by the action of 4-coumarate-CoA ligase (4CL). Finally, resveratrol synthase (VST) catalyses the condensation of a phenylpropane unit of 4-coumaroyl-CoA with malonyl CoA, resulting in formation of resveratrol.

Recently, a yeast was disclosed that could produce resveratrol from 4-coumaric acid that is found in small quantities in grape must (Becker et al. 2003). The production of 4-coumaroyl-CoA, and concomitant resveratrol, in laboratory strains of *S. cerevisiae*, was achieved by co-expressing a heterologous coenzyme-A ligase gene, from hybrid poplar, together with the grapevine resveratrol synthase gene (vst1). The other substrate for resveratrol synthase, malonyl-CoA, is already endogenously produced in yeast and is involved in de novo fatty-acid biosynthesis. The study showed that cells of *S. cerevisiae* could produce minute amounts of resveratrol, either in the free form or in the glucoside-bound form, when cultured in synthetic media that was supplemented with 4-coumaric acid.

However, said yeast would not be suitable for a commercial application because it suffers from low resveratrol yield, and requires addition of 4-coumaric acid, which is only present in few industrial media. In order to facilitate and broaden the application of resveratrol as both a pharmaceutical and neutraceutical, it is therefore highly desirable to obtain a yeast that can produce resveratrol directly from glucose, without addition of 4-coumaric acid.

A recent study (Ro and Douglas, 2004) describes the reconstitution of the entry point of the phenylpropanoid pathway in *S. cerevisiae* by introducing PAL, C4H and CPR from Poplar. The purpose was to evaluate whether multienzyme complexes (MECs) containing PAL and C4H are functionally important at this entry point into phenylpropanoid metabolism. By feeding the recombinant yeast with [3H]-phenylalanine it was found that the majority of metabolized [3H]-phenylalanine was incorporated into 4-[3H]-coumaric acid, and that phenylalanine metabolism was highly reduced by inhibiting C4H activity. Moreover, PAL-alone expressers metabolized very little phenylalanine into cinnamic acid. When feeding [3H]-phenylalanine and [14C]-trans-cinnamic acid simultaneously to the triple expressers, no evidence was found for channeling of the endogenously synthesized [3H]-trans-cinnamic acid into 4-coumaric acid. Therefore, efficient carbon flux from phenylalanine to 4-coumaric acid via reactions catalyzed by PAL and C4H does not appear to require channeling through a MEC in yeast, and sheer biochemical coupling of PAL and C4H seems to be sufficient to drive carbon flux into the phenylpropanoid pathway. In yet another study (Hwang et al., 2003) production of plant-specific flavanones by *Escherichia coli* was achieved through expression of an artificial gene cluster that contained three genes of a phenyl propanoid pathway of various heterologous origins; PAL from the yeast *Rhodotorula rubra*, 4CL from the actinomycete *Streptomyces coelicolor*, and chalcone synthase (CHS) from the licorice plant *Glycyrrhiza echinata*. These pathways bypassed C4H, because the bacterial 4CL enzyme ligated coenzyme A to both trans-cinnamic acid and 4-coumaric acid. In addition, the PAL from *Rhodotorula rubra* uses both phenylalanine and tyrosine as the substrates. Therefore, *E. coli* cells containing the gene clusters and grown on glucose, produced small amounts of two flavanones, pinocembrin (0.29 g/l) from phenylalanine and naringenin (0.17 g/l) from tyrosine. In addition, large amounts of their precursors, 4-coumaric acid and trans-cinnamic acid (0.47 and 1.23 mg/liter respectively), were accumulated. Moreover, the yields of these compounds could be increased by addition of phenylalanine and tyrosine.

Whereas the enzyme from dicotylic plants utilizes only phenylalanine efficiently, several studies indicated that PAL from monocotylic plants, and some micro-organisms, utilizes tyrosine as well (Rösler et al., 1997). In such reactions the enzyme activity is designated tyrosine ammonia lyase (TAL, FIG. 3). Conversion of tyrosine by TAL results in the direct formation of 4-coumaric acid without the intermediacy of C4H and CPR. Mostly both activities reside on the same polypeptide and have very similar catalytic efficiencies, in spite of large differences in Km and turnover number. However, most PAL/TAL enzymes from plants prefer phenylalanine rather than tyrosine. The level of TAL activity is mostly lower than PAL activity, but the magnitude of this difference varies over a wide range. For example, the parsley enzyme has a Km for phenylalanine of 15-25 µM and for tyrosine 2.0-8.0 mM with turnover numbers 22 $s^{-1}$ and 0.3 $s^{-1}$ respectively. In contrast, the maize enzyme has a Km for phenylalanine only 15-fold higher than for tyrosine, and turnover numbers about 10-fold higher. Moreover, in the red yeasts, *Rhodotorula glutinis* (*Rhodosporidium toruloides*) and *-rubra*, the TAL catalytic activity is close to the PAL catalytic activity with a ratio of TAL/PAL of approximately 0.58. It is believed that the PAL enzyme in these yeasts degrades phenylalanine as a catabolic function and the trans-cinnamic acid formed is converted to benzoate and other cellular materials, whereas in plants it is thought to be merely a regulatory enzyme in the biosynthesis of lignin, isoflavonoids and other phenylpropanoids.

Recently, an open reading frame was found in the bacterium *Rhodobacter capsulatus* that encodes a hypothetical biosynthetic tyrosine ammonia lyase (TAL) that is involved in the biosynthesis of the chromophore of the photoactive yellow protein (Kyndt et al., 2002). This was the first time that a PAL-homologous gene was found in bacteria. The TAL gene was isolated and overproduced in *Escherichia coli*. The Km and kcat values for the conversion of tyrosine to 4-coumaric acid were 15.6 µM and 27.7 $s^{-1}$ respectively, and for conversion of L-phenylalanine to trans-cinnamic acid were 1277 µM and 15.1 $s^{-1}$ respectively. As a consequence of the smaller Km and a slightly larger kcat, the enzyme shows a strong preference for tyrosine over L-phenylalanine, with a catalytic efficiency (Km/kcat) for tyrosine of approximately 150-fold larger than for phenylalanine. The kinetic studies established that tyrosine, and not L-phenylalanine, is the natural substrate of the enzyme under physiological conditions. Very recently a study described the heterologous coexpression of phenylalanine ammonia lyase, cinnamate-4-hydroxylase, 4-coumarate-Coa-ligase and chalcone synthase, for the production of flavonoids in *E. coli* (Watts et al., 2004). The simultaneous expression of all four genes, however, was not successful because of a nonfunctional cinnamate-4-hydroxylase. The substitution of phenylalanine ammonia lyase and cinnamate-4-hydroxylase by a new tyrosine ammonia lyase that was cloned from *Rhodobacter sphaeroides*, could, however, solved the problem and led to high-level production of the flavonone naringenin. Furthermore, said tyrosine ammonia lyase from *Rhodobacter sphaeroides* is also used for heterologous production of 4-coumaric acid (i.e. para-hydroxycinnamic acid) in *Escherichia coli* (US-A-2004059103). Evenmore, further methods for development of a biocatalyst for conversion of glucose into 4-coumaric acid are described. US-A-2004023357 discloses a tyrosine ammonia lyase from the yeast *Trichosporon cutaneum* for the production of coumaric acid in *Escherichia coli* and *Saccharomyces cerevisiae*. US-A-2001053847 describes the incorporation of the wild type PAL from the yeast *Rhodotorula glutinis* into *E. coli*, underlining the ability of the wildtype PAL to convert tyrosine directly to 4-coumaric acid. Moreover, there is also exemplification of incorporation of the wildtype PAL from the yeast *Rhodotorula glutinis*, plus a plant C4H and CPR into *E. coli* and *S. cerevisiae*. Also described is the development of a biocatalyst through mutagenesis of the wild type yeast PAL *Rhodotorula glutinis* with enhanced TAL activity (U.S. Pat. No. 6,521,748). Neither of the aforementioned patents claim the incorporation of 4CL and VST for the production of resveratrol.

Recently, evidence was shown that the filamentous fungi *A. oryzae* contained the enzyme chalcone synthase (CHS) that is normally involved in the biosynthesis of flavonoids, such as naringenin, in plants (Seshime et al., 2005). Indeed it was also shown that *A. oryzae* contained the major set of genes responsible for phenylpropanoid-flavonoid metabolism, i.e PAL, C4H and 4CL. However, there is no evidence that *A. oryzae* contained a stilbene synthase such as resveratrol synthase.

The present invention now provides a micro-organism having an operative metabolic pathway comprising at least one enzyme activity, said pathway producing 4-coumaric acid and producing resveratrol therefrom or an oligomeric or glycosidically-bound derivative thereof. Such a micro-organism may be naturally occurring and may be isolated by suitable screening procedures, but more preferably is genetically engineered.

Preferably, said resveratrol or derivative is produced in a reaction catalysed by an enzyme in which endogenous malonyl-CoA is a substrate, and preferably said resveratrol is produced from 4-coumaroyl-CoA.

Said resveratrol or derivative is preferably produced from 4-coumaroyl-CoA by a resveratrol synthase which is preferably expressed in said micro-organism from nucleic acid coding for said enzyme which is not native to the micro-organism.

Generally herein, unless the context implies otherwise, references to resveratrol include reference to oligomeric or glycosidically bound derivatives thereof, including particularly piceid.

Thus, in certain preferred embodiments, said resveratrol synthase is a resveratrol synthase (EC 2.3.1.95) from a plant belonging to the genus of *Arachis*, e.g. *A. glabatra, A. hypogaea*, a plant belonging to the genus of *Rheum*, e.g. *R. tataricum*, a plant belonging to the genus of *Vitus*, e.g. *V. labrusca, V. riparaia, V. vinifera*, or any one of the genera *Pinus, Piceea, Lilium, Eucalyptus, Parthenocissus, Cissus, Calochortus, Polygonum, Gnetum, Artocarpus, Nothofagus, Phoenix, Festuca, Carex, Veratrum, Bauhinia* or *Pterolobium*.

Preferably, said 4-coumaric acid is produced from trans-cinnamic acid, suitably by an enzyme in a reaction catalysed by said enzyme in which oxygen is a substrate, NADH or NADPH is a cofactor and NAD$^+$ or NADP$^+$ is a product.

Thus, said 4-coumaric acid may be produced from trans-cinnamic acid by a cinnamate 4-hydroxylase, which preferably is expressed in said micro-organism from nucleic acid coding for said enzyme which is not native to the micro-organism.

In certain preferred embodiments, including those referred to in the paragraphs above, said cinnamate-4-hydroxylase is a cinnamate-4-hydroxylase (EC 1.14.13.11) from a plant or a micro-organism. The plant may belong to the genus of *Arabidopsis*, e.g. *A. thaliana*, a plant belonging to the genus of *Citrus*, e.g. *C. sinensis, C. x paradisi*, a plant belonging to the genus of *Phaseolus*, e.g. *P. vulgaris*, a plant belonging to the genus of *Pinus*, e.g. *P. taeda*, a plant belonging to the genus of *Populus*, e.g. *P. deltoides, P. tremuloides, P. trichocarpa*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Ammi, Avicennia, Camellia, Camptotheca, Catharanthus, Glycine, Helianthus, Lotus, Mesembryanthemum, Physcomitrella, Ruta, Saccharum, Vigna*. The micro-organism might be a fungus belonging to the genus *Aspergillus*, e.g. *A. oryzae*.

Preferably, said 4-coumaric acid is produced from tyrosine in a reaction catalysed by an enzyme in which ammonia is produced and suitably said 4-coumaric acid is produced from tyrosine by a L-phenylalanine ammonia lyase or a tyrosine ammonia lyase, e.g. tyrosine ammonia lyase (EC 4.3.1.5) from yeast or bacteria. Suitably, the tyrosine ammonia lyase is from the yeast *Rhodotorula rubra* or from the bacterium *Rhodobacter capsulatus*.

Optionally, said tyrosine ammonia lyase is expressed in said micro-organism from nucleic acid coding for said enzyme which is not native to the micro-organism.

Alternatively, said trans-cinnamic acid may be produced from L-phenylalanine in a reaction catalysed by an enzyme in which ammonia is produced and suitably said trans-cinnamic acid is formed from L-phenylalanine by a phenylalanine ammonia lyase.

In certain preferred embodiments, said L-phenylalanine ammonia lyase is a L-phenylalanine ammonia lyase (EC 4.3.1.5) from a plant or a micro-organism. The plant may belong to the genus of *Arabidopsis*, e.g. *A. thaliana*, a plant belonging to the genus of *Brassica*, e.g. *B. napus, B. rapa*, a plant belonging to the genus of *Citrus*, e.g. *C. reticulata, C. clementinus, C. limon*, a plant belonging to the genus of *Phaseolus*, e.g. *P. coccineus, P. vulgaris*, a plant belonging to the genus of *Pinus*, e.g. *P. banksiana, P. monticola, P. pinaster, P. sylvestris, P. taeda*, a plant belonging to the genus of *Populus*, e.g. *P. balsamifera, P. deltoides, P. Canadensis, P. kitakamiensis, P. tremuloides*, a plant belonging to the genus of *Solanum*, e.g. *S. tuberosum*, a plant belonging to the genus of *Prunus*, e.g. *P. avium, P. persica*, a plant belonging to the genus of *Vitus*, e.g. *Vitus vinifera*, a plant belonging to the genus of *Zea*, e.g. *Z. mays* or other plant genera e.g. *Agastache, Ananas, Asparagus, Bromheadia, Bambusa, Beta, Betula, Cucumis, Camellia, Capsicum, Cassia, Catharanthus, Cicer, Citrullus, Coffea, Cucurbita, Cynodon, Daucus, Dendrobium, Dianthus, Digitalis, Dioscorea, Eucalyptus, Gallus, Ginkgo, Glycine, Hordeum, Helianthus, Ipomoea, Lactuca, Lithospermum, Lotus, Lycopersicon, Medicago, Malus, Manihot, Medicago, Mesembryanthemum, Nicotiana, Olea, Oryza, Pisum, Persea, Petroselinum, Phalaenopsis, Phyllostachys, Physcomitrella, Picea, Pyrus, Quercus, Raphanus, Rehmannia, Rubus, Sorghum, Sphenostylis, Stellaria, Stylosanthes, Triticum, Trifolium, Triticum, Vaccinium, Vigna, Zinnia*. The micro-organism might be a fungus belonging to the genus *Agaricus*, e.g. *A. bisporus*, a fungus belonging to the genus *Aspergillus*, e.g. *A. oryzae, A. nidulans, A. fumigatus*, a fungus belonging to the genus *Ustilago*, e.g. *U. maydis*, a bacterium belonging to the genus *Rhodobacter*, e.g. *R. capsulatus*, a yeast belonging to the genus *Rhodotorula*, e.g. *R. rubra*.

Suitably, said L-phenylalanine ammonia lyase is expressed in said micro-organism from nucleic acid coding for said enzyme which is not native to the micro-organism.

Preferably, 4-coumaroyl-CoA is formed in a reaction catalysed by an enzyme in which ATP and CoA are substrates and ADP is a product and suitably 4-coumaroyl-CoA is formed in a reaction catalysed by a 4-coumarate-CoA ligase.

Said 4-coumarate-CoA ligase may be a 4-coumarate-CoA ligase (EC 6.2.1.12) from a plant, a micro-organism or a nematode. The plant may belong to the genus of *Abies*, e.g. *A. beshanzuensis, B. firma, B. holophylla*, a plant belonging to the genus of *Arabidopsis*, e.g. *A. thaliana*, a plant belonging to the genus of *Brassica*, e.g. *B. napus, B. rapa, B. oleracea*, a plant belonging to the genus of *Citrus*, e.g. *C. sinensis*, a plant belonging to the genus of *Larix*, e.g. *L. decidua, L. gmelinii, L. griffithiana, L. himalaica, L. kaempferi, L. laricina, L. mastersiana, L. occidentalis, L. potaninii, L. sibirica, L. speciosa*, a plant belonging to the genus of *Phaseolus*, e.g. *P. acutifolius, P. coccineus*, a plant belonging to the genus of *Pinus*, e.g. *P. armandii P. banksiana, P. pinaster*, a plant belonging to the genus of *Populus*, e.g. *P.*

*balsamifera, P. tomentosa, P. tremuloides*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Agastache, Amorpha, Cathaya, Cedrus, Crocus, Pestuca, Glycine, Juglans, Keteleeria, Lithospermum, Lolium, Lotus, Lycopersicon, Malus, Medicago, Mesembryanthemum, Nicotiana, Nothotsuga, Oryza, Pelargonium, Petroselinum, Rhyscomitrella, Picea, Prunus, Pseudolarix, Pseudotsuga, Rosa, Rubus, Ryza, Saccharum, Suaeda, Thellungiella, Triticum, Tsuga*. The micro-organism might be a filamentous fungi belonging to the genus *Aspergillus*, e.g. *A. flavus, A. nidulans, A. oryzae, A. fumigatus*, a filamentous fungus belonging to the genus *Neurospora*, e.g. *N. crassa*, a fungus belonging to the genus *Yarrowia*, e.g. *Y. lipolytica*, a fungus belonging to the genus of *Mycosphaerella*, e.g. *M. graminicola*, a bacterium belonging to the genus of *Mycobacterium*, e.g. *M. bovis, M. leprae, M. tuberculosis*, a bacterium belonging to the genus of *Neisseria*, e.g. *N. meningitidis*, a bacterium belonging to the genus of *Streptomyces*, e.g. *S. coelicolor*, a bacterium belonging to the genus of *Rhodobacter*, e.g. *R. capsulatus*, a nematode belonging to the genus *Ancylostoma*, e.g. *A. ceylanicum*, a nematode belonging to the genus *Caenorhabditis*, e.g. *C. elegans*, a nematode belonging to the genus *Haemonchus*, e.g. *H. contortus*, a nematode belonging to the genus *Lumbricus*, e.g. *L. rubellus*, a nematode belonging to the genus *Meloidogyne*, e.g. *M. hapla*, a nematode belonging to the genus *Strongyloidus*, e.g. *S. rattii, S. stercoralis*, a nematode belonging to the genus *Pristionchus*, e.g. *P. pacificus*.

Optionally, a NADPH:cytochrome P450 reductase (CPR) has been recombinantly introduced into said micro-organism. This may be a plant CPR introduced into a non-plant micro-organism. Alternatively, a native NADPH:cytochrome P450 reductase (CPR) has been overexpressed in said micro-organism.

In certain preferred embodiments, including those referred to in the paragraphs above, said NADPH:cytochrome P450 reductase is a NADPH:cytochrome P450 reductase (EC 1.6.2.4) from a plant belonging to the genus of *Arabidopsis*, e.g. *A. thaliana*, a plant belonging to the genus of *Citrus*, e.g. *C. sinensis, C. x paradisi*, a plant belonging to the genus of *Phaseolus*, e.g. *P. vulgaris*, a plant belonging to the genus of *Pinus*, e.g. *P. taeda*, a plant belonging to the genus of *Populus*, e.g. *P. deltoides, P. tremuloides, P. trichocarpa*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Ammi, Avicennia, Camellia, Camptotheca, Catharanthus, Glycine, Helianthus, Lotus, Mesembryanthemum, Physcomitrella, Ruta, Saccharum, Vigna*.

Whilst the micro-organism may be naturally occurring, preferably at least one copy of at least one genetic sequence encoding a respective enzyme in said metabolic pathway has been recombinantly introduced into said micro-organism.

Additionally or alternatively to introducing coding sequences coding for a said enzyme, one may provide one or more expression signals, such as promoter sequences, not natively associated with said coding sequence in said organism. Thus, optionally, at least one copy of a genetic sequence encoding a tyrosine ammonia lyase is operatively linked to an expression signal not natively associated with said genetic sequence in said organism, and/or at least one copy of a genetic sequence encoding a L-phenylalanine ammonia lyase is operatively linked to an expression signal not natively associated with said genetic sequence in said organism.

Optionally, at least one copy of a genetic sequence encoding cinnamate 4-hydroxylase, whether native or not, is operatively linked to an expression signal not natively associated with said genetic sequence in said organism.

Optionally, at least one copy of a genetic sequence encoding a 4-coumarate-CoA ligase, whether native or not, is operatively linked to an expression signal not natively associated with said genetic sequence in said organism.

Optionally, at least one copy of a genetic sequence encoding a resveratrol synthase, whether native or not, is operatively linked to an expression signal not natively associated with said genetic sequence in said organism.

Expression signals include nucleotide sequences located upstream (5' non-coding sequences), within, or downstream (3' non-coding sequences) of a coding sequence, and which influence the transcription, RNA processing or stability, or translation of the associated coding sequence. Such sequences may include promoters, translation leader sequences, introns, and polyadenylation recognition sequences.

In certain aspects the invention provides a metabolically engineered micro-organism having an operative metabolic pathway in which a first metabolite is transformed into a second metabolite in a reaction catalysed by a first enzyme, said reaction step producing ammonia, and in which said second metabolite is transformed into a third metabolite in a reaction catalysed by a second enzyme, in which oxygen is a substrate, NADPH or NADH is a cofactor and $NADP^+$ or $NAD^+$ is a product, and in which said third metabolite is transformed into a fourth metabolite in a reaction catalysed by a third enzyme in which ATP and CoA is a substrate, and ADP is a product, and in which said fourth metabolite is transformed into a fifth metabolite in a reaction catalysed by a fourth enzyme in which endogenous malonyl-CoA is a substrate.

The present invention also provides a metabolically engineered micro-organism having an operative metabolic pathway in which a first metabolite is transformed into a said third metabolite catalysed by a first enzyme, said reaction step producing ammonia, without the involvement of said second enzyme, and in which said third metabolite is transformed into a said fourth metabolite in a reaction catalysed by a said third enzyme in which ATP and CoA is a substrate, and ADP is a product, and in which said fourth metabolite is transformed into a said fifth metabolite in a reaction catalysed by a said fourth enzyme in which endogenous malonyl-CoA is a substrate.

The micro-organisms described above include ones containing one or more copies of an heterologous DNA sequence encoding phenylalanine ammonia lyase operatively associated with an expression signal, and containing one or more copies of an heterologous DNA sequence encoding cinnamate-4-hydroxylase operatively associated with an expression signal, and containing one or more copies of an heterologous DNA sequence encoding 4-coumarate-CoA-ligase operatively associated with an expression signal, and containing one or more copies of an heterologous DNA sequence encoding resveratrol synthase operatively associated with an expression signal.

They include also ones lacking cinnamate-4-hydroxylase activity, and containing one or more copies of a heterologous DNA sequence encoding tyrosine ammonia lyase operatively associated with an expression signal, and containing one or more copies of an heterologous DNA sequence encoding 4-coumarate-CoA-ligase operatively associated with an expression signal, and containing one or more copies of an heterologous DNA sequence encoding resveratrol synthase operatively associated with an expression signal.

In the present context the term "micro-organism" relates to microscopic organisms, including bacteria, microscopic fungi, including yeast.

More specifically, the micro-organism may be a fungus, and more specifically a filamentous fungus belonging to the genus of *Aspergillus*, e.g. *A. niger, A. awamori, A. oryzae, A. nidulans*, a yeast belonging to the genus of *Saccharomyces*, e.g. *S. cerevisiae, S. kluyveri, S. bayanus, S. exiguus, S. sevazzi, S. uvarum*, a yeast belonging to the genus *Kluyveromyces*, e.g. *K. lactis K. marxianus* var. *marxianus, K. thermotolerans*, a yeast belonging to the genus *Candida*, e.g. *C. utilis C. tropicalis, C. albicans, C. lipolytica, C. versatilis*, a yeast belonging to the genus *Pichia*, e.g. *P. stipidis, P. pastoris, P. sorbitophila*, or other yeast genera, e.g. *Cryptococcus, Debaromyces, Hansenula, Pichia, Yarrowia, Zygosaccharomyces* or *Schizosaccharomyces*. Concerning other micro-organisms a non-exhaustive list of suitable filamentous fungi is supplied: a species belonging to the genus *Penicillium, Rhizopus, Fusarium, Fusidium, Gibberella, Mucor, Mortierella, Trichoderma*.

Concerning bacteria a non-exhaustive list of suitable bacteria is given as follows: a species belonging to the genus *Bacillus*, a species belonging to the genus *Escherichia*, a species belonging to the genus *Lactobacillus*, a species belonging to the genus *Lactococcus*, a species belonging to the genus *Corynebacterium*, a species belonging to the genus *Acetobacter*, a species belonging to the genus *Acinetobacter*, a species belonging to the genus *Pseudomonas*, etc.

The preferred micro-organisms of the invention may be *S. cerevisiae, A. niger, A. oryzae, E. coli, L. lactis* or *B. subtilis*.

The constructed and engineered micro-organism can be cultivated using commonly known processes, including chemostat, batch, fed-batch cultivations, etc.

Thus, the invention includes a method for producing resveratrol or an oligomeric or glycosidically-bound derivative thereof comprising contacting a non-plant cell with a carbon substrate in the substantial absence of an external source of 4-coumaric acid, said cell having the capacity to produce resveratrol or an oligomeric or glycosidically-bound derivative thereof under the conditions, in which the micro-organism may be selected from the group consisting of fungi and bacteria, especially yeast.

Said carbon substrate is optionally selected from the group of fermentable carbon substrates consisting of monosaccharides, oligosaccharides and polysaccharides, e.g. glucose, fructose, galactose, xylose, arabinose, mannose, sucrose, lactose, erythrose, threose, and/or ribose. Said carbon substrate may additionally or alternatively be selected from the group of non-fermentable carbon substrates including ethanol, acetate, glycerol, and/or lactate. Said non-fermentable carbon substrate may additionally or alternatively be selected from the group of amino acids and may be phenylalanine and/or tyrosine.

In an alternative aspect, the invention includes a method for producing resveratrol or an oligomeric or glycosidically-bound derivative thereof through heterologous expression of nucleotide sequences encoding phenylalanine ammonia lyase, cinnamate 4-hydroxylase, 4-coumarate-CoA ligase and resveratrol synthase and also a method for producing resveratrol through heterologous expression of nucleotide sequences encoding tyrosine ammonia lyase, 4-coumarate-CoA ligase and resveratrol synthase.

The invention as described above has allowed the production of yeast cells producing high levels of resveratrol. Accordingly, the invention includes a micro-organism composition comprising micro-organism cells and at least 0.4 μg/g resveratrol on a dry weight basis produced in said micro-organism cells, preferably comprising at least 0.5 μg/g of said resveratrol, more preferably at least 200 μg/g. The stated level of resveratrol can be found in the yeast cells themselves. The composition may essentially consist of said yeast cells.

The resveratrol producing microorganisms described above and the pinosylvin producing organisms described in WO2008/009728 could desirably be improved to produce higher yields by redirecting the flux through the metabolism of the microorganism.

One option is to increase the amount malonyl-CoA available for further conversion into pinosylvin and resveratrol or other stilbenoids. Increasing the amount of malonyl-CoA will have a positive effect on the production of all stilbenes of the type given in formula I

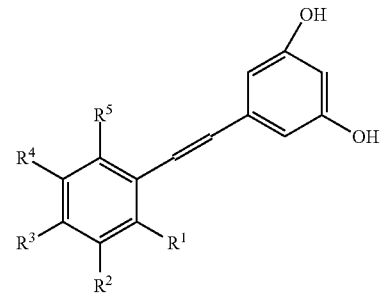

Formula 1

R1, R2, R3, R4, and R5 independently are either —H or —OH because malonyl-CoA is responsible for the upper ring. The stilbene that is produced depends on the other organic acid component involved, where cinnamic acid gives pinosylvin and coumaric acid gives resveratrol. Caffeic acid will give piceatannol.

By increasing the amount of available malonyl-CoA the yield of stilbenoid can be increased. A first method involves overexpression of ACC1 to create the increased supply.

Thus, the invention further includes a recombinant microorganism having an operative metabolic pathway in which one or more stilbenes according to the general formula I:

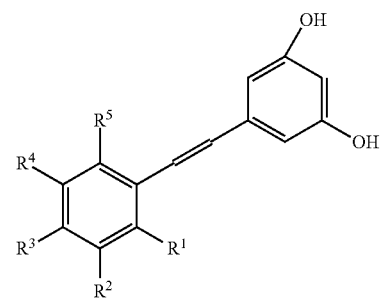

are formed from a precursor optionally hydroxy-substituted phenyl-2-propenoic acid or ester thereof and malonyl-CoA by the action of a stilbene synthase, wherein the amount of malonyl-CoA available for use in said pathway has been increased by providing more than a native expression level of an enzyme catalysing the reaction $$ATP+acetyl\text{-}CoA+HCO3\text{-}=ADP+phosphate\text{-}+malonyl\text{-}CoA.$$

Preferably, said more than native expression level of said enzyme has been provided by replacing a native promoter of a gene expressing said enzyme with a promoter providing a higher level of expression. For instance, said native promoter is replaced with a strong constitutive yeast promoter. The strong constitutive promoter may be the promoter of one of the yeast genes TDH3, ADH1, TPI1, ACT1, GPD, TEF1, TEF2, and PGI. The promoter may optionally be native to the yeast in which stilbenoid production is to be produced.

Alternatively or additionally, said more than native expression level of said enzyme has been provided by recombinantly introducing into said micro-organism at least one exogenous genetic sequence encoding a said enzyme. This may be an acetyl coenzymeA carboxylase (ACC1—EC No. 6.4.1.2).

A second and independent strategy which also increases the yield of the stilbenes is overexpression of CPR.

Thus, the micro-organism may be recombinantly engineered to produce more than a native amount of a cytochrome P450 reductase (CPR). This may be by replacing a native promoter of a gene expressing said CPR with a promoter providing a higher level of expression, for instance with a strong constitutive yeast promoter such as the promoter of one of the yeast genes TDH3, ADH1, TPI1, ACT1 GPD, TEF1, TEF2, and PGI, which optionally may be native to the yeast itself.

The micro-organism may comprise recombinantly introduced genes expressing a phenylalanine ammonia lyase, a cinnamate 4-hydroxylase and/or a coumarate-CoA ligase or appropriate enzymes for other stilbenes.

Effect of Overexpressing ACC1

Acetyl CoenzymeA carboxylase (ACC1 EC-Number 6.4.1.2) generates malonyl-CoA according to the below reaction:
[ACC1 Reaction]

$$ATP+acetyl\text{-}CoA+HCO3\text{-}=ADP+phosphate\text{-}+malonyl\text{-}CoA$$

By overexpressing ACC1 more malonyl-CoA is built up and this extra pool of malonyl-CoA is expected to generate more stilbenoids since the stilbene synthase reaction requires malonyl-CoA as building block for stilbene synthesis according to the reactions below:
[Resveratrol Synthase Reaction EC-Number 2.3.1.95]

$$3 \text{ malonyl-CoA}+4\text{-coumaroyl-CoA}=4\text{CoA}+3,4',5\text{-trihydroxystilbene}+4\text{CO2}$$

[Stilbene Synthase Reaction]

$$3 \text{ malonyl-CoA}+\text{cinnamoyl-CoA}=4\text{CoA}+3,5\text{-dihydroxystilbene}+4\text{CO2}$$

[General for any Hydroxyl Stilbene Synthase]

$$3 \text{ malonyl-CoA}+\text{hydroxycinnamoyl-CoA}=4\text{CoA}+\text{hydroxystilbene}+4\text{CO2}$$

Other appropriate organic acids substituting for 4-coumaroyl-CoA produce other stilbenoids.
Effect of Overexpressing CPR Hydroxylases, such as cinnamate 4-hyroxylase (1.14.13.11), are cytochrome P450 monooxygenases that catalyse the insertion of one atom of oxygen into an organic substrate while the other oxygen atom is reduced to water. This reaction requires NADPH according to the below reaction for the hydroxylation of cinnamic acid:

$$\text{trans-cinnamic acid}+NADPH+H^++O_2=4\text{-hydroxycinnamic acid}+NADP^++H_2O$$

The active site of cytochrome P450 hydroxylases contains a heme iron center. The iron is tethered to the protein via a thiolate ligand derived from a cysteine residue. In general the mechanism is as follows:
1. The resting state of the protein is as oxidized $Fe3+$.
2. Binding of the substrate, cinnamic acid, initiates electron transport and oxygen binding.
3. Electrons are supplied to the p450 hydroxylase by another protein, either cytochrome P450 reductase (CPR), ferredoxins, or cytochrome b5 to reduce the heme iron.
4. Molecular oxygen is bound and split by the now reduced iron.
5. An iron-bound oxidant, oxidizes the substrate to an alcohol or an epoxide, regenerating the resting state of the p450 hydroxylase.

As described above CPR act as an electron carrier and donor for the NADPH dependent cytochrome P450 hydroxylase reaction. Thus by overexpressing CPR more electrons (NADPH) are generated for the NADPH dependent hydroxylation leading to more coumaric acid, and as a consequence more coumaric acid leads to more resveratrol by the resveratrol pathway. Similar considerations apply in the production of other stilbenoids.

Resveratrol or an oligomeric or glycosidically-bound derivative thereof or other stilbenoids so produced may be used as a nutraceutical in a dairy product or a beverage such as beer.

Resveratrol produced according to the invention may be cis-resveratrol or trans-resveratrol, but it is to be expected that the trans- form will normally predominate, as with other stilbenoids.

BRIEF DESCRIPTION OF THE DRAWINGS

To assist in the ready understanding of the above description of the invention reference has been made to the accompanying drawings in which.

Figure 1:
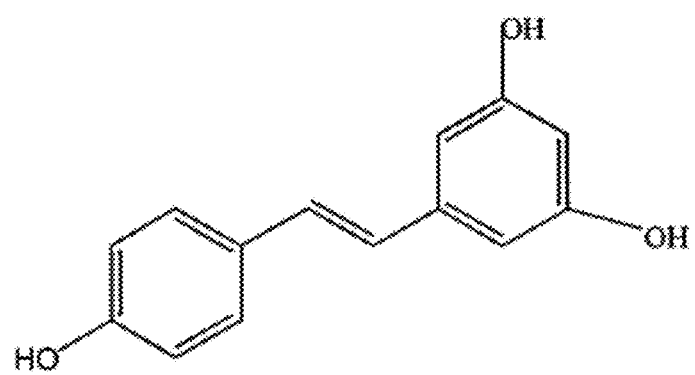
FIG. 1 shows the chemical structure of trans-resveratrol.
Figure 2:
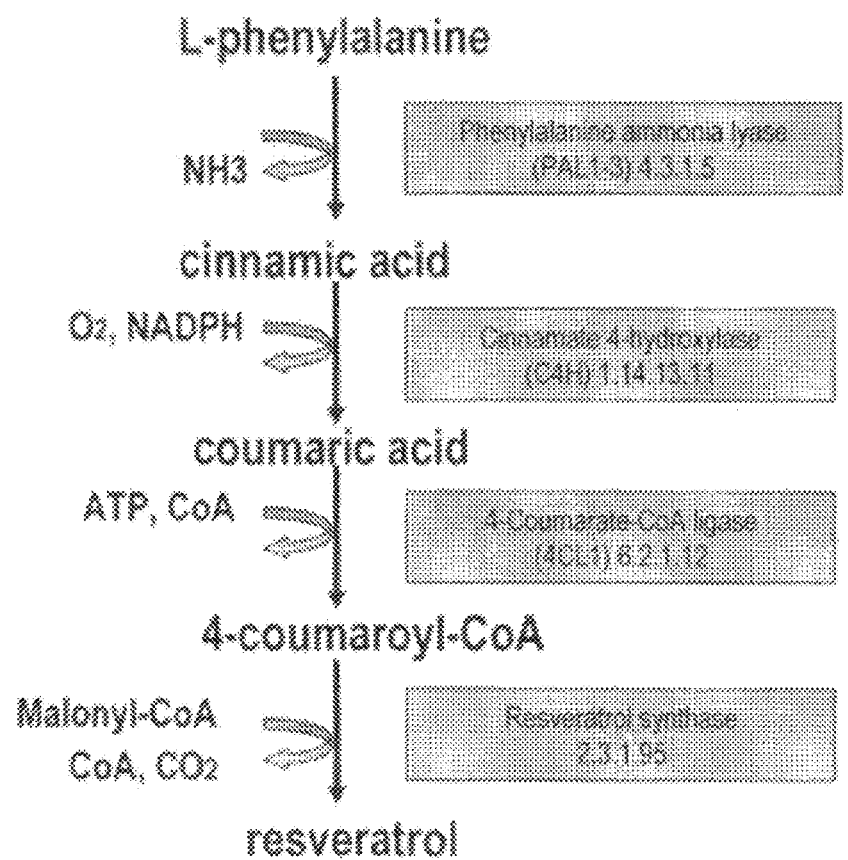
FIG. 2 shows the phenylpropanoid pathway utilising phenylalanine ammonia lyase acting on L-phenylalanine.
Figure 3:
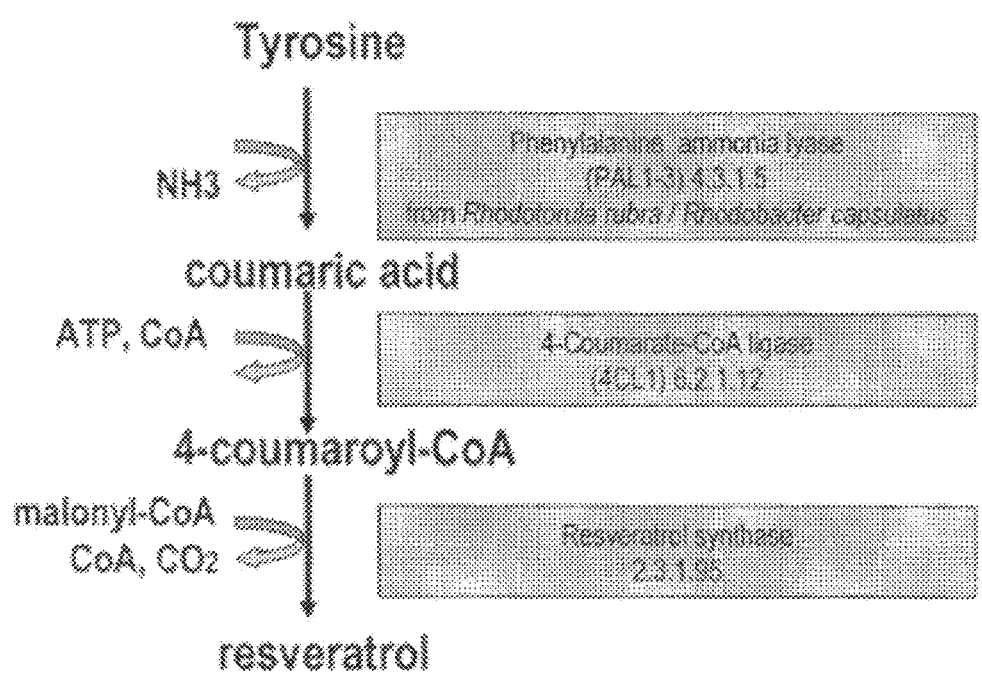
FIG. 3 shows the alternative pathway utilising phenylalanine ammonia lyase acting on L-tyrosine.

The invention will be further described and illustrated by the following non-limiting examples.

EXAMPLES

Example 1

Isolation of Genes Encoding PAL, TAL, C4H, CPR, 4CL, and VST

Phenylalanine ammonia lyase (PAL2) (Cochrane et al., 2004; SEQ ID NO: 1, 2), cinnamate 4-hydroxylase (C4H) (Mizutani et al., 1997; SEQ ID NO: 3, 4) and 4-coumarate:CoenzymeA ligase (4CL1) (Hamberger and Hahlbrock 2004; Ehlting et al., 1999; SEQ ID NO: 5, 6) were isolated via PCR from *A. thaliana* cDNA (BioCat, Heidelberg, Germany) using the primers in table 1. PAL2 and 4CL1 were chosen amongst several *A. thaliana* homologues due to favourable kinetic parameters towards cinnamic acid and coumaroyl-CoA, respectively (Cochrane et al., 2004; Hamberger and Hahlbrock 2004; Ehlting et al., 1999).

The coding sequence of resveratrol synthase (VST) from *Rheum tataricum* (Samappito et al., 2003; SEQ ID NO: 7, 8) and tyrosine ammonia lyase (TAL) from *Rhodobacter capsulatus* (Kyndt et al., 2002; SEQ ID NO: 11, 12) were codon optimized for expression in *S. cerevisiae* using the online service backtranslation tool at www.entelechon.com, yielding sequence SEQ ID NO: 9, 10 and SEQ ID NO: 13, 14 respectively. Oligos for the synthetic gene assembly were constructed at MWG Biotech and the synthetic gene was assembled by PCR using a slightly modified method protocol of from Martin et al. (2003) described below.

Primers from MWG for the assembly of the synthetic gene were dissolved in milliQ-water to a concentration of 100 pmole/µl. An aliquot of 5 µl of each primer was combined in a totalmix and then diluted 10-fold with milliQ water. The gene was assembled via PCR using 5 µl diluted totalmix per 50 µl as template for fusion DNA polymerase (Finnzymes). The PCR programme was as follows: Initial 98° C. for 30 s., and then 30 cycles with 98° C. for 10 s., 40° C. for 1 min. and 72° C. at 1 min./1000 basepairs, and a final 72° C. for 5 min. From the resulting PCR reaction, 20 µl was purified on 1% agarose gel. The result was a PCR smear and the regions around the wanted size were cut out from agarose gel and purified using the QiaQuick Gel Extraction Kit (Qiagen). A final PCR with the outer primers (for TAL and VST) in table 1 rendered the required TAL and VST genes. Point mutations were corrected using either the Quickchange site directed mutagenesis II kit (Stratagene, La Jolla, Calif.), or using PCR from overlapping error free DNA stretches from several different *E. coli* subclones.

NADPH:Cytochrome P450 reductase (CPR) from *A. thaliana* (AR2) (Mizutani and Ohta, 1998; SEQ ID NO: 17, 18) and from *S. cerevisiae* (CPR1) (Aoyama et al., 1978; SEQ ID NO: 15, 16), were isolated from *A. thaliana* cDNA (BioCat, Heidelberg, Germany) and *S. cerevisae* genomic DNA, respectively, using the primers in table 1.

Example 2

Construction of a Yeast Vector for Expression of PAL

The gene encoding PAL, isolated as described in example 1, was reamplified by PCR using forward- and reverse primers, with 5' overhangs containing EcoR1 and Spe1 restriction sites (table 1). The amplified PAL PCR product was digested with EcoR1/Spe1 and ligated into EcoR1/Spe1 digested pESC-URA vector (Stratagene), resulting in vector pESC-URA-PAL. The sequence of the gene was verified by sequencing of two different clones.

TABLE 1

Primers and restriction sites for the amplification of genes

| Primer for amplification of gene* (Restriction sites are underlined) | Gene | Restriction site: primer | Restriction site: vector |
|---|---|---|---|
| 5'-CG<u>GAATTC</u>TCATGGATCAAATCGAAGCAATGTT | PAL2 | EcoR1 | EcoR1 |
| 5'-CG<u>ACTAGT</u>TTAGCAAATCGGAATCGGAGC | PAL2 | Spe1 | Spe1 |
| 5'-CG<u>CTCGAG</u>AT ATGGACCTCCTCTTGCTGGA | C4H | Xho1 | Xho1 |
| 5'-CG<u>GGTACC</u>TTAACAGTTCCTTGGTTTCATAAC | C4H | Kpn1 | Kpn1 |
| 5'-GC<u>TCTAGA</u>CCT ATGGCGCCACAAGAACAAGCAGTTT | 4CL1 | Xba1 | Spe1 |
| 5'-GC<u>GGATCC</u>CCT TCACAATCCATTTGCTAGTTT TGCC | 4CL1 | BamH1 | BglII |
| 5'-CC <u>GGATCC</u>AAATGGCCCCAGAAGAGAGCAGG | VST | BamH1 | BamH1 |
| 5'-CG <u>CTCGAG</u>TTAAGTGATCAATGGAACCGAAGACAG | VST | Xho1 | Xho1 |
| 5'-CC<u>GAATTC</u>CCATGACCCTGCAATCTCAAACAGCTAAAG | TAL | EcoR1 | EcoR1 |
| 5'-CC<u>ACTAGT</u>TTAAGCAGGTGGATCGGCAGCT | TAL | Spe1 | Spe1 |
| 5'-CC<u>CTCGAG</u>ATCATGCCGTTTGGAATAGACAACACCGA | CPR1 | Xho1 | Xho1 |
| 5'-CC<u>AAGCTT</u>ATCGGGCTGATTACCAGACATCTTCTTG | CPR1 | HindIII | HindIII |
| 5'-CC<u>GGATCC</u>CCATGTCCTCTTCTTCTTCGTCAAC | AR2 | Bamh1 | Bamh1 |
| 5'-CC<u>CTCGAG</u>GTGAGTGTGTGGCTTCAATAGTTT CG | AR2 | Xho1 | Xho1 |

*SEQ ID Nos 19-32

Example 3

Construction of a Yeast Vector for Expression of PAL and C4H

The gene encoding C4H, isolated as described in example 1, was amplified by PCR using the forward- and reverse primers, with 5' overhangs containing Xho1 and Kpn1 restriction sites. The amplified C4H PCR-product was digested with Xho1/Kpn1 and ligated into similarly digested pESC-URA-PAL vector. The resulting plasmid, pESC-URA-PAL-C4H, contained the genes encoding PAL and C4H under the control of the divergent GAL1/GAL10 promoter. The sequence of the gene encoding C4H was verified by sequencing of two different clones.

Example 4

Construction of a Yeast Vector for Expression of 4CL

The gene encoding 4CL was isolated as described in example 1. The amplified 4CL PCR-product was digested with Xba1/BamH1 and ligated into Spe1/BglII digested pESC-TRP vector (Stratagene), resulting in vector pESC-TRP-4CL. Two different clones of pESC-TRP-4CL were sequenced to verify the sequence of the cloned gene.

Example 5

Construction of a Yeast Vector for Expression of 4CL and VST

The gene encoding VST was isolated as described in example 1. The amplified synthetic VST gene was digested with BamH1/Xho1 and ligated into BamH1/Xho1 digested pESC-TRP-4CL (example 4). The resulting plasmid, pESC-TRP-4CL-VST, contained the genes encoding 4CL and VST under the control of the divergent GAL1/GAL10 promoter. The sequence of the gene encoding VST was verified by sequencing of two different clones of pESC-TRP-4CL-VST.

Example 6

Construction of a Yeast Vector for Expression of TAL

The gene encoding TAL was isolated as described in example 1. The amplified synthetic TAL gene was digested with EcoR1/Spe1 and ligated into EcoR1/Spe1-digested pESC-URA vector. The resulting plasmid, pESC-URA-TAL, contained the gene encoding for TAL under the control of the divergent GAL1/GAL10 promoter. The sequence was verified by sequencing of two different clones of pESC-URA-TAL.

Example 7

Construction of a Yeast Vector for Overexpression of S. cerevisiae Endogenous CPR The gene encoding CPR from S. cerevisiae (CPR1) was isolated as described in example 1. The amplified CPR1 gene was digested with Xho1/HindIII and ligated into Xho1/HindIII-digested pESC-LEU vector (Stratagene), resulting in vector pESC-LEU-CPR1. The sequence was verified by sequencing of two different clones of pESC-LEU-CPR1.

Example 8

Construction of a Yeast Vector for Overexpression of A. thaliana CPR (AR2)

The gene encoding CPR from A. thaliana (AR2) was isolated as described in example 1. The amplified AR2 gene was digested with BamH1/Xho1 and ligated into BamH1/Xho1 digested pESC-LEU vector (Stratagene), resulting in vector pESC-LEU-AR2.

The sequence was verified by sequencing of two different clones of pESC-LEU-AR2.

Example 9

Expression of the Pathway to Resveratrol in the Yeast S. cerevisiae Using PAL, C4H, 4CL and VST Yeast strains containing the appropriate genetic markers were transformed with the vectors described in examples 2, 3, 4, 5, 6, 7 and 8, separately or in combination. The transformation of the yeast cell was conducted in accordance with methods known in the art, for instance, by using competent cells or by electroporation (see, e.g., Sambrook et al., 1989). Transformants were selected on medium lacking uracil and/or tryptophan and streak purified on the same medium.

S. cerevisiae strain CEN.PK 113-5D (MATa ura3) was transformed separately with the vector pESC-URA-PAL (example 2), yielding the strain FSSC-PAL, and with pESC-URA-PAL-C4H (example 3), resulting in the strain FSSC-PALC4H. S. cerevisiae strain FS01267 (MATa trp1 ura3) was co-transformed with pESC-URA-PAL-C4H and pESC-TRP-4CL (example 4), and the transformed strain was named FSSC-PALC4H4CL. The same strain was also co-transformed with pESC-URA-PAL-C4H and pESC-TRP-4CL-VST (example 5), resulting in the strain FSSC-PALC4H4CLVST.

Example 10

Expression of the Pathway to Resveratrol in S. cerevisiae Using TAL, 4CL and VST S. cerevisiae strain CEN.PK 113-5D (MATa ura3) was transformed separately with the vector pESC-URA-TAL (example 6), yielding the strain FSSC-TAL. S. cerevisiae strain FS01267 (MATa trp1 ura3) was co-transformed with pESC-URA-TAL (example 6) and pESC-TRP-4CL (example 4), and the transformed strain was named FSSC-TAL4CL. The same strain was also co-transformed with pESC-URA-TAL and pESC-TRP-4CL-VST (example 5), resulting in the strain FSSC-TAL4CLVST. Transformants were selected on medium lacking uracil and or tryptophan and streak purified on the same medium.

Example 11

Expression of the Pathway to Resveratrol in S. Cerevisiae with Overexpressed Endogenous CPR S. cerevisiae strain FS01277 (MATa ura3 leu2 trp1) was co-transformed with vectors pESC-URA-PAL-C4H (example 3), pESC-TRP-4CL (example 4), and pESC-LEU- CPR1 (example 7). The transformed strain was named FSSC-PALC4H4CLVSTCPR. Transformants were selected on medium lacking uracil and/or tryptophan and streak purified on the same medium.

Example 12

Expression of the Pathway to Resveratrol in *S. cerevisiae* with Overexpressed *A. thaliana* CPR (AR2)

*S. cerevisiae* strain FS01277 (MATa ura3 leu2 trp1) was co-transformed with vectors pESC-URA-PAL-C4H (example 3), pESC-TRP-4CL (example 4), and pESC-LEU-AR2 (example 8). The transformed strain was named FSSC-PALC4H4CLVSTAR2. Transformants were selected on medium lacking uracil and or tryptophan and streak purified on the same medium.

Example 13

Fermentation with Recombinant Yeast Strains in Shake Flasks

The recombinant yeast strains were inoculated from agar plates with a sterile inoculation loop and grown in 200 ml defined mineral medium (Verduyn et al, 1992) that contained vitamins, trace elements, 5 g/l glucose and 40 g/l or 100 g/l galactose. The 500 ml stoppered shake flasks were incubated for three days at 30° C. and 160 rpm.

Example 14

Extraction of Resveratrol

Cells were harvested by centrifugation 5000 g for 5 minutes. An aliquot of 50 ml of supernatant was extracted once with 20 ml ethyl acetate. The ethyl acetate was freeze dried and the dry product redissolved in 0.7 ml methanol and filtered into HPLC vials.

The cell pellet from 200 ml medium was dissolved in 1 to 2 ml water and divided into 3 fastprep tubes and broken with glass beads. The crude extracts from the three tubes were pooled into 10 ml 100% methanol in a 50 ml sartorius tube and extracted on a rotary chamber for 48 hours in a dark cold room at 4° C. After 48 hours the cell debris was removed via centrifugation for 5 min. at 5000 g and the methanol was removed by freeze-drying overnight. The dried residue was redissolved in 1 ml phosphate-citrate buffer pH 5.4 and 10 units beta-glucosidase from almonds was added (Sigma) to release resveratrol from putatively glucoside-bound forms. The mixture was incubated for three hours at 37° C. and then extracted twice with 1 ml ethyl acetate. The combined ethyl acetate was freeze dried and the dry residue was redissolved in 0.7 ml methanol and filtered into HPLC vials.

Example 15

Analysis of Resveratrol

Thin Layer Chromatography
A method based upon thin layer chromatography that enabled the quick separation of cinnamic, coumaric and resveratrol on the same TLC-plate was developed for quick screening analysis. An aliquot of 1 ml culture containing both cells and supernatant were extracted with 500 microliter ethyl acetate and centrifuged for 30 s. at 13000 rpm with a microcentrifuge. The ethyl acetate was dried and redissolved in methanol. The extracts were analyzed on Silica G plates (0.2 mm Alugram SIL G/UV$_{254}$, Macherey-Nagel) containing a fluorescent indicator. The mobile phase was a mixture of chloroform, ethyl acetate and formic acid (25:10:1).

HPLC
For quantitative analysis of cinnamic acid, coumaric acid, and resveratrol, samples were subjected to separation by high-performance liquid chromatography (HPLC) Agilent Series 1100 system (Hewlett Packard) prior to uv-diode-array detection at λ=306 nm. A Phenomenex (Torrance, Calif., USA) Luna 3 micrometer C18 (100×2.00 mm) column was used at 40° C. As mobile phase a gradient of acetonitrile and milliq water (both containing 50 ppm trifluoroacetic acid) was used at a flow of 0.4 ml/min. The gradient profile was linear from 15% acetonitrile to 100% acetonitrile over 20 min. The elution times were approximately 3.4 min. for coumaric acid, 5.5 min. for free trans-resveratrol and 6.8 min. for cinnamic acid.

Pure resveratrol standard was purchased from Cayman chemical company, whereas pure coumaric acid and cinnamic acid standards were purchased from and Sigma.

Figure 4:
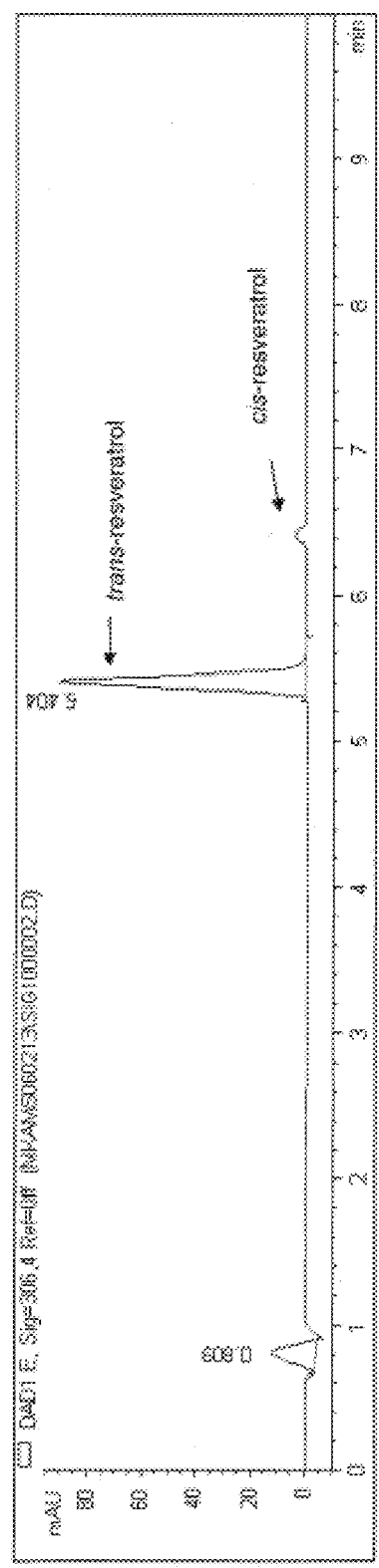
FIG. 4 shows the HPLC-chromatograms of extracts of S. cerevisiae strains FSSC-PALC4H4CLVST, FSSC-TAL4CLVST, grown on 100 g/l galactose. A chromatogram of 60 nanogram of pure resveratrol is included.
Figure 4:
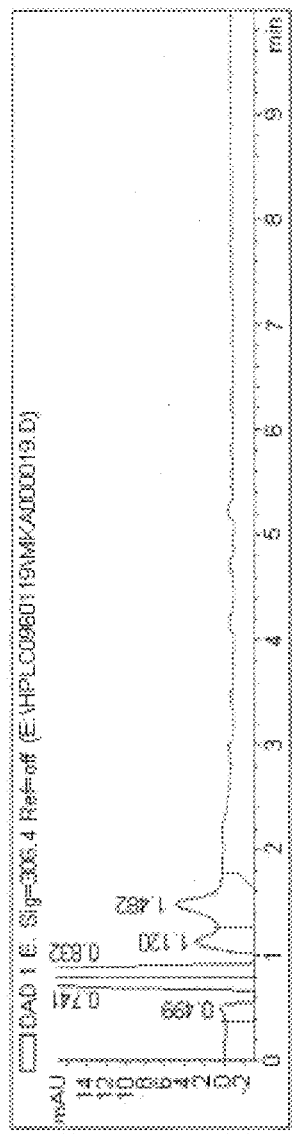
Figure 5:
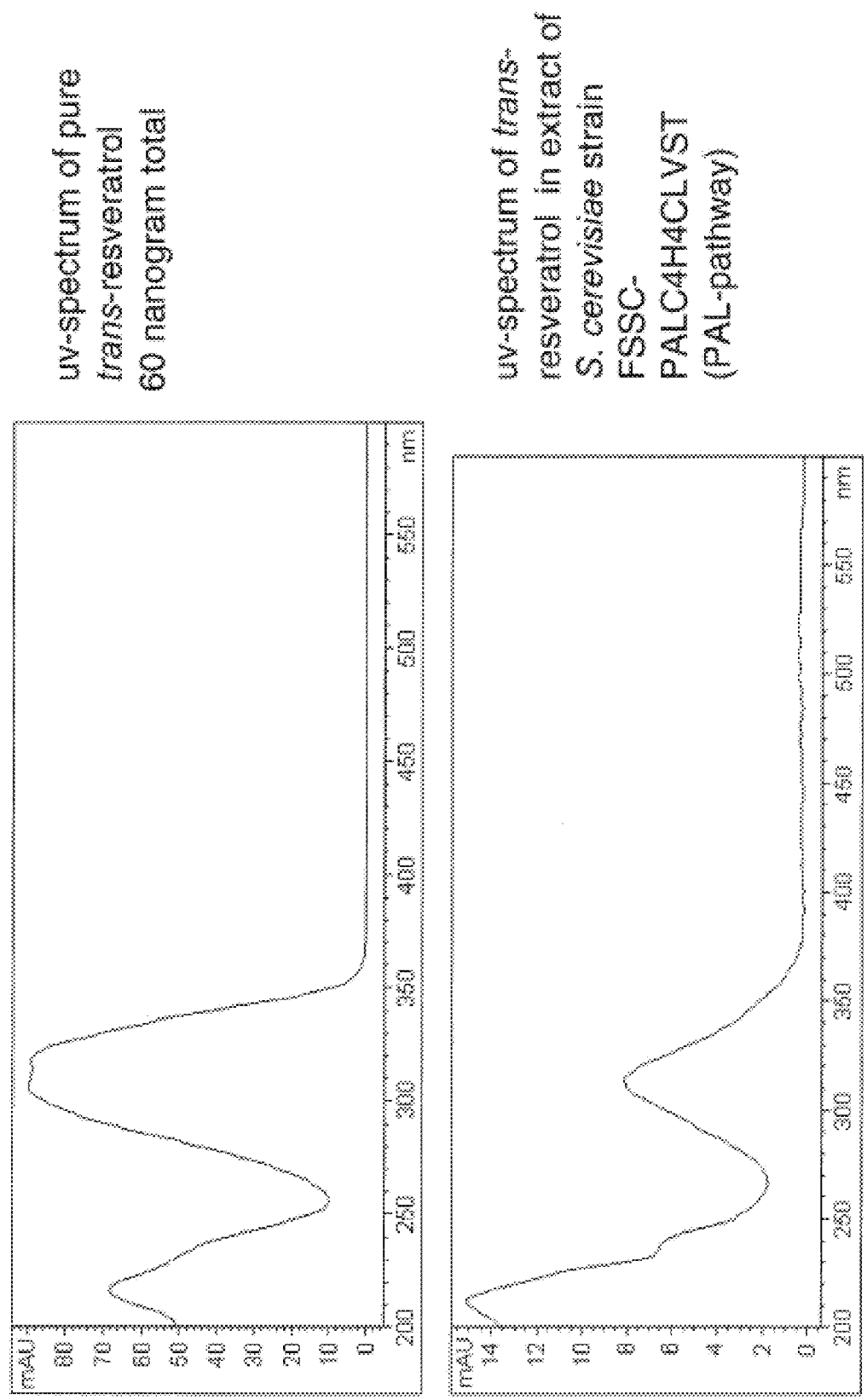
FIG. 5 shows the UV absorption spectrum for pure trans-resveratrol and trans-resveratrol produced by S. cerevisiae strain FSSC-PALC4H4CLVST, grown on 100 g/l galactose.

Results
Strains FSSC-PALC4H4CLVST and FSSC-TAL4CLVST, were cultivated on 100 g/l galactose as described in example 13, and analyzed for their content of intracellular resveratrol according to example 14 and 15. Additionally, a control strain FSSC-control was included that contained the empty vectors pESC-URA and pESC-TRP only. The HPLC-analysis showed that strains FSSC-PALC4H4CLVST and FSSC-TAL4CLVST contained a component with a retention time of 5.5 min. that was identical to trans-resveratrol (FIG. 4). Said result was confirmed by the UV absorption spectra that were similar to the absorption spectrum of pure trans-resveratrol (FIG. 5) as well, with a $\lambda_{max}$ of approximately 306 nm.

The results, therefore, demonstrated the presence of an active phenyl-propanoid pathway in *S. cerevisiae* that led to in vivo production of trans-resveratrol. The production of resveratrol can most likely be improved by cultivating the strains under well-defined growth conditions in batch- and continuous cultures, and/or optimizing the expression/activities of the individual enzymes.

Example 16

Construction of a Bacterial Vector for Expression of TAL in *Escherichia coli*

The gene encoding TAL, isolated as described in Example 1, was reamplified by PCR from the plasmid pESC-URA-TAL (example 6) using the forward primer 5'-CCG CTC-GAG CGG ATG ACC CTG CAA TCT CAA ACA GCT AAA G-3' SEQ ID NO 33 and the reverse primer 5'-GC GGATCC TTA AGC AGG TGG ATC GGC AGC T-3' SEQ ID NO 34 with 5' overhangs containing the restriction sites XhoI and BamHI, respectively. The introduction of restriction sites at the 5' and 3' ends of the gene allowed ligation of the restricted PCR product into a pET16b vector (Novagen), digested with XhoI and BamHI to yield pET16b-TAL. The pET16b vector contained both the ampicillin resistance gene, and the T7 promoter. Hence, above procedure resulted in a vector with an antibiotic selection marker that contained the gene encoding for TAL under the control of the T7 promoter. The sequence of the gene encoding TAL was verified by sequencing of one clone of pET16b-TAL.

Example 17

Construction of a Bacterial Vector for Expression of 4CL and VST in *Escherichia coli*

The gene encoding VST, isolated as described in example 1, was cut out with the restriction enzymes BamHI and XhoI from the digested plasmid pESC-TRP-4CL-VST (example 5), which contains the genes encoding 4CL and VST. The VST gene was ligated into a pET26b vector (Novagen), containing the kanamycin resistance gene, digested with BamHI and SalI to yield pET26b-VST. The restriction enzymes XhoI and SalI have compatible ends, which enabled proper ligation. The pET26b vector contained both the kanamycin resistance gene, and the T7 promoter. Hence, above procedure resulted in a vector with an antibiotic selection marker that contained the gene encoding for VST under the control of the T7 promoter. The gene encoding for 4CL, isolated as described in example 1, was reamplified by PCR from the plasmid pESC-URA-4CL-VST (example 5) using the forward primer 5'-TG CCATGG CA ATGGCGC-CAC AAGAACAAGC AGTTT-3' SEQ ID NO 35 and the reverse primer 5'-GC GGATCC CCT TCA CAA TCC ATT TGC TAG TTT TGCC-3' SEQ ID NO 36 with 5' overhangs containing the restriction sites NcoI and BamHI, respectively. The introduction of restriction sites at the 5' and 3' ends of the gene allowed ligation of the restricted PCR product into a pET16b vector (Novagen) digested with NcoI and BamHI. The resulting plasmid, pET16b-4CL, contained the gene encoding for 4CL under the control of the T7 promoter. Both the T7 promoter and the gene encoding for 4CL were reamplified as one fragment by PCR from the plasmid pET16b-4CL using the forward primer 5'-TT GCG-GCCGC AAA TCT CGA TCC CGC GAA ATT AAT ACG-3' SEQ ID NO 37 and the reverse primer 5'-CG CTCGAG CCT TCA CAA TCC ATT TGC TAG TTT TGCC-3' SEQ ID NO 38 with 5' overhangs, containing the restriction sites NotI and XhoI, respectively. The introduction of restriction sites at the 5' and 3' ends of the DNA fragment allowed ligation of the restricted PCR product into the plasmid pET26b-VST that was digested with NotI and XhoI before ligation. The resulting plasmid, pET26b-VST-4CL, contained the two genes 4CL and VST that each were under control of an individual T7 promoter.

Example 18

Expression of the Pathway to Resveratrol in *Escherichia Coli*, Using TAL, 4CL and VST The transformation of the bacterial cell was conducted in accordance with methods known in the art, for instance, by using competent cells or by electroporation (see, e.g., Sambrook et al., 1989). The *E. coli* strain BL21 (DE3) (Novagen) was co-transformed with the two vectors pET16b-TAL (example 16) and pET26b-VST-4CL (Example 17), resulting in strain FSEC-TAL4CLVST. In addition, *E. coli* strain BL21 (DE3) was co-transformed with the two empty vectors pET16b (Novagen) and pET26b (Novagen), resulting in strain FSEC-control, which was used as a control strain. Transformants were selected on Luria-Bertani (LB) medium with 100 µg/ml ampicillin and 60 µg/ml kanamycin.

Example 19

Fermentation with Recombinant *Escherichia coli* Strains in Shake Flasks

Pre-cultures of *Escherichia coli* BL21 (DE3) were grown in glass tubes at 160 rpm and 37° C. in 7 ml of LB medium containing 100 µg/ml ampicillin and 60 µg/ml kanamycin. Exponentially growing precultures were used for inoculation of 500 ml baffled shake flasks that contained 200 ml LB medium supplemented with 50 g/l glucose, 5 g/l $K_2HPO_4$, 80 µg/ml ampicilin and 50 µg/ml kanamycin, which were incubated at 160 rpm and 37° C. After 5 hours, isopropyl β-thiogalactopyranoside (IPTG) was added at a final concentration of 1 mM, as an inducer of the T7 promoter that was in front of each of the three genes TAL, 4CL and VST. After an incubation period of 48 hours at 37° C., the cells were harvested and subjected to extraction procedures and analysed for the presence of produced resveratrol.

Example 20

Extraction and Analysis of Resveratrol in *Escherichia coli*

Extraction and analysis was performed using the methods as described in example 14 and 15.

Results

Figure 6:
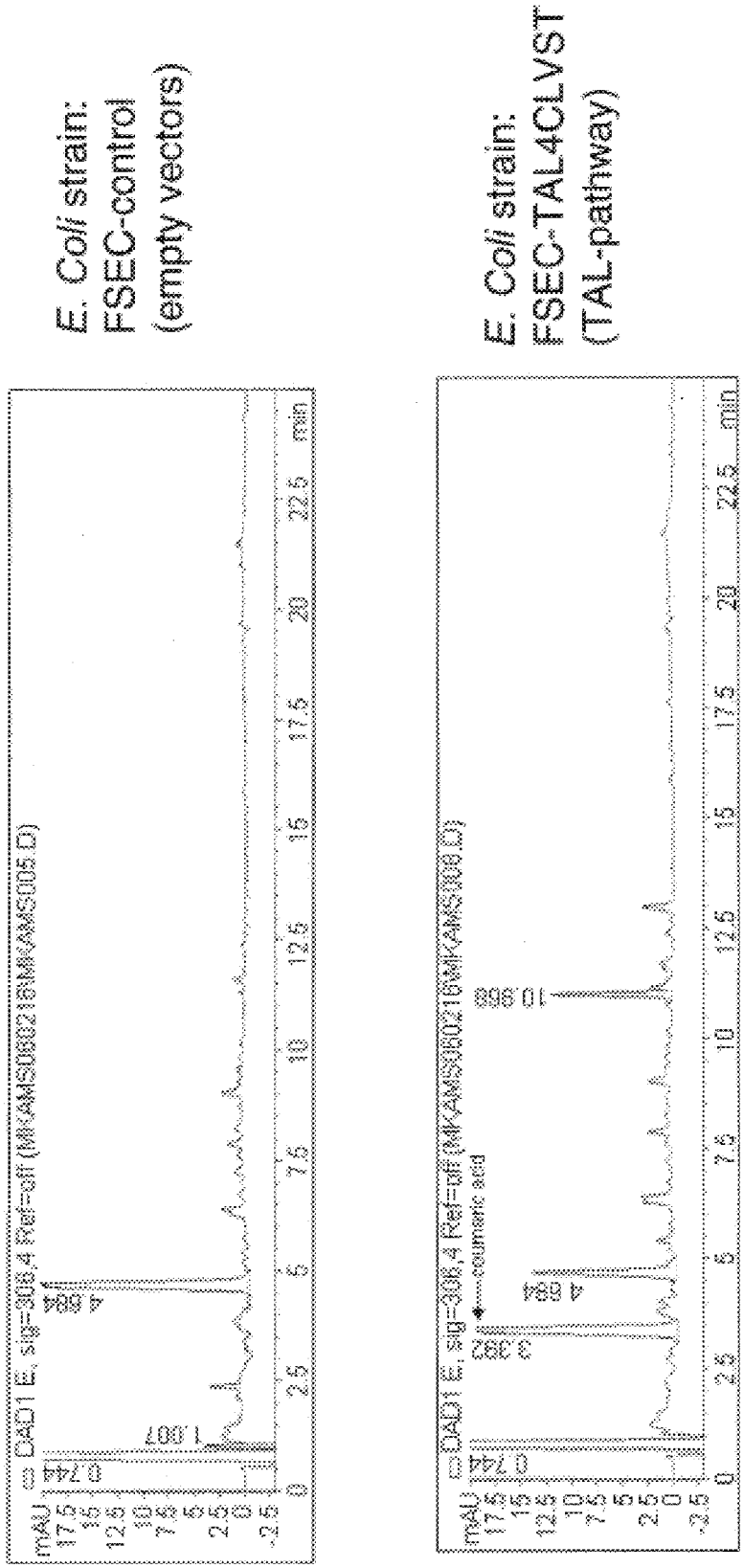
FIG. 6 shows the HPLC-chromatograms of extracts from E. coli strains FSEC-TAL4CLVST and FSEC-control, grown on 50 g/l glucose.
Figure 7:
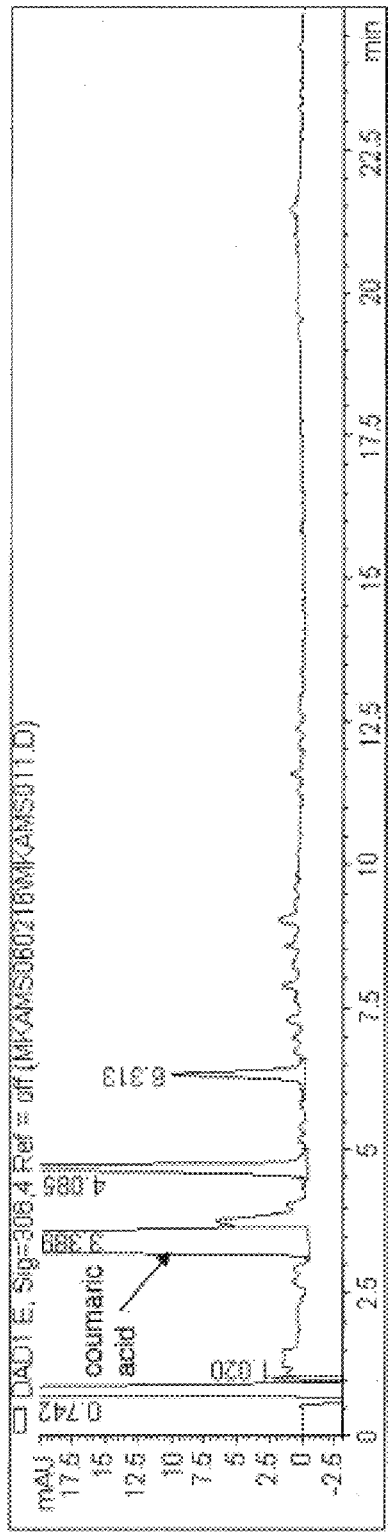
FIG. 7 shows the HPLC-chromatograms of extracts from E. coli strains FSEC-TAL4CLVST and FSEC-control, grown on 50 g/l glucose with addition of 20 mg/l coumaric acid. The UV absorption spectrum for trans-resveratrol produced in strain FSEC-TAL4CLVST is included.

Strain FSEC-TAL4CLVST and FSEC-control, were cultivated on 50 g/l glucose as described in example 19, and analyzed for their content of intracellular resveratrol according to example 14 and 15. The HPLC-analysis showed that strain FSEC-TAL4CLVST did contain considerable amounts of a component with a retention time of 3.4 min., which is identical to coumaric acid (FIG. 6). However, the extract did not contain a component that eluted at the same time as trans-resveratrol. Said result, therefore, indicated that the tyrosine ammonia lyase (TAL) was active indeed, but did not lead to production of detectable amounts of resveratrol. The lack of resveratrol formation, however, could be the result of; i) a non-functional coumarate-CoA ligase (4CL); ii) a non-functional resveratrol synthase (VST); iii) too low levels of coumaric acid, caused by either non-optimal cultivation conditions, or non-optimal expression/activity of TAL, or branching of coumaric acid into other products. To evaluate said hypotheses, the strains were grown on similar media as described in example 19 but now in the presence of 20 mg/l of coumaric acid. The subsequent HPLC-analysis of extracts of FSEC-TAL4CLVST indeed showed a cluster of peaks around the same retention time as trans-resveratrol, which was not observed in extracts of FS-control (FIG. 6). Indeed, the UV absorption spectrum of the peak with a retention time of 5.5 min. was similar to the spectrum of pure trans-resveratrol (FIG. 7), whereas no such spectrum could be obtained for peaks in the control strain. The results, therefore, strongly suggest the presence of an active phenylpropanoid pathway in *Escherichia coli*, which can lead to production of resveratrol. Most likely the production of resveratrol without addition of coumaric acid can be achieved by cultivating the strains under well-defined growth conditions in batch- and continuous cultures, and/or optimizing the expression/activities of the individual enzymes.

Example 21

Construction of a Bacterial Vector for Expression of PAL and C4H in *Lactococcus lactis*

The plasmid pSH71 and derivatives thereof, which is used in the following examples, is a bifunctional shuttle vector with multiple origins of replication from *Escherichia coli* and *Lactococcus lactis*. With that, the host range specificity traverses *Escherichia coli* and other species of lactic acid bacteria. Though transformations in *Lactococcus lactis* usually proceed without problems, putative difficult transformations in other species of lactic acid bacteria can, therefore, be overcome by using *Escherichia coli* as an intermediate host for the construction of recombinant plasmids. The plasmid contains one or more marker genes to allow the microorganism that harbour them to be selected from those which do not. The selection system that is used for *Lactococcus lactis* is based upon dominant markers, e.g. resistance against erythromycin and chloramphenicol, but systems based upon genes involved in carbohydrate metabolism, peptidases and food grade markers, have also been described. In addition, the plasmid contains promoter- and terminator sequences that allow the expression of the recombinant genes. Suitable promoters are taken from genes of *Lactococcus lactis* e.g. lacA. Furthermore, the plasmid contains suitable unique restriction sites to facilitate the cloning of DNA fragments and subsequent identification of recombinants.

In the examples below the plasmid contains either the erythromycine resistance gene, designated as pSH71-ERY$^r$, or the chloramphenicol resistance gene, designated as pSH71-CM$^r$ The gene encoding PAL, isolated as described in example 1, is reamplified by PCR from the plasmid pESC-URA-PAL-C4H (example 3), using forward- and reverse primers, with 5' overhangs containing suitable restriction sites. The introduction of said restriction sites at the 5' and 3' ends of the gene allows ligation of the restricted PCR product into a digested pSH71-ERY$^r$ vector that contains the lacA promoter from *Lactococcus lactis*. The resulting plasmid, pSH71-ERY$^r$-PAL, contains the gene encoding PAL under the control of the lacA promoter from *Lactococcus lactis*. The gene encoding C4H, isolated as described in example 1, is reamplified by PCR from the plasmid pESC-URA-PAL-C4H (example 3) using forward- and reverse primers, with 5' overhangs containing suitable restriction sites. The introduction of said restriction sites at the 5' and 3' ends of the gene allows ligation of the restricted PCR product into a digested pSH71-CM$^r$ vector to yield pSH71-CM$^r$-C4H. The lacA promoter and the gene encoding C4H are reamplified as one fragment by PCR from the plasmid pSH71-CM$^r$-C4H using forward- and reverse primers, with 5' overhangs containing suitable restriction sites. The introduction of said restriction sites at the 5' and 3' ends of the DNA fragment allows ligation of the restricted PCR product into the digested plasmid pSH71-ERY$^r$-PAL. The resulting plasmid, pSH71-ERY$^r$-PAL-C4H, contains the genes encoding PAL and C4H that are each under the control of an individual lacA promoter. The sequence of the genes encoding PAL and C4H is verified by sequencing of two different clones of pSH71-ERY$^r$-PAL-C4H.

Example 22

Construction of a Bacterial Vector for Expression of TAL in *Lactococcus lactis*

The gene encoding for TAL, isolated as described in example 1, is reamplified by PCR from the plasmid pESC-URA-TAL (example 6) using forward- and reverse primers, with 5' overhangs containing suitable restriction sites. The introduction of said restriction sites at the 5' and 3' ends of the gene allows ligation of the restricted PCR product into a digested pSH71-ERY$^r$ vector. The resulting plasmid, pSH71-ERY$^r$-TAL, contains the gene encoding for TAL under the control of the lacA promoter from *Lactococcus lactis*. The sequence of the gene encoding for TAL is verified by sequencing of two different clones of pSH71-ERY$^r$-TAL.

Example 23

Construction of a Bacterial Vector for Expression of 4CL and VST in *Lactococcus lactis*

The gene encoding 4CL, isolated as described in example 1, is reamplified by PCR from the plasmid pESC-TRP-4CL-VST (example 5), using forward- and reverse primers, with 5' overhangs containing suitable restriction sites. The introduction of said restriction sites at the 5' and 3' ends of the gene allows ligation of the restricted PCR product into a digested pSH71-CM$^r$ vector. The resulting plasmid, pSH71-CM$^r$-4CL, contains the gene encoding for 4CL under the control of the lacA promoter from *Lactobacillus lactis*. The gene encoding VST, isolated as described in example 1, is reamplified by PCR from the plasmid pESC-TRP-4CL-VST (example 5) using forward- and reverse primers, with 5' overhangs containing suitable restriction sites. The introduction of said restriction sites at the 5' and 3' ends of the gene allows ligation of the restricted PCR product into a digested pSH71-ERY$^r$ vector. The resulting plasmid, pSH71-ERY$^r$-VST, contains the gene encoding VST under the control of the lacA promoter from *Lactococcus lactis*. The lacA promoter and the gene encoding VST are reamplified as one fragment by PCR from the plasmid pSH71-ERY$^r$-VST using forward- and reverse primers, with 5' overhangs containing suitable restriction sites. The introduction of said restriction sites at the 5' and 3' ends of the DNA fragment allows ligation of the restricted PCR product into the digested plasmid pSH71-CM$^r$-4CL. The resulting plasmid, pSH71-CM$^r$-4CL-VST, contains the genes encoding 4CL and VST that are each under the control of their individual lacA promoter.

The sequence of the genes encoding 4CL and VST is verified by sequencing of two different clones of pSH71-CM$^r$-4CL-VST.

Example 24

Expression of the Pathway to Resveratrol in *Lactococcus lactis*

*Lactococcus lactis* strains are transformed with the vectors described in examples 21, 22 and 23, separately or in combination. The transformation of the bacterial cell is conducted in accordance with methods known in the art, for instance, by using competent cells or by electroporation (see, e.g., Sambrook et al., 1989). Transformants are selected on medium containing the antibiotics erythromycin and chloramphenicol and streak purified on the same medium.

*Lactococcus lactis* strain MG1363 is transformed separately with the vector pSH71-ERY$^r$-TAL (example 22), yielding the strain FSLL-TAL; with pSH71-ERY$^r$-PAL-C4H (example 21), yielding the strain FSLL-PALC4H and with pSH71-CM$^r$-4CL-VST (example 23), yielding strain FSLL-4CLVST. In addition, *Lactococcus lactis* strain MG1363 is co-transformed with pSH71-ERY$^r$-TAL (example 22) and pSH71-CM$^r$-4CL-VST (example 23), and the transformed strain is named FSLL-TAL4CLVST. The same strain is also co-transformed with pSH71-ERY$^r$-PAL-C4H (example 21), and pSH71-CM'-4CL-VST (example 23), resulting in the strain FSLL-PALC4H4CLVST.

Example 25

Fermentation with Recombinant *Lactococcus lactis* Strains in Fermentors

The recombinant yeast strains can be grown in fermenters operated as batch, fed-batch or chemostat cultures.
Batch and Fed-Batch Cultivations The microorganism is grown in a baffled bioreactor with a working volume of 1.5 liters under anaerobic, aerobic or microaerobic conditions. All cultures are incubated at 30° C., at 350 rpm. A constant pH of 6.6 is maintained by automatic addition of 10 M KOH. Cells are grown on lactose in defined MS10 medium supplemented with the following components to allow growth under aerobic conditions: $MnSO_4$ ($1.25 \times 10^{-5}$ g/l), thiamine (1 mg/l), and DL-6,8-thioctic acid (2.5 mg/l). The lactose concentration is, for example 50 g/l. The bioreactors are inoculated with cells from precultures grown at 30° C. in shake flasks on the medium described above buffered with threefold-higher concentrations of $K_2HPO_4$ and $KH_2PO_4$. Anaerobic conditions are ensured by flushing the medium with $N_2$ (99.998% pure) prior to inoculation and by maintaining a constant flow of 50 ml/min of $N_2$ through the headspace of the bioreactor during cultivation. The bioreactors used for microaerobic and aerobic cultivation are equipped with polarographic oxygen sensors that are calibrated with air (DOT, 100%) and $N_2$ (DOT, 0%). Aerobic conditions are obtained by sparging the bioreactor with air at a rate of 1 vvm to ensure that the DOT is more than 80%. During microaerobic experiments the DOT is kept constant 5% by sparging the reactor with gas composed of a mixture of $N_2$ and atmospheric air, at a rate of 0.25 vvm.
Chemostat Cultures In chemostat cultures the cells can be grown in, for example, 1-L working-volume Applikon laboratory fermentors at 30° C. and 350 rpm. The dilution rate (D) can be set at different values, e.g. at 0.050 $h^{-1}$, 0.10 $h^{-1}$, 0.15 $h^{-1}$, or 0.20 $h^{-1}$. The pH is kept constant, e.g at 6.6, by automatic addition of 5 M KOH, using the growth medium described above, supplemented with antifoam (50 µl/l). The concentration of lactose can be set at different values, e.g. is 3.0 g/l 6.0 g/l, 12.0 g/l, 15.0 g/l or 18.0 g/l. The bioreactor is inoculated to an initial biomass concentration of 1 mg/l and the feed pump is turned on at the end of the exponential growth phase.

An anaerobic steady state is obtained by introducing 50 ml/min of $N_2$ (99.998% pure) into the headspace of the bioreactor. Different anoxic steady states can obtained by sparging the reactor with 250 ml/min of gas composed of $N_2$ (99.998% pure) and atmospheric air at various ratios. The oxygen electrode is calibrated by sparging the bioreactor with air (100% DOT) and with $N_2$ (0% DOT).

For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.

Cultivations are considered to be in steady state after at least 5 residence times, and if the concentrations of biomass and fermentation end products remain unchanged (less than 5% relative deviation) over the last two residence times.

Example 26

Extraction and Analysis of Resveratrol in *Lactococcus lactis*

Extraction and analysis is performed using the methods as described in examples 14 and 15.

Example 27

Construction of a Fungal Vector for Expression of PAL and C4H in Species Belonging to the Genus *Aspergillus*

The plasmid that is used in the following examples, is derived from pARp1 that contains the AMA1 initiating replication sequence from *Aspergillus nidulans*, which also sustains autonomous plasmid replication in *A. niger* and *A. oryzae* (Gems et al., 1991). Moreover, the plasmid is a shuttle vector, containing the replication sequence of *Escherichia coli*, and the inherent difficult transformations in *Aspergillus niger* and *Aspergillus oryzae* can therefore overcome by using *Escherichia coli* as an intermediate host for the construction of recombinant plasmids. The plasmid contains one or more marker genes to allow the microorganism that harbour them to be selected from those which do not. The selection system can be either based upon dominant markers e.g. resistance against hygromycin B, phleomycin and bleomycin, or heterologous markers e.g amino acids and the pyrG gene. In addition the plasmid contains promoter- and terminator sequences that allow the expression of the recombinant genes. Suitable promoters are taken from genes of *Aspergillus nidulans* e.g. alcA, glaA, amy, niaD, and gpdA. Furthermore, the plasmid contains suitable unique restriction sites to facilitate the cloning of DNA fragments and subsequent identification of recombinants.

The plasmid used in the following examples contains the strong constitutive gpdA-promoter and auxotropic markers, all originating from *Aspergillus nidulans*; the plasmid containing the gene methG that is involved in methionine biosynthesis, is designated as pAMA1-MET; the plasmid containing the gene hisA that is involved in histidine biosynthesis, is designated as pAMA1-HIS.

The gene encoding PAL, isolated as described in example 1, is reamplified by PCR from the plasmid pESC-URA-PAL-C4H (example 3), using forward- and reverse primers, with 5' overhangs containing suitable restriction sites. The introduction of said restriction sites at the 5' and 3' ends of the gene allows ligation of the restricted PCR product into a digested pAMA1-MET vector that contains the gpdA promoter from *Aspergillus nidulans*. The resulting plasmid, pAMA1-MET-PAL contains the gene encoding PAL under the control of the gpdA promoter from *Aspergillus nidulans*.

The gene encoding C4H, isolated as described in example 1, is reamplified by PCR from the plasmid pESC-URA-PAL-C4H (example 3) using forward- and reverse primers, with 5' overhangs containing suitable restriction sites. The introduction of said restriction sites at the 5' and 3' ends of the gene allows ligation of the restricted PCR product into a digested pAMA1-HIS vector to yield pAMA1-HIS-C4H. The gpdA promoter and the gene encoding C4H are reamplified as one fragment by PCR from the plasmid pAMA1-HIS-C4H using forward- and reverse primers, with 5' overhangs containing suitable restriction sites. The introduction of said restriction sites at the 5' and 3' ends of the DNA fragment allows ligation of the restricted PCR product into the digested plasmid pAMA1-MET-PAL. The resulting plasmid, pAMA1-MET-PAL-C4H, contains the genes encoding PAL and C4H that are each under the control of an individual pgdA promoter from *Aspergillus nidulans*. The sequence of the genes encoding PAL and C4H is verified by sequencing of two different clones of pAMA1-MET-PAL-C4H.

Example 28

Construction of a Fungal Vector for Expression of TAL in Species Belonging to the Genus *Aspergillus*

The gene encoding for TAL, isolated as described in example 1, is reamplified by PCR from the plasmid pESC-URA-TAL (example 6) using forward- and reverse primers, with 5' overhangs containing suitable restriction sites. The introduction of said restriction sites at the 5' and 3' ends of the gene allows ligation of the restricted PCR product into a digested pAMA1-MET vector. The resulting plasmid, pAMA1-MET-TAL, contains the gene encoding for TAL under the control of the gpdA promoter from *Aspergillus nidulans*. The sequence of the gene encoding for TAL is verified by sequencing of two different clones of pAMA1-MET-TAL.

Example 29

Construction of a Fungal Vector for Expression of 4CL and VST in Species Belonging to the Genus *Aspergillus*

The gene encoding 4CL, isolated as described in example 1, is reamplified by PCR from the plasmid pESC-TRP-4CL-VST (example 5), using forward- and reverse primers, with 5' overhangs containing suitable restriction sites. The introduction of said restriction sites at the 5' and 3' ends of the gene allows ligation of the restricted PCR product into a digested pAMA1-HIS vector that contains the gpdA promoter from *Aspergillus nidulans*. The resulting plasmid, pAMA1-HIS-4CL contains the gene encoding 4CL under the control of the gpdA promoter from *Aspergillus nidulans*. The gene encoding VST, isolated as described in example 1, is reamplified by PCR from the plasmid pESC-TRP-4CL-VST (example 5) using forward- and reverse primers, with 5' overhangs containing suitable restriction sites. The introduction of said restriction sites at the 5' and 3' ends of the gene allows ligation of the restricted PCR product into a digested pAMA1-MET vector to yield pAMA1-MET-VST. The gpdA promoter and the gene encoding VST are reamplified as one fragment by PCR from the plasmid pAMA1-MET-VST using forward- and reverse primers, with 5' overhangs containing suitable restriction sites. The introduction of said restriction sites at the 5' and 3' ends of the DNA fragment allows ligation of the restricted PCR product into the digested plasmid pAMA1-HIS-4CL. The resulting plasmid, pAMA1-HIS-4CL-VST, contains the genes encoding 4CL and VST that are each under the control of an individual pgdA promoter from *Aspergillus nidulans*. The sequence of the genes encoding 4CL and VST is verified by sequencing of two different clones of pAMA1-HIS-4CL-VST.

Example 30

Expression of the Pathway to Resveratrol in *Aspergillus niger*

*Aspergillus niger* strains are transformed with the vectors described in examples 27, 28 and 29, separately or in combination. The transformation of the fungal cell is conducted in accordance with methods known in the art, for instance, by electroporation or by conjugation (see, e.g., Sambrook et al., 1989). Transformants are selected on minimal medium lacking methionine and/or histidine.

A strain of *Aspergillus niger* that is auxotrophic for histidine and methionine, for instance, strain FGSC A919 (see http://www.fgsc.net), is transformed separately with the vector pAMA1-MET-TAL (example 28), yielding the strain FSAN-TAL; with pAMA1-MET-PAL-C4H (example 27), yielding the strain FSAN-PALC4H and with pAMA1-HIS-4CL-VST (example 29), yielding strain FSAN-4CLVST. In addition, *Aspergillus niger* strain FGSC A919 is co-transformed with pAMA1-MET-TAL (example 28) and pAMA1-HIS-4CL-VST (example 29), and the transformed strain is named FSAN-TAL4CLVST. The same strain is also co-transformed with pAMA1-MET-PAL-C4H (example 27), and pAMA1-HIS-4CL-VST (example 29), resulting in the strain FSAN-PALC4H4CLVST.

Example 31

Expression of the Pathway to Resveratrol in *Aspergillus oryzae*

A strain of *Aspergillus oryzae* that contains a native set of genes encoding for PAL, C4H and 4CL (Seshime et al., 2005) and that is auxotrophic for methionine, is transformed with the vector pAMA1-MET-VST (example 29), yielding the strain FSAO-VST. The transformation of the fungal cell is conducted in accordance with methods known in the art, for instance, by electroporation or by conjugation (see, e.g., Sambrook et al., 1989). Transformants are selected on minimal medium lacking methionine.

Example 32

Fermentation with Recombinant Strains of *Aspergillus niger* and *Aspergillus oryzae* in Fermentors The recombinant yeast strains can be grown in fermenters operated as batch, fed-batch or chemostat cultures.

Batch and Fed-Batch Cultivations

The microorganism is grown in a baffled bioreactor with a working volume of 1.5 liters under aerobic conditions. All cultures are incubated at 30° C., at 500 rpm. A constant pH of 6.0 is maintained by automatic addition of 10 M KOH, and aerobic conditions are obtained by sparging the bioreactor with air at a rate of 1 vvm to ensure that the DOT is more than 80%. Cells are grown on glucose in defined medium consisting of the following components to allow growth in batch cultivations: 7.3 g/l $(NH_4)_2SO_4$, 1.5 g/l $KH_2PO_4$, 1.0 g/l $MgSO_4.7H_2O$, 1.0 g/l NaCl, 0.1 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.7H_2O$. The glucose concentration is, for example, 10- 20-, 30-, 40- or 50 g/l. To allow growth in fed-batch cultivations the medium is composed of: 7.3 g/l $(NH_4)_2SO_4$, 4.0 g/l $KH_2PO_4$, 1.9 g/l $MgSO_4.7H_2O$, 1.3 g/l NaCl, 0.10 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.H_2O$ in the batch phase. The reactor is then fed with, for example, 285 g/kg glucose and 42 g/kg $(NH_4)_2SO_4$.

Free mycelium from a pre-batch is used for inoculating the batch- and fed-batch cultures. A spore concentration of $2.10^9$ spores/l is used for inoculation of the pre-batch culture at pH 2.5. Spores are obtained by propagation of freeze-dried spores onto 29 g rice to which the following components are added: 6 ml 15 g/l sucrose, 2.3 g/l $(NH_4)_2SO_4$, 1.0 g/l $KH_2PO_4$, 0.5 g/l $MgSO_4.7H_2O$, 0.50 g/l NaCl, 14.3 mg/l $ZnSO_4.7H_2O$, 2.5 mg/l $CuSO_4.5H_2O$, 0.50 mg/l $NiCl_2.6H_2O$, and 13.8 mg/l $FeSO_4.7H_2O$. The spores are propagated at 30° C. for 7-14 days to yield a black layer of spores on the rice grains and are harvested by adding 100 ml of 0.1% Tween 20 in sterile water. For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.

Chemostat Cultures

In chemostat cultures the cells can be grown in, for example, 1.5-L working-volume Biostat B laboratory fermentors at 30° C. and 500 rpm. A constant pH of 6.0 is maintained by automatic addition of 10 M KOH, and aerobic conditions are obtained by sparging the bioreactor with air at a rate of 1 vvm to ensure that the DOT is more than 80%. The dilution rate (D) can be set at different values, e.g. at $0.050\ h^{-1}$, $0.10\ h^{-1}$, $0.15\ h^{-1}$, or $0.20\ h^{-1}$. The pH is kept constant, e.g at 6.6, by automatic addition of 10 M KOH, using a minimal growth medium with the following components: 2.5 g/l $(NH_4)_2SO_4$, 0.75 g/l $KH_2PO_4$, 1.0 g/l $MgSO_4.7H_2O$, 1.0 g/l NaCl, 0.1 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.7H_2O$. The concentration of glucose can be set at different values, e.g. is 3.0 g/l 6.0 g/l, 12.0 g/l, 15.0 g/l or 18.0 g/l. The bioreactor is inoculated with free mycelium from a pre-batch culture as described above, and the feed pump is turned on at the end of the exponential growth phase.

For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.

Cultivations are considered to be in steady state after at least 5 residence times, and if the concentrations of biomass glucose and composition of the off-gas remain unchanged (less than 5% relative deviation) over the last two residence times.

Example 33

Extraction and Analysis of Resveratrol in Aspergillus niger and Aspergillus oryzae Extraction and analysis is performed using the methods as described in examples 14 and 15.

Example 34

Over-Expression of Native Yeast Genes by Gene Targeting Method

Over-expression of native yeasts genes with constitutive yeast promoters is carried out by means of a promoter-replacement method based on a linear, PCR-generated gene-targeting substrate and using K. lactis URA3 as a recyclable marker described previously (Erdeniz et al, 1997). This method includes the generation of an intermediate yeast strain, where the Kluyveromyces lactis URA3 marker gene is integrated in combination with two copies of the strong constitutive promoter sequence as a direct repeat on each side of the marker gene. The marker gene is then looped out through recombination mediated by the direct repeat, an event which is selected for by plating the intermediate strain on medium containing 5-fluoroorotic acid (5-FOA), which is toxic to cells expressing the URA3 gene. The result is a yeast strain, in which the native promoter has been replaced with the strong constitutive promoter. Integration of the above described promoter sequence and marker gene is directed to the correct location in the genome by means of PCR-generated target sequences.

The above described gene-targeting substrate can be constructed by means of multiple rounds of fusion-PCR. However, to avoid introduction of PCR-generated mutations, it is beneficial to use a bi-partite or even a quadruple gene-targeting substrate (Erdeniz et al, 1997).

Example 35

Over-Expression of Native Yeast Genes by Bi-Partite Gene Targeting Substrate Method For example to overexpress a gene with the strong ADH1 promoter, this promoter has been introduced into intermediate working vectors on either side of K. lactis URA3, resulting in the vectors pWAD1, pWAD2, (WO/2005/118814). With these vectors as templates, fragments can be amplified that contain (in the 5' to 3' direction) 1) the ADH1 coupled to two thirds of K. lactis URA3 towards the 5' end, using the primers AD-fw and Int3', and 2) two thirds of K. lactis URA3 towards the 3' end coupled to the ADH1, using the primers Int5' and AD-rv. Target sequences corresponding to a 300-500 bp sequence upstream of the gene to be overexpressed and a 300-500 bp starting with ATG of the gene to be overexpressed, are amplified from genomic yeast DNA using suitable primers. The reverse primer used for amplification of the upstream target sequence contains a 5' overhang that allows fusion to fragment 1 described above. The forward primer used for amplification of the target sequence starting with ATG contains a 5' overhang that allows fusion with fragment 2 described above. Following fusion by PCR of the upstream target sequence with fragment 1, and fusion by PCR of fragment 2 with the target sequence starting with ATG, the two linear substrates as shown in FIG. 6 are ready for transformation.

Example 36

Construction of a Strain Overexpressing Native S. cerevisiae NADP-Cytochrome P450 Reductase The native promoter of S. cerevisae NADP-cytochrome P450 reductase CPR1 gene (encoded by YHR042W) was replaced with the constitutive S. cerevisiae alcohol dehydrogenase ADH1 promoter via chromosomal promoter exchange using the "bi-partite" PCR-based allele replacement method as described in example 34 and 35. Primers A and B were used to generate fragment CPR1-UP (Table 1) via PCR at a melting temperature of 56° C. using S. cerevisiae genomic DNA as template. Primers C and D were then used to generate fragment CPR1-S via PCR at a melting temperature of 56° C. using S. cerevisiae genomic DNA as template. Fragments AD1 (k1URA 3' end fused to promoter ADH1) and AD2 (promoter ADH1 fused to K1URA 5'-end) were generated via PCR using primers AD-fw and Int3' and Int5' and AD-ry at a melting temperature of 56° C. and 56° C., respectively. Plasmid pWAD1 was used as template for generation of fragment AD1 and plasmid pWAD2 was used for generating fragment AD2. Fragments CPR_UP were then fused to fragment AD2 using fusion PCR with primers A and Int3' at a melting temperature of 56° C. resulting in fusion fragment 1 (bi-partite substrate 1). A second fusion PCR was used to fuse fragments AD1 and CPR-S with Int5' and primer D at a melting temperature of 56° C. resulting in fusion fragment 2 (bi-partite substrate 2).

Fusion fragments 1 and 2 (bi-partite substrates 1 and 2) were purified on agarose gel and used for co-transformation of S. cerevisiae strain FS01528 (Mata, ura3 his3) and the transformants were plated on SC-URA plates and incubated for 2-4 days at 30° C. Transformants were streak purified on SC-ura plates and incubated another 2 days at 30° C. and then plated onto 5-FOA (5-fluoroorotic acid) plates. After incubation for 2 days at 30° C. "pop-out" colonies appeared, which were streak purified on a new 5-FOA-plate and incubated another 2 days at 30° C. and then finally transferred to a rich medium plate YPD. The resulting colonies were analyzed for the presence of fragment of size 1700-1800 base pairs using yeast colony PCR with primers A and AD-rev and a melting temperature of 55° C. and an elongation time of 1 minute and 45 seconds. One of the positive colonies from the colony PCR containing the new replaced ADH1 promoter in front of the CPR1 gene was named FSpADH1-CPR (Mata ura3 his3 pADH1-CPR1) strain.

Table 1 Primers and fragments used in the "bi-partite" PCR-based allele replacement method to exchange native S. cerevisiae CPR1 promoter with S. cerevisiae ADH1 promoter

```
Primers
A 5'-GTATTCTATATCCACGCCTGCAAAC

B 5'-
AGTACATACAGGGAACGTCCCTACAGGAACGCAAACTTAAGCTAC

C 5'-
GCATACAATCAACTATCTCATATACAATGCCGTTTGGAATAGACAACACC

D 5'-GCTTCCGCATTACAAATAAAGTCTTCAA

AD-fw
5'-GGACGTTCCCTGTATGTACTAGGGGGATCGAAGAAATGATGG

Int3' 5'-GAGCAATGAACCCAATAACGAAATC 3'

Int5' 5'-CTTGACGTTCGTTCGACTGATGAGC 3'

AD-rv 5'-TGTATATGAGATAGTTGATTGTATGC

Fragments
CPR-UP generated from primers A and B
(CPR1 gene fragment upstream of start
codon (ATG))

CPR-S generated from primers C and D
(CPR1 gene fragment containing start
codon (ATG))

AD1 (ADH1 promoter coupled to two thirds
of K.lactis URA3 towards the 5' end
generated from primers AD-fw and Int3')

AD2 (Two thirds of K.lactis URA3
towards the 3' end coupled to the ADH1
promoter. Generated from primers Int5'
and AD-rv)

Fusion fragment 1 (CPR-UP fragment fused
to AD2 fragment)

Fusion fragment 2 (AD1 fragment fused to
CPR-S fragment)
```

Example 37

Construction of a Strain Overexpressing Native S. cerevisiae ACC1 Gene

The yeast gene ACC1, encoding acetyl-CoA carboxylase, was overexpressed with the strong constitutive yeast TPI1 promoter as described previously (WO 2005/118814). This was done by replacing the native ACC1 promoter with the TPI1 promoter, using a slightly modified promoter-replacement method based on the bipartite gene-targeting method (Example 1 and 2). One part of the bipartite substrate consisted of two thirds (towards the 3' end) of K. lactis URA3, fused to the TPI1 promoter sequence and a target sequence corresponding to the beginning of ACC1. The second part of the bipartite substrate consisted of a target sequence upstream of ACC1, fused to the TPI1 promoter sequence and two thirds (towards the 5' end) of K. lactis URA3. Following transformation with the bipartite substrate and selection on medium lacking uracil, transformants were obtained in which the native promoter had been knocked out and replaced with two copies of the TPI1 promoter sequence as a direct repeat on either side of the K. lactis URA3 marker gene. A second recombination event, resulting in looping out of the selection marker, was selected for by replating transformants on medium containing 5'-fluoroorotic acid (5-FOA), which is toxic to cells expressing the URA3 gene. This resulted in a strain, in which the native ACC1 promoter had been replaced with the TPI1 promoter.

In order to construct part 1 of the bipartite substrate, two thirds (towards the 3' end) of K. lactis ura3 was amplified from the plasmid pWJ716 using the primers 5' CTTGACGTTCGTTCGACTGATGAGC 3' and 5' CTGGAATTCGATGATGTAGTTTCTGG 3' (Table 2). Moreover, the TPI1 promoter sequence was amplified from genomic yeast DNA using the primers 5' CTACATCATCGAATTCCAGCTACGTATGGTCATTTCTTCTTC 3' and 5' TTTTTGATTAAAATTAAAAAAAACTTTTTAGTTTATGTATGTGTTTTTTG 3' and a downstream targeting sequence, consisting of the beginning of the ACC1 gene (i.e., the first 553 bp of the gene) was amplified from genomic yeast DNA using the primers 5' AGTTTTTTTAATTTTAATCAAAAAATGAGCGAAGAAAGCTTATTCGAGTC 3' and 5' CACCTAAAGACCTCATGGCGTTACC 3'. These three fragments were fused to each other in two rounds of PCR. First, the TPI1 promoter sequence was fused to the downstream targeting sequence, using the primers 5' CTACATCATCGAATTCCAGCTACGTATGGTCATTTCTTCTTC 3' and 5' CACCTAAAGACCTCATGGCGTTACC 3'. The resulting product was then fused to the fragment containing two thirds (towards the 3' end) of K. lactis URA3. The resulting fragment, 3' 2/3 K. lactis URA3-pTPI1-DOWN (ACC1) was part 1 of the bipartite gene targeting substrate.

In order to construct part 2 of the bipartite substrate, two thirds (towards the 5'-end) of K. lactis URA3 was amplified from the plasmid pWJ716 using the primers 5' CGGTCTGCATTGGATGGTGGTAAC 3' and 5' GAGCAATGAACCCAATAACGAAATC 3' (Table 2). The TPI1 promoter sequence was amplified from genomic yeast DNA using the primers 5' CTACATCATCGAATTCCAGCTACGTATGGTCATTTCTTCTTC 3' and 5' CACCATCCAATGCAGAC- CGTTTTAGTTTATGTATGTGTTTTTTG 3', and a target sequence upstream of ACC1 was amplified from genomic DNA using primers 5' TGTTCTGCTCTCTTCAATTTTC-CTTTC 3' and 5' CTGGAATTCGATGATG-TAGTTTCTAATTTTCTGCGCTGTTTCG 3'. These three fragments were fused in two rounds of PCR. First, the upstream targeting sequence was fused to the TPI1 promoter sequence, using the primers 5' TGTTCTGCTCTCT-TCAATTTTCCTTTC 3' and 5' CACCATCCAATGCA-GACCGTTTTAGTTTATGTATGTGTTTTTTG 3'. The resulting fragment was then fused to the fragment containing two thirds (towards the 5' end) of K. lactis URA3, resulting in the fragment UP (ACC1)-pTPI1-5' 2/3 K. lactis URA3, which constituted part 2 of the bipartite gene targeting substrate.

Yeast strain FS01372 (MATa ura3 trp1 PADH1-FAS1 pADH1-FAS2) was transformed with the linear substrates UP (ACC1)-pTPI1-5' 2/3 K. lactis URA3 and 3' 2/3 K. lactis URA3-pTPI1-DOWN (ACC1). Transformants were selected and streak-purified on medium lacking uracil and were then transferred to plates containing 5-FOA. Pop-out recombinants were streak-purified on 5-FOA-containing medium. The resulting strain was named FS01392 and had the genotype MATa ura3 trp1 pTPI1-ACC1 PADH1-FAS1 pADH1-FAS2). The correct integration of the TPI1 promoter was checked by colony PCR.

Table 2 Primers and fragments used in the "bi-partite" PCR-based allele replacement method to exchange native S. cerevisiae ACC1 promoter with the strong constitutive S. cerevisiae TPI1 promoter

```
Primers
A 5'-CTTGACGTTCGTTCGACTGATGAGC

B 5'-CTGGAATTCGATGATGTAGTTTCTGG

C 5'-CTACATCATCGAATTCCAGCTACGTATGGTCATTTCTTCTTC

D 5'-
TTTTTGATTAAAATTAAAAAAACTTTTTAGTTTATGTATGTGTTTTTTG

E 5'-
AGTTTTTTTAATTTTAATCAAAAAATGAGCGAAGAAAGCTTATTCGAGTC

F 5'-CACCTAAAGACCTCATGGCGTTACC

G 5'-CTACATCATCGAATTCCAGCTACGTATGGTCATTTCTTCTTC
(G = C)

H 5'-CACCTAAAGACCTCATGGCGTTACC
(H = F)

I 5'-CGGTCTGCATTGGATGGTGGTAAC

J 5'-GAGCAATGAACCCAATAACGAAATC

K 5'-CTACATCATCGAATTCCAGCTACGTATGGTCATTTCTTCTTC

L 5'-CACCATCCAATGCAGACCGTTTTAGTTTATGTATGTGTTTTTTG

M 5'-TGTTCTGCTCTCTTCAATTTTCCTTTC

N 5'-CTGGAATTCGATGATGTAGTTTCTAATTTTCTGCGCTGTTTCG

O 5'-TGTTCTGCTCTCTTCAATTTTCCTTTC
(O = M)

P 5'-CACCATCCAATGCAGACCGTTTTAGTTTATGTATGTGTTTTTTG
(P = L)

Fragments
KlactisURA3 sequence generated with primers
A and B

TPI1 promoter sequence generated with primers
C and D

ACC1 downstream sequence generated with
primers E and F pTPI1-Down(ACC1) fusion generated from primers
G and H KlactisURA3-pTPI1-DOWN(ACC1) = part 1 of the
bipartite substrate generated from primers
A and H KlactisURA3 sequence generated with primers
I and J TPI1 promoter sequence generated with primers
K and L ACC1 upstream sequence generated with primers
M and N UP(ACC1)-pTPI1 fusion generated from primers
O and P UP(ACC1)-pTPI1-5'KlactisURA3 = part 2 of the
bipartite substrate generated with primers
M and J
```

Example 38

Deletion of Native Yeast Genes by Gene Targeting Method

Gene deletions were performed by a similar method as for gene overexpressions (Example 1) by means of homologous recombination using PCR-generated targeting substrates and the K. lactis URA3 gene as a selectable marker, essentially as described in Erdeniz, N., Mortensen, U. H., Rothstein, R. (1997) Genome Res. 7:1174-83. Information on primer design for fusion PCR can be found in the same publication. Generally, fusion of DNA fragments was made possible by using primers with appropriately designed 5' overhangs for amplification of the original DNA fragments. In all cases, PCR-generated fragments were excised from a 1% agarose gel and purified before proceeding with fusion PCR.

Transformants were generally selected on -URA plates, and pop-out of the K. lactis URA3 marker gene was selected for by plating on 5-FOA medium (5-fluoroorotic acid, 750 mg/l). Correct gene deletions were verified by PCR, using primers on both sides of the deleted gene. Generally, PCR-verification of gene deletions was performed by means of colony-PCR. For colony-PCR, a small amount of cells was dispersed in 10 μl H$_2$O and was placed at −80° C. for approximately 30 min, followed by 15 min. incubation at 37° C. The cell suspension was then used as template for PCR.

Example 39

Generation of Strain with Deleted Isocitrate Dehydrogenase, IDH1

The Native Yeast Gene IDH1

SEQ ID NO: 59
ATGCTTAACAGAACAATTGCTAAGAGAACTTTAGCCACTGCCGCTCAGGC

GGAACGCACCCTACCCAAGAAGTATGGCGGTCGTTTCACCGTCACTTTGA

-continued

```
TACCTGGTGACGGTGTTGGGAAAGAAATCACTGATTCAGTGAGAACCATT

TTTGAGGCTGAAAATATCCCGATCGACTGGGAAACTATAAACATTAAGCA

AACAGATCATAAGGAAGGCGTCTATGAAGCTGTTGAGTCTCTAAAGAGAA

ATAAGATTGGTCTTAAGGGGCTATGGCACACTCCTGCTGACCAAACAGGT

CACGGTTCACTAAACGTTGCTTTGCGTAAACAACTAGATATCTACGCCAA

TGTGGCCCTTTTCAAATCCTTGAAGGGTGTCAAGACTAGAATTCCAGACA

TAGATTTGATTGTCATTAGAGAAAACACGGAGGGTGAGTTCTCAGGCCTG

GAACATGAATCCGTCCCTGGTGTAGTGGAATCTTTGAAAGTTATGACTAG

ACCTAAGACAGAAAGGATCGCCAGATTTGCCTTTGACTTCGCCAAGAAAT

ACAACAGAAAGTCTGTCACAGCTGTGCATAAGGCAAATATCATGAAGTTA

GGTGACGGTCTGTTCAGAAATATAATAACTGAAATTGGCCAAAAAGAATA

TCCTGATATTGACGTATCGTCCATCATTGTCGACAATGCCTCCATGCAGG

CGGTGGCCAAACCTCATCAATTTGATGTCCTAGTTACCCCTTCAATGTAC

GGTACCATCTTAGGCAACATTGGCGCTGCTTTGATCGGTGGTCCAGGATT

GGTGGCAGGTGCCAACTTTGGCAGGGACTATGCTGTCTTCGAACCAGGTT

CCAGACATGTTGGTTTAGATATTAAAGGCCAAAATGTGGCTAACCCAACT

GCCATGATCCTTTCCTCCACGTTAATGTTGAACCATTTGGGTTTGAATGA

ATATGCTACTAGAATCTCAAAGGCAGTTCATGAAACGATCGCAGAAGGTA

AGCATACCACTAGAGATATTGGTGGTTCCTCTTCTACTACTGACTTCACG

AATGAAATCATCAACAAATTATCTACCATGTAA
``` encoded by YNL037c is deleted using a quadruple gene targeting substrate according to the following procedure:

A target sequence upstream of IDH1 gene is amplified from genomic DNA by PCR using the primers IDH1-up-fw and IDH1-up-ry and is fused to the two thirds of the *K. lactis* URA3 gene to the 5' end by PCR. Furthermore a target sequence corresponding to the downstream region of IDH1 is amplified from genomic DNA using the primers IDH1-D-fw and IDH1-d-rv. The downstream target sequence is fused to the two thirds of the *K. lactis* URA3 gene to the 3' end by PCR.

The yeast strain FS01528 (MATa ura3 his3) is transformed with the two linear fusion substrates described above containing the upstream target region and the downstream target region of the gene to be deleted fused to either two thirds of the *K. lactis* URA3 gene. Transformants are selected on medium lacking uracil and are streak-purified on the same medium. Transformants are transferred to plates containing 5-FOA. Pop-out recombinants are streak-purified on 5-FOA-containing medium. The resulting strain has the genotype (MATa ura3 his3 IDH1Δ). Correct deletion of the IDH1 gene is verified by PCR using the primers IDH1-up-fw and IDH1-D-rv.

Example 40

Mating of Cells, Sporulation, Tetrad Dissection and Tetrad Scoring (Analysis)

Methods for combining genetic features by crossing of strains used in the examples are well known and are, e.g., described in: Adams, A., Gottschling, D. E., Kaiser, C. A., and Stearns, T. Methods in Yeast Genetics: A Cold Spring Harbor Laboratory Course Manual, Cold Spring Harbor Laboratory Press, Cold Spring Harbor, N.Y. (1997). Typically, strains of opposite mating types were allowed to mate, diploids were selected and transferred to sporulation medium (20 g/l potassium acetate, 1 g/l glucose, 2.5 g/l yeast extract, pH 7.0) and were allowed to sporulate at 30° C. for approximately 3 days. The asci were dissected on a YPD plate using a Singer MSM microscope and micromanipulator dissection microscope. The mating types of the resulting tetrads were scored by replica-plating to a lawn of cells with either a or alpha mating type, incubating at 30° C. to allow mating, replica-plating to sporulation medium, and visualizing sporulation by illuminating plates under a 302 nm UV-light source. Auxotrophic markers were scored by replica plating to drop-out plates. Genetic modifications that could not be scored by phenotype were scored by colony-PCR. In general, the same primer sets that were used for verification of genomic integrations or knockouts were also used for colony-PCR scoring of tetrads.

Example 41

Isolation of Genes Encoding TAL, PAL, C4H, 4CL, and VST1

Tyrosine ammonia lyase (TAL) was isolated from *Rhodobacter capsulatus* by codon optimization for expression in *S. cerevisiae* and was further assembled as a synthetic gene as described above.

The isolation of phenylalanine ammonia lyase (PAL2), cinnamate 4-hydroxylase (C4H), 4-coumarate:CoenzymeA ligase (4CL1) described above.

4-Coumarate:CoenzymeA Ligase (4CL2)

```
                                        (SEQ ID NO: 60)
ATGACGACACAAGATGTGATAGTCAATGATCAGAATGATCAGAAACAGTG

TAGTAATGACGTCATTTTCCGATCGAGATTGCCTGATATATACATCCCTA

ACCACCTCCCACTCCACGACTACATCTTCGAAAATATCTCAGAGTTCGCC

GCTAAGCCATGCTTGATCAACGGTCCCACCGGCGAAGTATACACCTACGC

CGATGTCCACGTAACATCTCGGAAACTCGCCGCCGGTCTTCATAACCTCG

GCGTGAAGCAACACGACGTTGTAATGATCCTCCTCCCGAACTCTCCTGAA

GTAGTCCTCACTTTCCTTGCCGCCTCCTTCATCGGCGCAATCACCACCTC

CGCGAACCCGTTCTTCACTCCGGCGGAGATTTCTAAACAAGCCAAAGCCT

CCGCGGCGAAACTCATCGTCACTCAATCCCGTTACGTCGATAAAATCAAG

AACCTCCAAAACGACGGCGTTTTGATCGTCACCACCGACTCCGACGCCAT

CCCCGAAAACTGCCTCCGTTTCTCCGAGTTAACTCAGTCCGAAGAACCAC

GAGTGGACTCAATACCGGAGAAGATTTCGCCAGAAGACGTCGTGGCGCTT

CCTTTCTCATCCGGCACGACGGGTCTCCCCAAAGGAGTGATGCTAACACA

CAAAGGTCTAGTCACGAGCGTGGCGCAGCAAGTCGACGGCGAGAATCCGA

ATCTTTACTTCAACAGAGACGACGTGATCCTCTGTGTCTTGCCTATGTTC

CATATATACGCTCTCAACTCCATCATGCTCTGTAGTCTCAGAGTTGGTGC

CACGATCTTGATAATGCCTAAGTTCGAAATCACTCTCTTGTTAGAGCAGA

TACAAAGGTGTAAAGTCACGGTGGCTATGGTCGTGCCACCGATCGTTTTA

GCTATCGCGAAGTCGCCGGAGACGGAGAAGTATGATCTGAGCTCGGTTAG
```

```
GATGGTTAAGTCTGGAGCAGCTCCTCTTGGTAAGGAGCTTGAAGATGCTA

TTAGTGCTAAGTTTCCTAACGCCAAGCTTGGTCAGGGCTATGGGATGACA

GAAGCAGGTCCGGTGCTAGCAATGTCGTTAGGGTTTGCTAAAGAGCCGTT

TCCAGTGAAGTCAGGAGCATGTGGTACGGTGGTGAGGAACGCCGAGATGA

AGATACTTGATCCAGACACAGGAGATTCTTTGCCTAGGAACAAACCCGGC

GAAATATGCATCCGTGGCAACCAAATCATGAAAGGCTATCTCAATGACCC

CTTGGCCACGGCATCGACGATCGATAAAGATGGTTGGCTTCACACTGGAG

ACGTCGGATTTATCGATGATGACGACGAGCTTTTCATTGTGGATAGATTG

AAAGAACTCATCAAGTACAAAGGATTTCAAGTGGCTCCAGCTGAGCTAGA

GTCTCTCCTCATAGGTCATCCAGAAATCAATGATGTTGCTGTCGTCGCCA

TGAAGGAAGAAGATGCTGGTGAGGTTCCTGTTGCGTTTGTGGTGAGATCG

AAAGATTCAAATATATCCGAAGATGAAATCAAGCAATTCGTGTCAAAACA

GGTTGTGTTTTATAAGAGAATCAACAAAGTGTTCTTCACTGACTCTATTC

CTAAAGCTCCATCAGGGAAGATATTGAGGAAGGATCTAAGAGCAAGACTA

GCAAATGGATTAATGAACTAG
``` was isolated via PCR from *A. thaliana* cDNA (BioCat, Heidelberg, Germany) using the forward primer 5'-GCGAATTCTTATGACGACA CAAGATGTGATAGTCAATGAT-3' containing an EcoR1 restriction site and reverse primer 5'-GCACTAGTATCCTAGTTCATTAATCCATTT GCTAGTCTTGCT-3' containing a Spe1 restriction site.

The VST1 gene encoding *Vitis vinifera* (grapevine) resveratrol synthase (Hain et al, 1993) was synthesized by GenScript Corporation (Piscataway, N.J.). The amino acid sequence:

```
                                                    (SEQ ID NO: 63)
  1 MASVEEFRNA QRAKGPATIL AIGTATPDHC VYQSDYADYY FRVTKSEHMT

51 ELKKKFNRIC DKSMIKKRYI HLTEEMLEEH PNIGAYMAPS LNIRQEIITA

101 EVPRLGRDAA LKALKEWGQP KSKITHLVFC TTSGVEMPGA DYKLANLLGL

151 ETSVRRVMLY HQGCYAGGTV LRTAKDLAEN NAGARVLVVC SEITVVTFRG

201 PSEDALDSLV GQALFGDGSS AVIVGSDPDV SIERPLFQLV SAAQTFIPNS

251 AGAIAGNLRE VGLTFHLWPN VPTLISENIE KCLTQAFDPL GISDWNSLFW

301 IAHPGGPAIL DAVEAKLNLE KKKLEATRHV LSEYGNMSSA CVLFILDEMR

351 KKSLKGEKAT TGEGLDWGVL FGFGPGLTIE TVVLHSVPTV TN**
``` was used as template to generate a synthetic gene optimized for expression in *S. cerevisiae*:

```
ATGGCATCCGTAGAGGAGTTCAGAAATGCACAGAGGGCAAAAGG

TCCAGCAACCATATTGGCTATTGGAACAGCCACCCCTGATCACTGTGTTT

ATCAATCTGATTACGCTGATTACTATTTCAGAGTAACTAAAAGTGAACAT

ATGACAGAACTTAAGAAAAAGTTTAATAGAATTTGTGATAAATCTATGAT

AAAGAAAAGATACATACATCTAACTGAAGAAATGTTAGAGGAACATCCAA

ATATAGGTGCATATATGGCACCATCTTTGAATATTAGACAAGAAATCATA

ACAGCCGAGGTACCTAGACTAGGTAGAGACGCAGCCTTGAAAGCTTTAAA

GGAATGGGGACAACCAAAATCTAAGATTACACATTTGGTTTTCTGTACAA

CTTCCGGTGTCGAAATGCCAGGTGCTGATTATAAACTAGCAAACCTATTG

GGATTAGAGACCTCTGTTAGAAGAGTTATGTTGTATCATCAAGGTTGTTA

CGCCGGAGGTACAGTGCTTAGAACTGCTAAGGATTTGGCAGAAAATAACG

CCGGTGCTAGGGTTTTAGTCGTCTGCAGTGAAATCACTGTCGTAACTTTC

AGAGGTCCATCAGAAGATGCTCTAGACAGTTTGGTCGGACAAGCATTGTT

TGGCGATGGATCTTCCGCCGTAATTGTAGGCAGCGATCCTGATGTGTCCA

TTGAAAGACCACTATTTCAATTAGTTTCTGCTGCTCAAACTTTTATTCCA

AATTCCGCCGGTGCCATAGCAGGAAACTTGAGAGAAGTTGGTTTGACTTT

TCATTTGTGGCCTAATGTCCCAACCTTAATTTCAGAAAACATCGAAAAAT

GCTTAACTCAAGCCTTTGACCCATTGGGCATAAGCGACTGGAACTCATTG

TTTTGGATTGCTCATCCAGGTGGTCCAGCAATTTTAGACGCAGTGGAGGC

AAAACTAAACTTAGAGAAGAAAAAGTTGGAAGCTACAAGACACGTTCTAT

CAGAGTATGGCAACATGAGCTCTGCCTGCGTTTTATTCATTCTAGATGAG

ATGAGGAAGAAGTCTTTAAAGGGTGAAAAAGCCACAACCGGAGAAGGTTT

AGATTGGGGTGTTCTATTTGGTTTCGGTCCTGGCTTAACAATTGAGACAG

TGGTGTTACACTCTGTTCCAACTGTCACTAACTAATGA
```

(SEQ ID NO: 64). The synthetic VST1 gene was delivered inserted in *E. coli* pUC57 vector flanked by BamH1 and Xho1 restriction sites. The synthetic gene was purified from the pUC57 vector by BamH1/Xho1 restriction and purified from agarose gel using the QiaQuick Gel Extraction Kit (Qiagen).

Example 42

Construction of a Yeast Vector for Expression of TAL

Plasmid, pESC-URA-TAL, containing the gene encoding tyrosine ammonia lyase, TAL, under the control of the divergent GAL1/GAL10 promoter was constructed as described above for PAL.

Example 43

Construction of a Yeast Vector for Expression of 4CL

The gene encoding 4CL1 and 4CL2 were isolated as described above. The amplified 4CL1 PCR-product was digested with Xba1/BamH1 and ligated into Spe1/BglII digested pESC-TRP vector (Stratagene), resulting in vector pESC-TRP-4CL. The amplified 4CL2 PCR-product was digested with EcoR1/Spe1 and ligated into EcoR1/Spe1 digested pESC-HIS vector (Stratagene), resulting in vector pESC-HIS-4CL2.

Two different clones of pESC-TRP-4CL1 and pESC-HIS-4CL2 were sequenced to verify the sequence of the cloned gene.

Example 44

Construction of a Yeast Vectors for Expression of 4CL and VST

The gene encoding VST from *Vitis vinifera* (grape) was isolated as described above. The purified BamH1/Xho1 digested VST gene fragment was ligated into BamH1/Xho1 digested pESC-HIS-4CL2 plasmid or pESC-trp-4CL1 plasmid (example 15). The resulting plasmids, pESC-HIS-4CL2-VST and pESC-TRP-4CL1-VST contained the genes encoding 4CL1, 4CL2 and VST under the control of the divergent GAL1/GAL10 promoter. The sequence of the gene encoding VST was verified by sequencing of two different clones of pESC-HIS-4CL2-VST and pESC-TRP-4CL1-VST.

Example 45

Expression of the PAL-Pathway to Resveratrol in the Yeast *S. cerevisiae* Using PAL, C4H, 4CL and VST Yeast strains containing the appropriate genetic markers were transformed with the vectors described in examples 36 and 38. The transformation of the yeast cell was conducted in accordance with methods known in the art, for instance, by using competent cells or by electroporation (see, e.g., Sambrook et al., 1989).

*S. cerevisiae* strain FS01267 (MATa ura3 trp1) was co-transformed with the vectors pESC-URA-PAL-C4H and pESC-TRP-4CL1-VST, resulting in the strain FSSC-PALC4H4CL1VST.

*S. cerevisiae* strain FS01528 (MATa ura3 his3) was co-transformed with the vectors pESC-URA-PAL-C4H and pESC-HIS-4CL2-VST, resulting in the strain FSSC-PALC4H4CL2VST.

Transformants were selected on medium lacking uracil and tryptophan or uracil and histidine and streak purified on the same medium.

Example 46

Expression of the TAL-Pathway to Resveratrol in *S. cerevisiae* Using TAL, 4CL and VST

*S. cerevisiae* strain FS01528 (MATa ura3 his3) was co-transformed with pESC-URA-TAL (example 42) and pESC-HIS-4CL2-VST (example 44), and the transformed strain was named FSSC-TAL4CL2VST. Transformants were selected on medium lacking uracil and histidine and streak purified on the same medium.

Example 47

Expression of the PAL-Pathway to Resveratrol in *S. cerevisiae* Strain Overexpressing Native *S. cerevisiae* NADP-Cytochrome P450 Reductase FSpADH1-CPR (Mata ura3 his3 pADH1-CPR1) (Example 36) was co-transformed with the vectors pESC-URA-PAL-C4H and pESC-HIS-4CL2-VST, resulting in the strain FSSC-PALC4H4CL2VST-pADH1CPR1 (Mata ura3 his3 pADH1-CPR1, pESC-URA-PAL-C4H, pESC-HIS-4CL2-VST).

Example 48

Expression of the PAL-Pathway to Resveratrol in *S. cerevisiae* Strain Overexpressing Native *S. cerevisiae* ACC1 Gene FS01392 (MATa ura3 trp1 pTPII-ACC1 PADH1-FAS1 pADH1-FAS2) (example 37) was co-transformed with the vectors pESC-URA-PAL-C4H and pESC-TRP-4CL1-VST, resulting in the strain FS01392-PAL.

As a control the strain FS01372 (MATa ura3 trp1 pTPII-ACC1 PADH1-FAS1 pADH1-FAS2)(Example 37) was also co-transformed with the vectors pESC-URA-PAL-C4H and pESC-TRP-4CL1-VST, resulting in the strain FS01372-PALcon.

Example 49

Expression of the TAL-Pathway to Resveratrol in *S. cerevisiae* Strain Overexpressing Native *S. cerevisiae* ACC1 Gene FS01392 (MATa ura3 trp1 pTPII-ACC1 PADH1-FAS1 pADH1-FAS2) (example 37) was co-transformed with the vectors pESC-URA-TAL and pESC-TRP-4CL1-VST, resulting in the strain FS01392-TAL.

As a control the strain FS01372 (MATa ura3 trp1 pTPI1-ACC1 PADH1-FAS1 pADH1-FAS2)(Example 37) was also co-transformed with the vectors pESC-TAL and pESC-TRP-4CL1-VST, resulting in the strain FS01372-TALcon.

Example 50

HPLC Analysis of Hydroxyl Stilbenes

For quantitative analysis of cinnamic acid, coumaric acid, pinosylvin and resveratrol, cell free supernatant samples were subjected to separation by high-performance liquid chromatography (HPLC) Agilent Series 1100 system (Hewlett Packard) prior to uv-diode-array detection at $\lambda=306$ nm. A Phenomenex (Torrance, Calif., USA) Luna 3 micrometer C18 (100×2.00 mm) column was used at 40° C. As mobile phase a gradient of acetonitrile and milliq water (both containing 50 ppm trifluoroacetic acid) was used at a flow of 0.4 ml/min. The gradient profile was linear from 15% acetonitrile to 100% acetonitrile over 20 min. The elution times were approximately 3.4 min. for coumaric acid, 5.5 min. for free trans-resveratrol and 6.8 min. for cinnamic acid. The elution time was approximately 8.8-8.9 minutes for trans-pinosylvin.

Pure pinosylvin standard (>95% pure) was purchased from ArboNova (Turku, Finland). Pure resveratrol standard was purchased from Cayman chemical company, whereas pure coumaric acid and cinnamic acid standards were purchased from Sigma.

Example 51

Shake Flask Cultivations of Strain Overexpressing CPR

The metabolically engineered recombinant yeast strain with overexpressed CPR, FSSC-PALC4H4CL2VST-pADH1CPR1 (example 19), was inoculated to an initial optical density of 0.1 and grown in 100 ml defined mineral medium (Verduyn et al, 1992) that contained vitamins, trace elements, 3 g/l glucose and 40 g/l galactose for induction of the PAL-pathway genes. The control strain FSSC-PALC4H4CL2VST (example 17) was inoculated in the same way in a second shake flask for control comparison.

The 500 ml stoppered shake flasks were incubated for three days at 30° C. and 110 rpm. At 72 hours 1 ml samples were taken out from the cultivations, cells were removed by 1 minute centrifugation (13000 rpm, micro centrifuge), and the cell free supernatant was analyzed with HPLC.

The engineered strain overexpressing CPR produced 12.0 mg/l resveratrol compared to the control strain that produced 1.0 mg/l resveratrol after 72 hours cultivation.

| Strain | Resveratrol (mg/l) |
|---|---|
| Control FSSC-PALC4H4CL2VST | 1.0 |
| Overexpressed CPR FSSC-PALC4H4CL2VST-pADH1CPR1 | 12.0 |

Example 52

Shake Flask Cultivations of Strains Overexpressing ACC1

The metabolically engineered recombinant yeast strains with overexpressed ACC1, FS01392-PAL (example 20a) and FS01392-TAL (example 20b), were inoculated to an initial optical density of 0.1 and grown in 100 ml defined mineral medium (Verduyn et al, 1992) that contained, vitamins, trace elements, 3 g/l glucose and 40 g/l galactose for induction of the PAL-pathway genes. After 24 hours 50 mg coumaric acid (Sigma) precursor dissolved in 1 ml 70% ethanol was added corresponding to a concentration of 500 mg/l coumaric acid in the shake flasks.

The control strains, FS01372-PALcon (example 20a) and FS01372-TAlcon (example 20b), were inoculated and grown in the same way in a second shake flask for control comparison.

The 500 ml stoppered shake flasks were incubated for three days at 30° C. and 110 rpm. At 68 hours 1 ml samples were taken out from the cultivations, cells were removed by 1 minute centrifugation (13000 rpm, micro centrifuge), and the cell free supernatant was analyzed with HPLC.

The engineered strain FS01392-PAL (overexpressing ACC1 and the PAL-pathway genes produced) 119 mg/l resveratrol and its control strain FS01372-PALcon produced 104 mg/l resveratrol, corresponding to a 14% increase in the engineered strain.

The engineered strain FS01392-TAL (overexpressing ACC1 and the TAL-pathway genes produced) 99.5 mg/l resveratrol and its control strain FS01372-TALcon produced 69 mg/l resveratrol, corresponding to a 44% increase in the engineered strain.

| Strain | Resveratrol (mg/l)* |
|---|---|
| FS01392-PAL Overexpressed ACC1 | 119.0 |
| Control-PAL FS01372-PALcon | 104.0 |
| FS01392-TAL Overexpressed ACC1 | 99.5 |
| Control-TAL FS01372-TALcon | 69.0 |

*In these experiments 500 mg/l coumaric acid was added to the shake flasks.

Example 53

Resveratrol Content of Genetically Engineered Yeast Cells

The resveratrol content of yeast cells genetically engineered to produce resveratrol as described in Example 9 was determined. Levels of from 0.44 to 0.53 μg/g were found.

Example 53

Determination of Intracellular and Extracellular Levels of Stilbenoids in a Continuous Culture of PALCPR The yeast strain with overexpressed CPR, FSSC-PALC4H4CL2VST-pADH1CPR1 (see Example 47) was grown in a carbon-limited continuous culture with a working volume of 1 liter. The culture was fed with a defined medium according to Verduyn et al. (1992), containing: 5.0 g/L $(NH_4)_2SO_4$; 3.0 g/L $KH_2PO_4$; 0.5 g/L $MgSO_4.7H2O$; trace metals and vitamins and 5 g/l glucose and 35 g/l galactose as the growth-limiting nutrients. Antifoam (300 μl/L, Sigma A-8436) was added to avoid foaming. The carbon source was autoclaved separately from the mineral medium and afterwards added to the fermentor. In addition, the vitamin and trace metal solutions were added to the fermentor by sterile filtration following autoclavation and cooling of the medium. The fermentor system was from Sartorius BBI systems and consisted of a baffled 3-liter reactor vessel with 1 liter working volume equipped with Biostat B Plus controller. The reactor vessel was equipped with two Rushton turbines which were rotating at either 1000 rpm, the temperature was kept at 30±1° C., and the pH was kept at 5.5±0.2 by automatic addition of 2M KOH. The gasflow was controlled by a mass flow controller and was set to 1.5 vvm (1.5 l/min). The off-gas was led through a cooled condenser, and was analyzed for $O_2$ and $CO_2$ (Model 1308, Innova, Denmark). An initial batch culture with 35 g/l galactose was started by inoculation of the culture with 10 ml of an exponential growing shakeflask culture containing 5 g/l glucose and 35 g/l galactose. The batch cultivation was switched to a continuous mode by feeding the same medium continuously to the reactor. The dilution rate was controlled on a constant level basis, aiming at D=0.050 $h^{-1}$. The continuous culture was regarded to be in steady state when both the dilution rate and off-gas signal had not changed for at least five residence times, and when the metabolite concentrations in two successive samples taken at intervals of 1 residence time, deviated by less than 3%. The dissolved-oxygen concentration, which was continuously monitored, was kept above 60% of air saturation. Under said conditions the strain consumed all the galactose, and mainly produced biomass and $CO_2$, and only minor amounts of ethanol. Moreover, the RQ was close to unity, indicating that metabolism was predominantly in respiratory mode.

For the determination of stilbenoids, samples were taken at approximately 300 hrs into fermentation corresponding to 15 residence times. Cells were harvested by centrifugation 5000 g for 5 minutes. For the determination of extracellular levels of stilbenoids, an aliquot of 25 ml of supernatant was extracted once with 10 ml ethyl acetate. The ethyl acetate was freeze dried and the dry product redissolved in 0.6 ml methanol. The samples were than 50-fold diluted in water transferred into HPLC vials, and analyzed by HPLC. Furthermore, to evaluate whether the level of stilbenoids that was produced exceeded the solubility of the medium, or were either bound to the cell-membranes 1 ml aliquots of cell culture, thus including both cells and medium, were mixed with 1 ml of 100% ethanol, and mixed vigorously prior to centrifugation. The supernatant was then transferred into HPLC vials, and directly analyzed for the content of stilbenoids. For the determination of intracellular levels of stilbenoids, an aliquot of 50 ml culture was sampled, and cells and medium were separated by centrifugation. The pellet was washed with 50 ml of water to remove any stilbenoids that were cell-bound or trapped into the pellet; after re-centrifugation the pellet was then dissolved in 1 ml water. The resulting cell suspension was distributed into extraction tubes and broken with glass beads using a fast-prep machine. The crude extracts were pooled into 10 ml of 100% methanol, and extracted in a rotary chamber for 24 hours in a dark cold room at 4° C. Thereafter, the cell debris was removed via centrifugation for 5 min. at 5000 g and the remaining methanol was removed by freeze-drying overnight. The dry residue was redissolved in 0.4 ml methanol and 0.1 ml water. The samples were than 50-fold diluted in water and then transferred into HPLC vials, and analyzed by HPLC.

The following table summarizes the results:

Intracellular levels of stilbenoids were expressed in mg per gram biomass (dry weight), according to the calculation explained in the following section. The concentration of resveratrol and pinosylvin in the extract was determined as 227 mg/l and 1646 mg/l respectively; the volume of the extract was 0.5 ml, hence the absolute amount of resveratrol and pinosylvin extracted was 0.5*227/1000=0.1135 mg and 0.5*1646/1000=0.8230 mg respectively. The stilbenoids were extracted from a 50 ml culture-aliquot and hence the intracellular concentrations of resveratrol and pinosylvin expressed per liter culture were 0.1135*(1000/50)=2.27 mg/l and 0.8230*(1000/50)=16.46 mg/l. The biomass concentration of said culture was 9 g/l. The intracellular resveratrol- and pinosylvin levels expressed per gram dry weight therefore were 2.27/9=0.25 mg/g dry weight and 16.46/9=1.83 mg/g dry weight respectively.

REFERENCES

U.S. Pat. No. 6,521,748
US-A-2001053847
US-A-2004059103
US-A-2004023357
WO2006089898
WO2008/009728

Allina, S. M., Pri-Hadash, A., Theilmann, D. A., Ellis, B. E. and Douglas, C. J. (1998) 4-coumarate: Coenzyme A ligase in hybrid poplar. Properties of enzymes, cDNA cloning, and analysis of recombinant clones. Plant Physiol. 116, 743-754.

Aoyama, Y., Yoshida, Y., Kubota, S., Kumaoka, H. and Furumichi, A. (1978). NADPH-cytochrome P-450 reductase of yeast microsomes. Arch. Biochem. Biophys. 185, 362-369.

Becker J V, Armstrong G O, van der Merwe M J, Lambrechts M G, Vivier M A, Pretorius I S. (2003). Metabolic engineering of *Saccharomyces cerevisiae* for the synthesis of the wine-related antioxidant resveratrol. FEMS Yeast Res. 4, 79-85.

Blanquet, S., Meunier, J. P., Minekus, M., Marol-Bonnin, S., and Alric, M. (2003). Recombinant *Saccharomyces cerevisiae* Expressing P450 in Artificial Digestive Systems: a Model for Biodetoxication in the Human Digestive Environment. Appl. Environ. Microbiol. 69, 2884-2892.

Celotti E and others. (1996). Resveratrol content of some wines obtained from dried Valpolicella grapes: Recioto and Amarone. Journal of Chromatography A 730, 47-52.

Cochrane, F. C., Davin, L. B. and Lewis N. G. (2004). The *Arabidopsis* phenylalanine ammonia lyase gene family: kinetic characterization of the four PAL isoforms. Phytochemistry 65, 1557-1564.

Couzin, J. (2004) Aging Research's Family Feud. Science 303, 1276-1279.

Intracellular and extracellular levels of stilbenoids of PALCPR continuous culture at 300 hrs.
5 g/l glucose, 35 g/l galactose, D = 0.05, pH = 5.5., 1000 rpm

| Resveratrol Intracelullar (a) | Pinosylvin Intracelullar (b) | Resveratrol Extracelullar (c) | Pinosylvin Extracelullar (d) | Resveratrol Extracelullar In EtOH (e) | Pinosylvin Extracelullar In EtOH (f) | Resveratrol Total (a + e) | Pinosylvin Total (b + f) |
|---|---|---|---|---|---|---|---|
| 2.27 | 16.45 | 23.69 | 12.55 | 23.65 | 113.57 | 25.92 | 130.02 |
| 8.74 | 12.65 | 91.43 | 9.65 | 91.26 | 87.35 | 100.00 | 100.00 |
| 0.25 | 1.83 | — | — | — | — | — | — |

Ehlting, J., Büttner, D., Wang, Q., Douglas, C. J., Somssich, I. E. and Kombrink, E. (1999). Three 4-coumarate:coenzyme A ligases in *Arabidopsis thaliana* represents two evolutionary divergent classes in angiosperms. The plant journal. 19, 9-20.

Erdeniz N, Mortensen U H, Rothstein R.

Cloning-free PCR-based allele replacement methods.

Genome Res. 1997:7:1174-83.

Filpula, D., Vaslet, C. A., Levy, A., Sykes, A. and Strausberg, R. L. Nucleotide sequence of gene for phenylalanine ammonia-lyase from *Rhodotorula rubra*. (1988). Nucleic Acids Res. 16, 11381.

Gehm, B. D., McAndrews, J. M., Chien, P. Y. and Jameson, J. L. (1997). Resveratrol, a polyphenolic compound found in grapes and wine, is an agonist for the estrogen receptor. Proc. Natl. Acad. Sci. USA 94, 14138-14143.

Gems, D., Johnstone, I. L. and Clutterbuck, A. J. (1991). An autonomously replicating plasmid transforms *Aspergillus nidulans* at high frequency. Gene 98, 61-67.

Hain, R., Reif, H. J., Krause, E., Langebartels, R., Kindl, H., Vornam, B., Wiese, W., Schmelzer, E., Schreier, P. H., Stocker, R. H. and Stenzel, K. (1993). Disease resistance results from foreign phytoalexin expression in a novel plant. Nature 361, 153-156.

Hwang E I, Kaneko M, Ohnishi Y, Horinouchi S. (2003). Production of plant-specific flavanones by *Escherichia coli* containing an artificial gene cluster. Appl. Environ. Microbiol. 69, 2699-706.

Huang, M-T. (1997). Diet for cancer prevention. Food Sci. 24, 713-727

Hart, J. H. (1981) Annu. Rev. Phytopathology 19, 437-458.

Hart, J. H., Shrimpton, D. M. (1979) Phytopathology 69, 1138-1143.

Hall, S. S. (2003) In Vino Vitalis? Compounds Activate Life-Extending Genes. Science 301, 1165.

Hamberger, B. and Hahlbrock, K. (2004). The 4-coumarate: CoA ligase gene family in *Arabidopsis thaliana* comprises one rare, sinapate-activating and three commonly occurring isoenzymes. Proc. Natl. Acad. Sci. USA. 101, 2209-2214.

Jang, M., Cai, L., Udeani, G O., Slowing, K V., Thomas, C F., Beecher, C W W., Fong, H H S., Farnsworth, N R., Kinghorn, A D., Mehta, R G., Moon, R C., Pezzuto, J M. (1997). Cancer Chemopreventive Activity of Resveratrol, a Natural Product Derived from Grapes. Science 275, 218-220.

Jeandet, P. Bessis, R., Maume, B. F., Meunier, P., Peyron, D. and Trollat, P. (1995). Effect of Enological Practices on the Resveratrol Isomer Content of Wine J. Agric. Food Chem. 43, 316-319.

Jeandet, P. Bessis, R., Sbaghi, M. and Meunier, P. (1994). Occurrence of a resveratrol β-D-glucoside in wine: Preliminary studies. *Vitis* 33, 183-184.

Koopmann, E., Logemann, E. and Hahlbrock, K. (1999). Regulation and Functional Expression of Cinnamate 4-Hydroxylase from Parsley. Plant Physiol. 119, 49-55.

Kopp, P. (1998). Resveratrol, a phytooestrogen found in red wine. A possible explanation for the conundrum of the "French Paradox"? Eur. J. Endocrinol. 138, 619-620.

Kyndt J A, Meyer T E, Cusanovich M A, Van Beeumen J J. (2002). Characterization of a bacterial tyrosine ammonia lyase, a biosynthetic enzyme for the photoactive yellow protein. FEES Lett. 512, 240-244.

LaGrange, D. C., Pretorius, I. S. and Van Zyl, W. H. (1997). Cloning of the *Bacillus pumilus* beta-xylosidase gene (xynB) and its expression in *Saccharomyces cerevisiae*. Appl. Microbiol. Biotechnol. 47, 262-266.

Lin X., Kaul S., Rounsley S. D., Shea T. P., Benito M.-I., Town C. D., Fujii C. Y., Mason T. M., Bowman C. L., Barnstead M. E., Feldblyum T. V., Buell C. R., Ketchum K. A., Lee J. J., Ronning C. M., Koo H. L., Moffat K. S., Cronin L. A., Shen M., Pai G., Van Aken S., Umayam L., Tallon L. J., Gill J. E., Adams M. D., Carrera A. J., Creasy T. H., Goodman H. M., Somerville C. R., Copenhaver G. P., Preuss D., Nierman W. C., White O., Eisen J. A., Salzberg S. L., Fraser C. M., Venter J. C. (1999). Sequence and analysis of chromosome 2 of the plant *Arabidopsis thaliana*. Nature 402, 761-768.

Lobo, R. A. (1995). Benefits and risks of estrogen replacement therapy. Am. J. Obstet. Gynecol. 173, 982-989.

Martin, V. J. J., Pitera, D. J., Withers, S. T., Newman, J. D. and Keasling, J. D. (2003). Engineering a mevalonate pathway in *Escherichia coli* for production of terpenoids. Nature biotechnology 21, 796-802.

Mizutani, M., Ohta, D. and Sato, R. (1997). Isolation of a cDNA and a genomic clone encoding cinnamate 4-hydroxylase from *Arabidopsis* and its expression manner in planta. Plant Physiol. 113, 755-763.

Ro, D. K., Mah, N., Ellis, B. E. and Douglas, C. J. (2001). Functional Characterization and Subcellular Localization of Poplar (*Populus trichocarpa×Populus deltoides*) Cinnamate 4-Hydroxylase. Plant Physiol. 126, 317-329.

Ro D. K., Douglas C. J. (2004). Reconstitution of the entry point of plant phenylpropanoid metabolism in yeast (*Saccharomyces cerevisiae*): implications for control of metabolic flux into the phenylpropanoid pathway. J. Biol. Chem. 279, 2600-2607.

Rosler J, Krekel F, Amrhein N, Schmid J. (1997). Maize phenylalanine ammonia-lyase has tyrosine ammonia-lyase activity. Plant Physiol. 113, 175-179. activity. Plant physiol. 113, 175-179.

Samappito, S., Page, J. E., Schmidt, J., De-Eknamkul, W. and Kutchan, T. M. (2003). Aromatic and pyrone polyketides synthesized by a stilbene synthase from *Rheum tataricum*. Phytochemistry 62, 313-323.

Sambrook, J., Fritsch, E. F. and Maniatis, T. (1989). Molecular Cloning, A Laboratory Manual, 2d edition, Cold Spring Harbor, N.Y.

Schoppner, A.; Kindl, H. (1984) Purification and properties of a stilbene synthase from induced cell suspension cultures of peanut. J. Biol. Chem. 259, 6806-6811.

Seshime, Y., Juvvadi, P. R., Fujii, I. and Kitamoto, K. (2005). Genomic evidences for the existence of a phenylpropanoid metabolic pathway in *Aspergillus oryzae*. Biochem Biophys Res Commun. 337, 747-51.

Urban P., Mignotte, C., Kazmaier M., Delorme F. And Pompon D. (1997). Cloning, Yeast Expression, and Characterization of the Coupling of Two Distantly Related *Arabidopsis thaliana* NADPH-Cytochrome 450 Reductases with P450 CYP73A5. J. Biol. Chem. 272, 19176-19186.

Verduyn C, Postma E, Scheffers W A, Van Dijken J P. Effect of benzoic acid on metabolic fluxes in yeasts: a continuous-culture study on the regulation of respiration and alcoholic fermentation. Yeast. 1992:8:501-17.

Watts, K. T., Lee, P. C. and Schmidt-Dannert, C. (2004). Exploring recombinant flavonoid biosynthesis in metabolically engineered *Escherichia coli*. Chembiochem 5, 500-507.

The following is a summary of the nucleotide and amino acid sequences appearing herein:

SEQ ID NO: 1 is a nucleotide sequence from *Arabidopsis thaliana* encoding a phenylalanine ammonia lyase (PAL2).

SEQ ID NO: 2 is the amino acid sequence encoded by SEQ ID NO: 1.

SEQ ID NO: 3 is a nucleotide sequence from *Arabidopsis thaliana* encoding a cinnamate 4-hydroxylase (C4H).

SEQ ID NO: 4 is the amino acid sequence encoded by SEQ ID NO: 3.

SEQ ID NO: 5 is a nucleotide sequence from *Arabidopsis thaliana* encoding a 4-coumarate:CoenzymeA ligase (4CL1).

SEQ ID NO: 6 is the amino acid sequence encoded by SEQ ID NO: 5.

SEQ ID NO: 7 is a nucleotide sequence from *Rheum tataricum* encoding a resveratrol synthase (VST).
SEQ ID NO: 8 is the amino acid sequence encoded by SEQ ID NO: 7.
SEQ ID NO: 9 is a nucleotide sequence from *Rheum tataricum* encoding a resveratrol synthase (VST), which is codon-optimized for expression in *S. cerevisiae*.
SEQ ID NO: 10 is the amino acid sequence encoded by SEQ ID NO: 9.
SEQ ID NO: 11 is a nucleotide sequence from *Rhodobacter capsulatus* encoding a tyrosine ammonia lyase (TAL).
SEQ ID NO: 12 is the amino acid sequence encoded by SEQ ID NO: 11.
SEQ ID NO: 13 is a nucleotide sequence from *Rhodobacter capsulatus* encoding a tyrosine ammonia lyase (TAL), which is codon-optimized for expression in *S. cerevisiae*.
SEQ ID NO: 14 is the amino acid sequence encoded by SEQ ID NO: 13.
SEQ ID NO: 15 is a nucleotide sequence from *S. cerevisiae* encoding a NADPH:cytochrome P450 reductase (CPR1).
SEQ ID NO: 16 is the amino acid sequence encoded by SEQ ID NO: 15.
SEQ ID NO: 17 is a nucleotide sequence from *Arabidopsis thalianus* encoding a NADPH:cytochrome P450 reductase (AR2).
SEQ ID NO: 18 is the amino acid sequence encoded by SEQ ID NO: 17.
SEQ ID NOs 19-32 are primer sequences appearing in Table 1, Example 1.
SEQ ID NOs 33-34 are primer sequences appearing in Example 16.
SEQ ID NOs 35-38 are primer sequences appearing in Example 17.
SEQ ID NOs 39-46 are primer sequences appearing in Example 36, Table 1.
SEQ ID NOs 47-58 are primer sequences appearing in Example 37, Table 2.
SEQ ID NO: 59 is the gene sequence appearing in Example 39.
SEQ ID NO: 60 is the first gene sequence appearing in Example 41.
SEQ ID NOs 61-62 are primer sequences appearing in Example 41.
SEQ ID NO: 63 is the VST1 amino acid sequence in Example 41.
SEQ ID NO. 64 is the second gene sequence appearing in Example 41.

The invention claimed is:

1. A genetically engineered micro-organism comprising an engineered operative metabolic pathway producing at least 0.44 to 0.53 micrograms of resveratrol per gram on a dry weight basis of the genetically engineered micro-organism when cultured for a time and under conditions wherein the micro-organism produces resveratrol, wherein the engineered operative metabolic pathway produces:
   a) 4-coumaric acid from L-phenylalanine catalysed by a phenylalanine ammonia lyase and a cinnamate 4-hydroxylase expressed in the micro-organism or from tyrosine catalysed by a phenylalanine ammonia lyase or a tyrosine ammonia lyase expressed in said micro-organism;
   b) 4-coumaroyl-CoA from 4-coumaric acid catalysed by a 4-coumarate-CoA ligase expressed in the micro-organism; and
   c) resveratrol is produced from the 4-coumaroyl-CoA by a resveratrol synthase expressed in the micro-organism; wherein the micro-organism is *Saccharomyces cerevisiae* that is cultured in a media with a carbon substrate and does not require an external source of phenylalanine, tyrosine, cinnamic acid or coumaric acid, and further comprises a more than a native expression level of an acetyl coenzymeA carboxylase (ACC1) enzyme.

2. The micro-organism of claim 1, wherein the more than native expression level of the ACC1 enzyme has been provided by replacing a native promoter of a gene expressing the ACC1 enzyme with a promoter providing a higher level of expression.

3. The micro-organism of claim 2, wherein the native promoter is replaced with a strong constitutive yeast promoter.

4. The micro-organism of claim 3, wherein the strong constitutive promoter is a yeast promoter selected from the promoters for yeast genes:
   triosephoshosphate dehydrogenase 3 (TDH3), alcohol dehydrogenase 1 (ADH1), triose phosphate isomerase 1 (TPI1) 1 actin (ACTT), glyceraldehyde-3-phosphate dehydrogenase (GPD) and phosphoglucose isomerase (PGI).

5. The micro-organism of claim 1, wherein the more than native expression level of the ACC1 enzyme has been provided by recombinantly introducing into the micro-organism at least one copy of an exogenous genetic sequence encoding the ACC1 enzyme.

6. The micro-organism of claim 1, wherein the ACC1 enzyme is from *Saccharomyces cerevisiae*.

7. The micro-organism of claim 1, further comprising a more than a native expression level of a NADPH:cytochrome P450 reductase (CPR) enzyme.

8. The micro-organism of claim 7, wherein the more than native expression level of the CPR enzyme has been provided by replacing a native promoter of a gene expressing the CPR enzyme with a promoter providing a higher level of expression.

9. The micro-organism of claim 8, wherein the native promoter is replaced with a strong constitutive yeast promoter.

10. The micro-organism of claim 9, wherein the strong constitutive promoter is a yeast promoter selected from the promoters for yeast genes: triosephoshosphate dehydrogenase 3 (TDH3), alcohol dehydrogenase 1 (ADH1), triose phosphate isomerase 1 (TPI1) 1 actin (ACTT), glyceraldehyde-3-phosphate dehydrogenase (GPD) and phosphoglucose isomerase (PGI).

11. The micro-organism of claim 7, wherein the more than native expression level of the CPR enzyme has been provided by recombinantly introducing into the micro-organism at least one copy of an exogenous genetic sequence encoding the CPR enzyme.

12. The micro-organism of claim 7, wherein the CPR enzyme is from *Saccharomyces cerevisiae*.

13. The micro-organism of claim 1, wherein the micro-organism produces at least 1.83 milligrams of pinosylvin per gram on a dry weight basis.

14. A method for producing resveratrol or an oligomeric or glycosidically-bound derivative thereof, comprising:
   a) cultivating the genetically engineered micro-organism of claim 1; and
   b) recovering the resveratrol, or the oligomeric or glycosidically-bound derivative thereof, from the culture media.

* * * * *